US012283353B2

(12) United States Patent
Tsujimoto

(10) Patent No.: US 12,283,353 B2
(45) Date of Patent: Apr. 22, 2025

(54) METHOD FOR DESIGNING PRIMERS FOR MULTIPLEX PCR

(71) Applicant: FUJIFILM Corporation, Tokyo (JP)

(72) Inventor: Takayuki Tsujimoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1483 days.

(21) Appl. No.: 16/368,488

(22) Filed: Mar. 28, 2019

(65) Prior Publication Data

US 2019/0221292 A1 Jul. 18, 2019

Related U.S. Application Data

(63) Continuation of application No. PCT/JP2017/032262, filed on Sep. 7, 2017.

(30) Foreign Application Priority Data

Sep. 29, 2016 (JP) .............................. 2016-192241

(51) Int. Cl.
| | | |
|---|---|---|
| G16C 20/50 | (2019.01) | |
| C12N 15/09 | (2006.01) | |
| C12Q 1/68 | (2018.01) | |
| C12Q 1/6853 | (2018.01) | |
| C12Q 1/686 | (2018.01) | |
| C12Q 1/6876 | (2018.01) | |
| G16B 25/20 | (2019.01) | |
| G16B 30/00 | (2019.01) | |
| G16C 20/20 | (2019.01) | |
| G16C 20/60 | (2019.01) | |
| G16C 20/90 | (2019.01) | |

(52) U.S. Cl.
CPC .............. *G16C 20/50* (2019.02); *C12N 15/09* (2013.01); *C12Q 1/6853* (2013.01); *C12Q 1/686* (2013.01); *C12Q 1/6876* (2013.01); *G16B 25/20* (2019.02); *G16B 30/00* (2019.02); *G16C 20/20* (2019.02); *G16C 20/60* (2019.02); *G16C 20/90* (2019.02); *C12Q 1/68* (2013.01)

(58) Field of Classification Search
CPC ........ G16C 20/50; G16C 20/20; G16C 20/90; G16C 20/60; C12N 15/09; C12Q 1/6853; C12Q 1/686; C12Q 1/6876; C12Q 1/68; G16B 25/20; G16B 30/00
See application file for complete search history.

(56) References Cited

U.S. PATENT DOCUMENTS

| 2010/0070452 A1 | 3/2010 | Nakamura |
| 2018/0032669 A1 | 2/2018 | Tsujimoto |
| 2018/0087112 A1 | 3/2018 | Ouchi et al. |

FOREIGN PATENT DOCUMENTS

| CN | 101613698 A | 12/2009 |
| JP | 5079694 B2 | 11/2012 |
| WO | 2008/004691 A1 | 1/2008 |
| WO | 2016/159111 A1 | 10/2016 |
| WO | 2016/159132 A1 | 10/2016 |

OTHER PUBLICATIONS

Kaderali, L. Primer design for multiplexed genotyping. Methods in Molecular Biology 402: 269-286. (Year: 2007).*
Zhang, R. Quantifying RNA allelic ratios but microfluidic multiplex PCR and sequencing. Nature Methods 11(1): 51-56. (Year: 2014).*
Wingo, TS. MPD: multiplex primer design for next-generation targeted sequencing. BMC Bioinformatics 18(14): pp. 1-5. (Year: 2017).*
Shen, Zhiyong et al., "MPprimer: a program for reliable multiplex PCR primer design", BMC Bioinformatics, vol. 11, No. 143, 2010, pp. 1-7 (7 pages total).
Kaderali, Lars et al., "Primer-design for multiplexed genotyping", Nucleic Acids Research, vol. 31, No. 6, 2003, pp. 1796-1802 (7 pages total).
International Search Report dated Dec. 5, 2017 from the International Searching Authority in counterpart International Application No. PCT/JP2017/032262.
International Preliminary Report on Patentability dated Apr. 2, 2019 from the International Bureau in counterpart International Application No. PCT/JP2017/032262.
Written Opinion dated Dec. 5, 2017 from the International Bureau in counterpart International Application No. PCT/JP2017/032262.
Communication dated Sep. 23, 2019, from the European Patent Office in counterpart European Application No. 17855653.6.
Masato Mitsuhashi, "Technical Report: Part 2. Basic Requirements for Designing Optimal PCR Primers", Journal of Clinical Laboratory Analysis, Jan. 1, 1996, vol. 10, No. 5, pp. 285-293 (9 pages total).
Office Action issued Jan. 11, 2022 in Chinese Application No. 201780060228.1.
Office Action issued Mar. 3, 2020 in Japanese Application No. 2018-542323.

* cited by examiner

*Primary Examiner* — Olivia M. Wise
*Assistant Examiner* — Robert J. Kallal
(74) *Attorney, Agent, or Firm* — Sughrue Mion, PLLC

(57) ABSTRACT

There is provided a method for designing primers for multiplex PCR, for assigning priorities to candidate amplification regions on same chromosomal DNA and designing primers for PCR amplifying the candidate amplification regions according to the priorities, the method having a feature in a method for assigning priorities.

10 Claims, 13 Drawing Sheets

Specification includes a Sequence Listing.

FIG. 10

| | AMPLIFICATION PURPOSE | AMPLIFICATION PURPOSE | AMPLIFICATION PURPOSE | AMPLIFICATION PURPOSE | AMPLIFICATION PURPOSE | AMPLIFICATION PURPOSE | AMPLIFICATION PURPOSE | AMPLIFICATION PURPOSE | AMPLIFICATION PURPOSE |
|---|---|---|---|---|---|---|---|---|---|
| ORDER OF PRIORITIES | ⑦ | ④ | ⑤ | ⑧ | ③ | ⑨ | ② | ① | ⑥ |
| CHROMOSOMAL DNA | | | | | | | | | |
| CANDIDATE AMPLIFICATION REGIONS | R01 | R02 | R03 | R04 | R05 | R06 | R07 | R08 | R09 |
| NUMBER OF CANDIDATE PRIMERS | 30 | 10 | 20 | 50 | 10 | 70 | 10 | 5 | 20 |

SUCCESSFUL AMPLIFICATION

FIG. 11

| | AMPLIFICATION PURPOSE | AMPLIFICATION PURPOSE | AMPLIFICATION PURPOSE | AMPLIFICATION PURPOSE | AMPLIFICATION PURPOSE | | | | |
|---|---|---|---|---|---|---|---|---|---|
| ORDER OF PRIORITIES | ① | ② | ③ | ④ | ⑤ | ⑥ | ⑦ | ⑧ | ⑨ |
| CHROMOSOMAL DNA | | | | | | | | | |
| CANDIDATE AMPLIFICATION REGIONS | R01 | R02 | R03 | R04 | R05 | R06 | R07 | R08 | R09 |
| | V.F.=0.1 | V.F.=0.3 | V.F.=0.2 | V.F.=0.5 | V.F.=0.1 | V.F.=0.7 | V.F.=0.2 | V.F.=0.4 | V.F.=0.4 |
| | ΔV.F.=0.4 | ΔV.F.=0.2 | ΔV.F.=0.3 | ΔV.F.=0 | ΔV.F.=0.4 | ΔV.F.=0.2 | ΔV.F.=0.3 | ΔV.F.=0.1 | ΔV.F.=0.1 |

FIG. 12

| | | AMPLIFICATION PURPOSE | | AMPLIFICATION PURPOSE | | AMPLIFICATION PURPOSE | | AMPLIFICATION PURPOSE | AMPLIFICATION PURPOSE |
|---|---|---|---|---|---|---|---|---|---|
| ORDER OF PRIORITIES | ⑧ | ④ | ⑥ | ① | ⑨ | ⑤ | ⑦ | ② | ③ |
| CHROMOSOMAL DNA | | | | | | | | | |
| CANDIDATE AMPLIFICATION REGIONS | R01 | R02 | R03 | R04 | R05 | R06 | R07 | R08 | R09 |
| | V.F.=0.1 | V.F.=0.3 | V.F.=0.2 | V.F.=0.5 | V.F.=0.1 | V.F.=0.7 | V.F.=0.2 | V.F.=0.4 | V.F.=0.4 |
| | ΔV.F.=0.4 | ΔV.F.=0.2 | ΔV.F.=0.3 | ΔV.F.=0 | ΔV.F.=0.4 | ΔV.F.=0.2 | ΔV.F.=0.3 | ΔV.F.=0.1 | ΔV.F.=0.1 |

METHOD FOR DESIGNING PRIMERS FOR MULTIPLEX PCR

CROSS-REFERENCE TO RELATED APPLICATIONS

This application is a Continuation of PCT International Application No. PCT/JP2017/032262 filed on Sep. 7, 2017, which claims priority under 35 U.S.C. § 119(a) to Japanese Patent Application No. 2016-192241 filed on Sep. 29, 2016. The above application is hereby expressly incorporated by reference, in its entirety, into the present application.

BACKGROUND OF THE INVENTION

1. Field of the Invention

The present invention relates to a method for designing primers for multiplex PCR.

2. Description of the Related Art

DNA sequencers and the like, which have been developed in recent years, facilitate genetic analysis. However, the total base length of the genome is generally enormous, and, on the other hand, sequencers have limited reading capacity. Accordingly, a PCR method is spreading as a technique for efficient and accurate genetic analysis by amplifying only a necessary specific gene region and reading only its base sequence. In particular, a method for selectively amplifying a plurality of gene regions by simultaneously supplying a plurality of types of primers to a certain single PCR reaction system is referred to as multiplex PCR.

Multiplex PCR efficiently amplifies a plurality of regions from a minute amount of DNA and is thus a technique useful for noninvasive prenatal diagnosis.

JP5079694B describes a method for designing primers to be used in multiplex PCR for m candidate amplification regions that are arranged on the same chromosome in coordinate order. Here, m is an integer greater than or equal to 1.

First, candidate primers corresponding to a first candidate amplification region $X_1$ from a base sequence of DNA to be amplified are selected. At this time, candidate primers are assumed to be selected based on the primer melting temperature, the GC content, the base sequence length, the base sequence specificity, and the score indicating the unlikelihood of formation of a hairpin structure and a primer dimer. Among n candidate primers corresponding to the candidate amplification region $X_1$ for which the Tm (Melting Temperature), the GC content, and the base sequence length fall within predetermined ranges, the candidate having the highest score, where the score indicates the superiority of the candidate primer and is calculated from the base sequence specificity and the unlikelihood of formation of a hairpin structure and a primer dimer, is referred to as $P_{11}$, the candidate having the second highest score is referred to as $P_{12}$, and the n-th candidate is referred to as $P_{1n}$. Also, n' candidate primers $P_{21}$, $P_{22}$, ..., and $P_{2n'}$ corresponding to a second candidate amplification region $X_2$ are selected in a manner similar to that described above. Similar operations are repeated for all the candidate amplification regions to select k candidate primers $P_{m1}$, $P_{m2}$, ..., and $P_{mk}$ corresponding to the m-th candidate amplification region $X_m$.

Then, to select a combination of primers that are optimum for a reaction from the selected candidate primers, whether primers in different candidate amplification regions have no complementary base sequences at unintended sites is examined. Primers that are less likely to form a primer dimer among primers in different candidate amplification regions are primers available for multiplex PCR.

SUMMARY OF THE INVENTION

However, direct multiplex PCR for minute DNA samples having low redundancy, such as genomic DNA extracted from a single cell, imposes very restrictive primer design conditions such as complementarity/specificity, and thus primers available for multiplex PCR may be difficult to employ for all the candidate amplification regions in which primers for multiplex PCR are to be designed.

As a result, the number of candidate amplification regions (hereinafter referred to sometimes as "amplification target regions") for which primers available for multiplex PCR are successfully employed becomes small, and the following problems occur.

The first problem is that amplification target regions for which amplification by multiplex PCR is not successful are generated and it is thus difficult to ensure a necessary number of regions for analysis such as genotyping.

The second problem is that even if a necessary number of regions for analysis such as genotyping can be ensured, high accuracy is not achievable.

Accordingly, it is an object of the present invention to provide a method for designing primers for multiplex PCR, which can ensure a necessary number of regions or achieve high accuracy even when direct multiplex PCR for minute DNA samples having low redundancy, such as genomic DNA extracted from a single cell, is performed.

As a result of considerations, the present inventor has found that the generation of amplification target regions for which amplification by multiplex PCR is not successful may be caused by the non-presence of at least some of regions to be amplified due to chromosome deletion, DNA fragmentation, or the like, that, even for primers employed in silico as primers available for multiplex PCR, primer mismatches may be observed in an in vitro multiplex PCR experiment system, and that failure to achieve high accuracy even if a necessary number of regions for analysis such as genotyping can be ensured may be caused by the need for more regions to achieve the desired accuracy unless the variant frequency of a variant in an amplification target region is close to 0.5.

As a result of further studies to solve the problems described above, the present inventor has found a method for designing primers for multiplex PCR, for assigning priorities to candidate amplification regions and designing primers for PCR amplifying the candidate amplification regions according to the priorities, in which: ensuring that the distance between candidate amplification regions that are consecutive in order of priority is large limits a range over which a partial deletion of a chromosome, DNA fragmentation, or the like has an effect to reduce the number of amplification target regions for which amplification by multiplex PCR is not successful; assigning priorities so that a candidate amplification region having a smaller number of candidate primers that can be designed is assigned a higher priority can increase the number of primers to be employed as primers available for multiplex PCR to reduce the number of amplification target regions for which amplification by multiplex PCR is not successful; and assigning priorities so that a candidate amplification region in which a variant has a variant frequency closer to 0.5 is assigned a higher priority can achieve desired accuracy with a smaller number of regions. Finally, the present inventor has accomplished the present invention.

That is, the present invention provides the following [1] to [6].

[1] A method for designing primers for multiplex PCR, for assigning priorities to candidate amplification regions on same chromosomal DNA and designing primers for PCR amplifying the candidate amplification regions according to the priorities, the priorities being assigned using a method for assigning priorities to candidate amplification regions on same chromosomal DNA, the method including the following steps:

a step of inputting identification information and coordinate information of n candidate amplification regions on same chromosomal DNA via input means and storing the identification information and the coordinate information in storage means;

a first priority setting step of, by arithmetic means, searching for a candidate amplification region having a minimum coordinate value by using the identification information and coordinate information of the candidate amplification regions stored in the storage means, assigning priority information indicating a priority of 1, which corresponds to a highest priority, to the found candidate amplification region, and storing the priority information in the storage means;

a second priority setting step of, by the arithmetic means, searching for a candidate amplification region having a maximum coordinate value by using the identification information and coordinate information of the candidate amplification regions stored in the storage means, assigning priority information indicating a priority of 2, which corresponds to a second highest priority, to the found candidate amplification region, and storing the priority information in the storage means; and a k-th priority setting step of, by the arithmetic means, searching for a candidate amplification region $R_i$ and a candidate amplification region $R_j$ by using the identification information, coordinate information, and priority information of the candidate amplification regions stored in the storage means, the candidate amplification region $R_i$ and the candidate amplification region $R_j$ being respectively a candidate amplification region whose priority is i, whose coordinate value is $r_i$, and whose identification name is $R_i$ and a candidate amplification region whose priority is j, whose coordinate value is and whose identification name is $R_j$ and satisfying a condition that no candidate amplification region assigned a priority is present but at least one candidate amplification region yet to be assigned a priority is present between the candidate amplification region $R_i$ and the candidate amplification region $R_j$, then calculating a coordinate value $r_{i-j}$ of a midpoint of the candidate amplification region $R_i$ and the candidate amplification region $R_j$ in accordance with $r_{i-j}=(r_i+r_j)/2$, further searching for a candidate amplification region having a coordinate value closest to the coordinate value $r_{i-j}$ of the midpoint, assigning priority information indicating a priority of k, which corresponds to a k-th highest priority, to the found candidate amplification region, and storing the priority information in the storage means, wherein the k-th priority setting step is repeated for k=3 to n, where n is an integer satisfying 3≤n, k is an integer satisfying 3≤k≤n, i and j satisfy 1≤i≤k−1, 1≤j≤k−1, and i≠j, $r_i$ and $r_j$ satisfy $r_{min} \leq r_i \leq r_{max}$, $r_{min} \leq r_j \leq r_{max}$, and $r_i \neq r_j$, and $r_{min}$ and $r_{max}$ are respectively a minimum coordinate value and a maximum coordinate value of the n candidate amplification regions.

[2] A method for designing primers for multiplex PCR, for assigning priorities to candidate amplification regions on same chromosomal DNA and designing primers for PCR amplifying the candidate amplification regions according to the priorities, the priorities being assigned using a method for assigning priorities to candidate amplification regions on same chromosomal DNA, the method including the following steps:

a step of inputting identification information and coordinate information of n candidate amplification regions on same chromosomal DNA via input means and storing the identification information and the coordinate information in storage means;

a first priority setting step of, by arithmetic means, searching for a candidate amplification region having a maximum coordinate value by using the identification information and coordinate information of the candidate amplification regions stored in the storage means, assigning priority information indicating a priority of 1, which corresponds to a highest priority, to the found candidate amplification region, and storing the priority information in the storage means;

a second priority setting step of, by the arithmetic means, searching for a candidate amplification region having a minimum coordinate value by using the identification information and coordinate information of the candidate amplification regions stored in the storage means, assigning priority information indicating a priority of 2, which corresponds to a second highest priority, to the found candidate amplification region, and storing the priority information in the storage means; and a k-th priority setting step of, by the arithmetic means, searching for a candidate amplification region $R_i$ and a candidate amplification region $R_j$ by using the identification information, coordinate information, and priority information of the candidate amplification regions stored in the storage means, the candidate amplification region $R_i$ and the candidate amplification region $R_j$ being respectively a candidate amplification region whose priority is i, whose coordinate value is $r_i$, and whose identification name is $R_i$ and a candidate amplification region whose priority is j, whose coordinate value is $r_j$, and whose identification name is $R_j$ and satisfying a condition that no candidate amplification region assigned a priority is present but at least one candidate amplification region yet to be assigned a priority is present between the candidate amplification region $R_i$ and the candidate amplification region $R_j$, then calculating a coordinate value $r_{i-j}$ of a midpoint of the candidate amplification region $R_i$ and the candidate amplification region $R_j$ in accordance with $r_{i-j}=(r_i+r_j)/2$, further searching for a candidate amplification region having a coordinate value closest to the coordinate value $r_{i-j}$ of the midpoint, assigning priority information indicating a priority of k, which corresponds to a k-th highest priority, to the found candidate amplification region, and storing the priority information in the storage means,
wherein the k-th priority setting step is repeated for k=3 to n,
where n is an integer satisfying 3≤n, k is an integer satisfying 3≤k≤n, i and j satisfy 1≤i≤k−1, 1≤j≤k−1, and i≠j, $r_i$ and $r_j$ satisfy $r_{min} \leq r_i \leq r_{max}$, $r_{min} \leq r_j \leq r_{max}$, and $r_i \neq r_j$, and $r_{min}$ and $r_{max}$ are respectively a minimum coordinate value and a maximum coordinate value of the n candidate amplification regions.

[3] A method for designing primers for multiplex PCR, for assigning priorities to candidate amplification regions on same chromosomal DNA and designing primers for PCR amplifying the candidate amplification regions according to the priorities,
the priorities being assigned using a method for assigning priorities to candidate amplification regions on same chromosomal DNA, the method including the following steps:
a step of inputting identification information and coordinate information of n candidate amplification regions on same chromosomal DNA via input means and storing the identification information and the coordinate information in storage means;
a first priority setting step of, by arithmetic means, searching for a candidate amplification region having a minimum coordinate value by using the identification information and coordinate information of the candidate amplification regions stored in the storage means, assigning priority information indicating a priority of 1, which corresponds to a highest priority, to the found candidate amplification region, and storing the priority information in the storage means; and
a k-th priority setting step of, by the arithmetic means, searching for an identification name $R_{k-1}$ and a coordinate value $r_{k-1}$ of a candidate amplification region whose priority is k−1 by using the identification information, coordinate information, and priority information of the candidate amplification regions stored in the storage means, calculating $T=r_{k-1}+t$,
when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if a candidate amplification region satisfying these conditions is present, assigning a priority of k to a candidate amplification region yet to be assigned priority information and having a smallest coordinate value greater than or equal to $r_{k-1}+t$, and storing the candidate amplification region assigned a priority of k in the storage means,
when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if there is no candidate amplification region satisfying these conditions, assigning a priority of k to a candidate amplification region yet to be assigned priority information and having a smallest coordinate value greater than or equal to $r_{min}$, and storing the candidate amplification region assigned a priority of k in the storage means, and
when $T=r_{k-1}+t>r_{max}$ is satisfied, assigning a priority of k to a candidate amplification region yet to be assigned a priority and having a smallest coordinate value greater than or equal to $r_{min}$, and storing the candidate amplification region assigned a priority of k in the storage means,
wherein the k-th priority setting step is repeated for k=2 to n,
where n is an integer satisfying 3≤n, k is an integer satisfying 2≤k≤n, t is a real number satisfying t>0, $r_{k-1} \neq r_k$ is satisfied, and $r_{min}$ and $r_{max}$ are respectively a minimum coordinate value and a maximum coordinate value of the n candidate amplification regions.

[4] A method for designing primers for multiplex PCR, for assigning priorities to candidate amplification regions on same chromosomal DNA and designing primers for PCR amplifying the candidate amplification regions according to the priorities,
the priorities being assigned using a method for assigning priorities to candidate amplification regions on same chromosomal DNA, the method including the following steps:
a step of inputting identification information and coordinate information of n candidate amplification regions on same chromosomal DNA via input means and storing the identification information and the coordinate information in storage means;
a first priority setting step of, by arithmetic means, searching for a candidate amplification region having a maximum coordinate value by using the identification information and coordinate information of the candidate amplification regions stored in the storage means, assigning priority information indicating a priority of 1, which corresponds to a highest priority, to the found candidate amplification region, and storing the priority information in the storage means; and
a k-th priority setting step of, by the arithmetic means, searching for an identification name $R_{k-1}$ and a coordinate value $r_{k-1}$ of a candidate amplification region whose priority is k−1 by using the identification information, coordinate information, and priority information of the candidate amplification regions stored in the storage means, calculating $T=r_{k-1}+t$,
when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if a candidate amplification region satisfying these conditions is present, assigning a priority of k to a candidate amplification region yet to be assigned priority information and having a smallest coordinate value greater than or equal to $r_{k-1}+t$, and storing the candidate amplification region assigned a priority of k in the storage means,
when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if there is no candidate amplification region satisfying these conditions, assigning a priority of k to a candidate amplification region yet to be assigned priority information and having a smallest coordinate value greater than or equal to $r_{min}$, and storing the candidate amplification region assigned a priority of k in the storage means, and
when $T=r_{k-1}+t>r_{max}$ is satisfied, assigning a priority of k to a candidate amplification region yet to be assigned a priority and having a smallest coordinate value greater than or equal to $r_{min}$, and storing the candidate amplification region assigned a priority of k in the storage means, wherein the k-th priority setting step is repeated for k=2 to n, where n is an integer satisfying 3≤n, k is an integer satisfying 2≤k≤n, t is a real number satisfying t>0, $r_{k-1} \neq r_k$ is satisfied, and $r_{min}$ and $r_{max}$ are respectively a minimum coordinate value and a maximum coordinate value of the n candidate amplification regions.

[5] A method for designing primers for multiplex PCR, for assigning priorities to candidate amplification regions on same chromosomal DNA and designing primers for PCR amplifying the candidate amplification regions according to the priorities, the priorities being assigned using a method for assigning priorities to candidate amplification regions on same chromosomal DNA, the method including the following steps:

a step of inputting identification information and number-of-candidate-primer information of n candidate amplification regions on same chromosomal DNA via input means and storing the identification information and the number-of-candidate-primer information in storage means; and a k-th priority setting step of, by arithmetic means, searching for a candidate amplification region including the k-th smallest number of candidate primers by using the identification information and number-of-candidate-primer information of the candidate amplification regions stored in the storage means, assigning priority information indicating a priority of k, which corresponds to a k-th highest priority, to the found candidate amplification region, and storing the priority information in the storage means, wherein the k-th priority setting step is repeated for k=1 to n, where n is an integer satisfying n≥2, and k is an integer satisfying 1≤k≤n.

[6] A method for designing primers for multiplex PCR, for assigning priorities to candidate amplification regions and designing primers for PCR amplifying the candidate amplification regions according to the priorities, the priorities being assigned using a method for assigning priorities to candidate amplification regions, the method including the following steps:

a step of inputting identification information and variant frequency information of n candidate amplification regions on chromosomal DNA via input means and storing the identification information and the variant frequency information in storage means; and a k-th priority setting step of, by arithmetic means, calculating a variant frequency difference=$|0.5-VF_i|$ of a candidate amplification region having an identification name $R_i$ and a variant frequency $VF_i$ by using the identification information and variant frequency information of the candidate amplification regions stored in the storage means, searching for a candidate amplification region having a k-th smallest variant frequency difference, assigning priority information indicating a priority of k, which corresponds to a k-th highest priority, to the found candidate amplification region, and storing the priority information in the storage means, wherein the k-th priority setting step is repeated for k=1 to n.

where n is an integer satisfying n≥2, and k is an integer satisfying 1≤k≤n.

According to the present invention, it is possible to provide a method for designing primers for multiplex PCR, which can ensure a necessary number of regions or achieve high accuracy even when direct multiplex PCR for minute DNA samples having low redundancy, such as genomic DNA extracted from a single cell, is performed.

According to the present invention, furthermore, it is possible to reduce the number of amplification target regions for which PCR amplification is unsuccessful due to influences such as chromosome deletion or DNA fragmentation and to ensure a necessary number of regions for analysis such as genotyping.

According to the present invention, furthermore, it is possible to employ more primers available for multiplex PCR for candidate amplification regions having a smaller number of candidate primers to reduce the number of amplification target regions for which PCR amplification is unsuccessful, and to ensure a necessary number of regions for analysis such as genotyping.

According to the present invention, moreover, it is possible to achieve high accuracy with a smaller number of regions by increasing the ratio of a region in which the variant frequency of a variant is close to 0.5 to amplification target regions.

BRIEF DESCRIPTION OF THE DRAWINGS

FIG. 10 is a conceptual diagram for describing a priority setting method according to a third aspect of the present invention, in which candidate amplification regions are assigned priorities in order of the number of candidate primers from lowest to highest, and nine candidate amplification regions R01 to R09 on the same chromosomal DNA can be amplified;

FIG. 11 is a conceptual diagram illustrating the conventional priority setting method, in which candidate amplification regions are assigned priorities in order from smallest to largest in terms of coordinate, and when five out of nine candidate amplification regions are amplified and genotyping analysis is performed, high analysis accuracy is not obtained;

FIG. 12 is a conceptual diagram for describing a priority setting method according to a fourth aspect of the present invention, in which candidate amplification regions are assigned priorities in order of SNP variant frequency from closest to farthest from 0.5, and when five out of nine candidate amplification regions are amplified and genotyping analysis is performed, high analysis accuracy is obtained;

DESCRIPTION OF THE PREFERRED EMBODIMENTS

In the present invention, a range indicated using "... to ..." refers to a range including values given before and after "to". For example, regarding A and B, "A to B" refers to a range including A and B.

In the present invention, furthermore, a candidate amplification region refers to a candidate region that is a region on a genomic DNA and that is to be PCR amplified for purposes such as genotyping or determination of the number of chromosomes.

The main abbreviations used herein and their meanings are as follows.
DNA: Deoxyribonucleic acid
PCR: Polymerase Chain Reaction
SNP: Single Nucleotide Polymorphism
SNPs: Plural form of SNP
SNV: Single Nucleotide Variant, a generic concept of SNP
V.F.: Variant Frequency
ΔV.F.: Difference in variant frequency (absolute value of the difference from a variant frequency of 0.5)
in silico: It means "using a computer" (bioinformatics)
in vitro: It means, compared to in silico, "by wet experiment" (bioinformatics)

[Hardware (Execution Device)]

Figure 1:
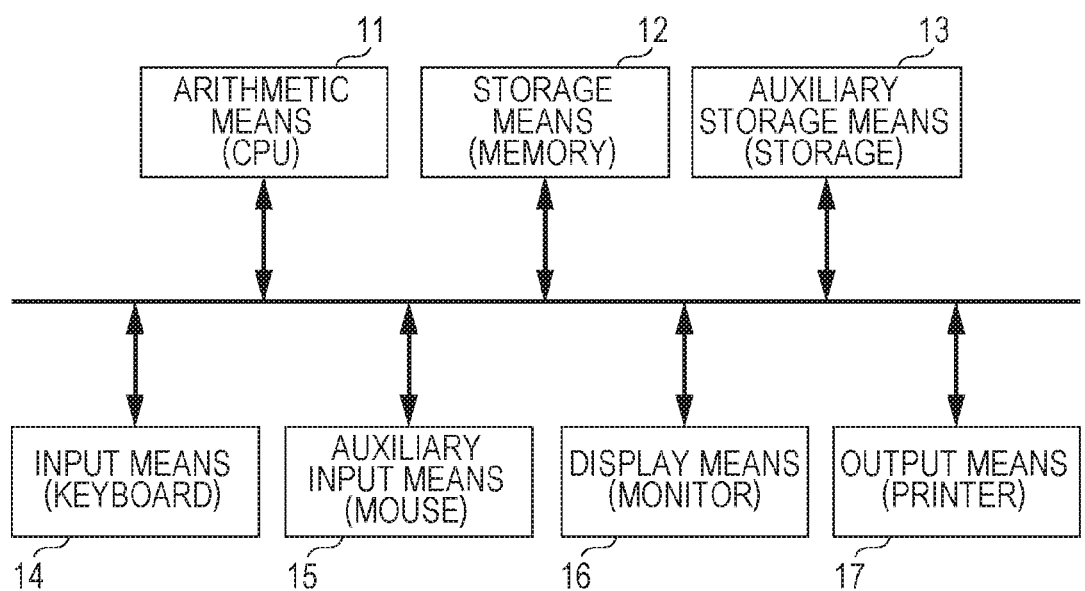
FIG. 1 is a conceptual diagram illustrating hardware used in the setting of priorities according to the present invention.

A device (also referred to as "hardware" or "execution device") that executes a priority setting method according to the present invention will be described with reference to FIG. 1.

In the present invention, the setting of priorities is performed by hardware (device) including arithmetic means (CPU; Central Processing Unit) 11, storage means (memory) 12, auxiliary storage means (storage) 13, input means (keyboard) 14, and display means (monitor) 16. This device may further include auxiliary input means (mouse) 15, output means (printer) 17, and so on.

Each means will be described.

The input means (keyboard) 14 is means for inputting instructions, data, and so on to the device. The auxiliary input means (mouse) 15 is used instead of or together with the input means (keyboard) 14.

The arithmetic means (CPU) 11 is means for performing arithmetic processing.

The storage means (memory) 12 is means for storing results of the arithmetic processing performed by the arithmetic means (CPU) 11 or for storing input from the input means (keyboard) 14.

The auxiliary storage means (storage) 13 is a storage that stores an operating system, a program for determining the necessary number of loci, and so on. A portion of the auxiliary storage means (storage) 13 can also be used for extension of the storage means (memory) 12 (virtual memory).

[1. First Aspect of Present Invention]

A first aspect of the present invention provides a solution to the first problem that amplification target regions for which amplification by multiplex PCR is not successful are generated and it is thus difficult to ensure a necessary number of regions for analysis such as genotyping. In the following, a description will be given with reference to FIG. 1, FIG. 2, and FIG. 3, as appropriate.

The first aspect of the present invention provides a method for designing primers for multiplex PCR, for assigning priorities to candidate amplification regions on same chromosomal DNA and designing primers for PCR amplifying the candidate amplification regions according to the priorities.

The priorities are assigned using a method for assigning priorities to candidate amplification regions on same chromosomal DNA, the method including the following steps.

Figure 2:
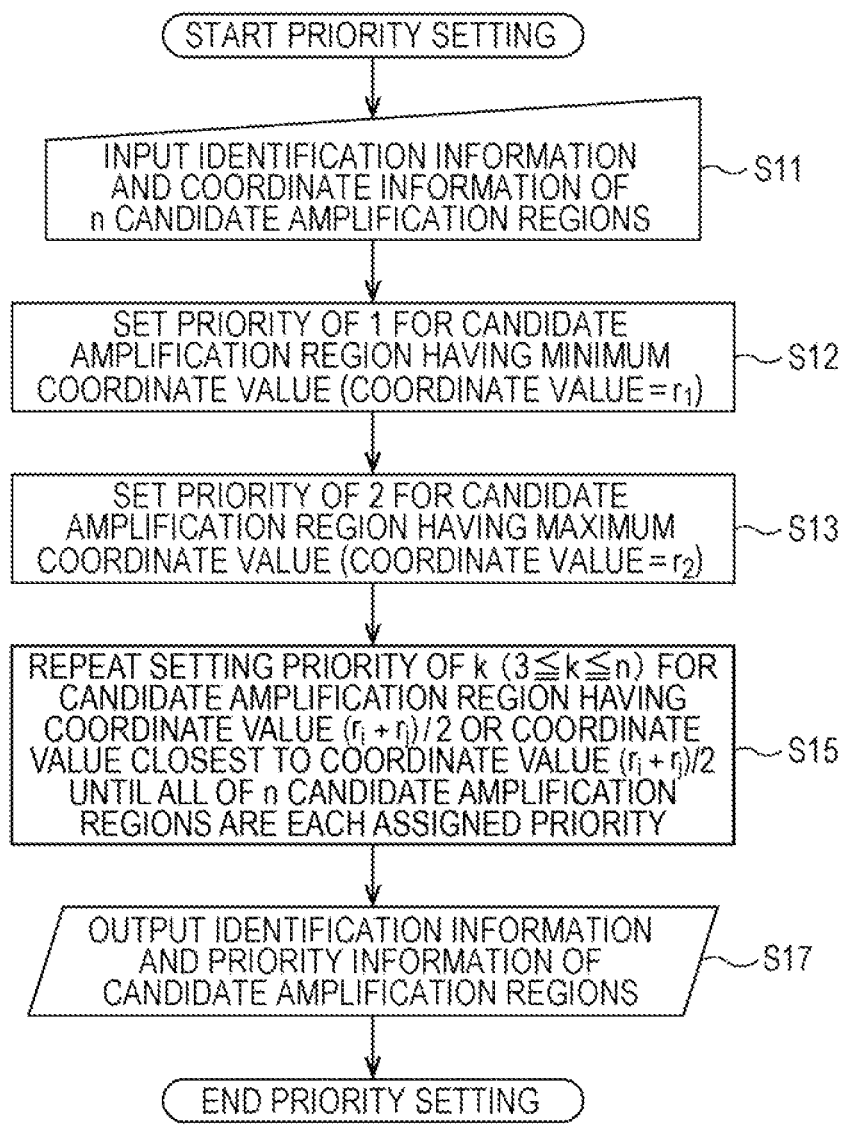
FIG. 2 is a flow diagram illustrating a priority setting method according to a first aspect of the present invention.

A step of inputting identification information and coordinate information of n candidate amplification regions on same chromosomal DNA via the input means 14 and storing the identification information and the coordinate information in the storage means 12 (S11 in FIG. 2).

A first priority setting step of, by the arithmetic means 11, searching for a candidate amplification region having a minimum coordinate value by using the identification information and coordinate information of the candidate amplification regions stored in the storage means 12, assigning priority information indicating a priority of 1, which corresponds to the highest priority, to the found candidate amplification region, and storing the priority information in the storage means 12 (S12 in FIG. 2).

A second priority setting step of, by the arithmetic means 11, searching for a candidate amplification region having a maximum coordinate value by using the identification information and coordinate information of the candidate amplification regions stored in the storage means 12, assigning priority information indicating a priority of 2, which corresponds to the second highest priority, to the found candidate amplification region, and storing the priority information in the storage means 12, (S13 in FIG. 2).

A k-th priority setting step of, by the arithmetic means 11, searching for a candidate amplification region $R_i$ and a candidate amplification region $R_j$ by using the identification information, coordinate information, and priority information of the candidate amplification regions stored in the storage means 12, the candidate amplification region $R_i$ and the candidate amplification region. $R_j$ being respectively a candidate amplification region whose priority is i, whose coordinate value is $r_i$, and whose identification name is $R_i$ and a candidate amplification region whose priority is j, whose coordinate value is $r_j$, and whose identification name is $R_j$ and satisfying a condition that no candidate amplification region assigned a priority is present but at least one candidate amplification region yet to be assigned a priority is present between the candidate amplification region $R_i$ and the candidate amplification region then calculating a coordinate value $r_{i\text{-}j}$ of a midpoint of the candidate amplification region $R_i$ and the candidate amplification region $R_j$ in accordance with $r_{i\text{-}j}=(r_i+r_j)/2$, further searching for a candidate amplification region having a coordinate value closest to the coordinate value $r_{i\text{-}j}$ of the midpoint, assigning priority information indicating a priority of k, which corresponds to the k-th highest priority, to the found candidate amplification region, and storing the priority information in the storage means 12 (S15 in FIG. 2).

The k-th priority setting step is repeated for k=3 to n (S14 and S16 in FIG. 2).

Note that n is an integer satisfying 3≤n, k is an integer satisfying 3≤k≤n, i and j satisfy 1≤i≤k−1, 1≤j≤k−1, and i≠j, $r_i$ and $r_j$ satisfy $r_{min} \leq r_i \leq r_{max}$, $r_{min} \leq r_j \leq r_{max}$, and $r_i \neq r_j$, and $r_{min}$ and $r_{max}$ are respectively a minimum coordinate value and a maximum coordinate value of the n candidate amplification regions.

Figure 3:
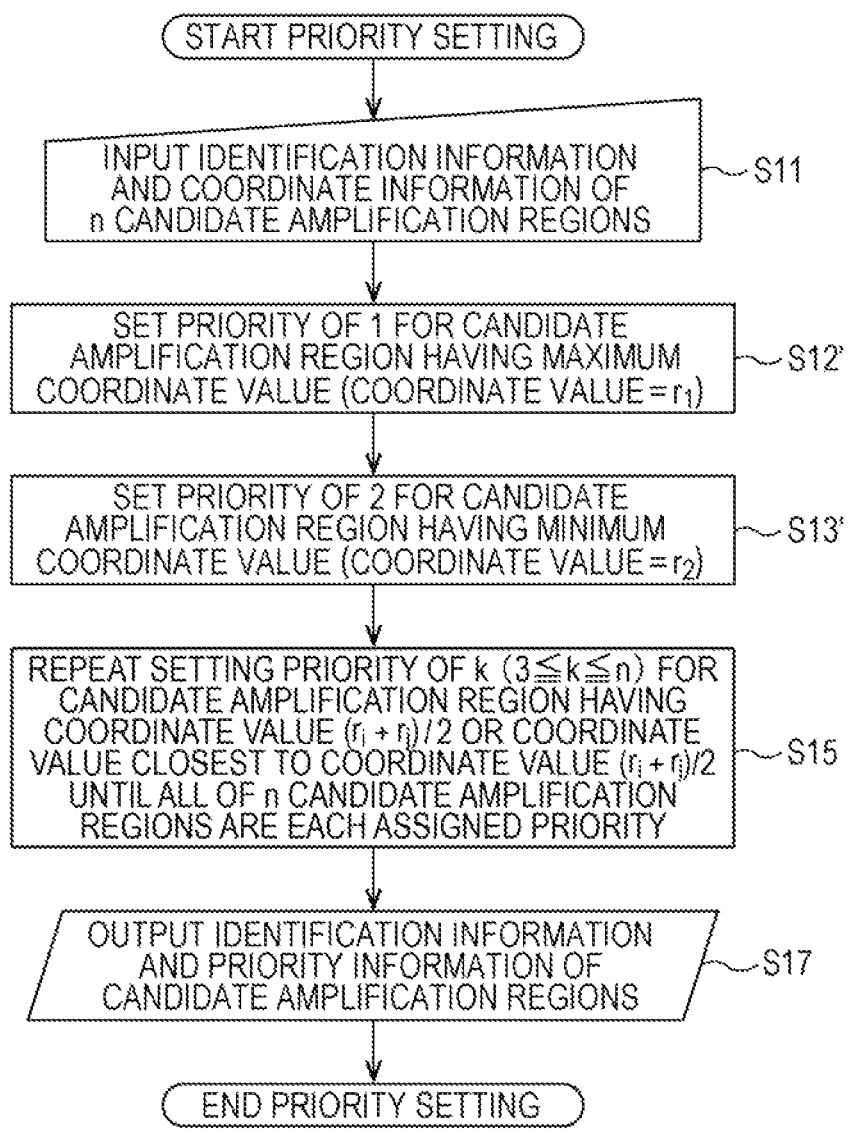
FIG. 3 is a flow diagram illustrating another embodiment of the priority setting method according to the first aspect of the present invention.

Alternatively, as illustrated in FIG. 3, priorities of 1 and 2 may be assigned in the following way.

A first priority setting step of, by the arithmetic means 11, searching for a candidate amplification region having a maximum coordinate value by using the identification information and coordinate information of the candidate amplification regions stored in the storage means 12, assigning priority information indicating a priority of 1, which corresponds to the highest priority, to the found candidate amplification region, and storing the priority information in the storage means 12 (S12' in FIG. 3).

A second priority setting step of, by the arithmetic means 11, searching for a candidate amplification region having a minimum coordinate value by using the identification information and coordinate information of the candidate amplification regions stored in the storage means 12, assigning priority information indicating a priority of 2, which corresponds to the second highest priority, to the found candidate amplification region, and storing the priority information in the storage means 12 (S13' in FIG. 3).

The first aspect of the present invention provides a method for designing primers for multiplex PCR, for assigning priorities to candidate amplification regions on same chromosomal DNA and designing primers for PCR amplifying the candidate amplification regions according to the priorities, in which the priorities are assigned using a priority assignment method including a candidate amplification region selection step, a first priority setting step, a second priority setting step, and a k-th priority setting step, the k-th priority setting step being repeated sequentially for k=3 to k=n.

<Candidate Amplification Region Selection Step>

The candidate amplification region selection step is a step of selecting n candidate amplification regions on the same chromosomal DNA. Identification information and coordinate information of the n candidate amplification regions are input (S11 in FIG. 2 and FIG. 3).

Here, n is an integer satisfying n≥3.

n is preferably 5 or more, more preferably 10 or more, even more preferably 50 or more, still more preferably 100 or more, and further more preferably 500 or more. Designing primers for multiplex PCR for more candidate amplification regions makes it easier to satisfy the necessary number of regions.

Note that even when all of the n candidate amplification regions are assigned priorities, it may not necessarily be possible to design primers for multiplex PCR for all the n candidate amplification regions, as described previously.

<First Priority Setting Step/Second Priority Setting Step>

In the n candidate amplification regions, a candidate amplification region having a minimum coordinate $r_{min}$ is represented by $R_{min}$, and a candidate amplification region having a maximum coordinate $r_{max}$ is represented by $R_{max}$.

<<First Priority Setting Step>>

The first priority setting step is a step of assigning a priority of 1, which corresponds to the highest priority, to one of the two candidate amplification regions, namely, the candidate amplification region $R_{min}$ and the candidate amplification region $R_{max}$ (S12 in FIG. 2; S12' in FIG. 3).

That is, the candidate amplification region $R_{min}$ is assigned a priority of 1, or the candidate amplification region $R_{max}$ is assigned a priority of 1.

<<Second Priority Setting Step>>

The second priority setting step is a step of assigning a priority of 2, which corresponds to the second highest priority, to the other of the two candidate amplification regions, namely, the candidate amplification region $R_{min}$ and the candidate amplification region $R_{max}$, except for the one assigned a priority of 1 (S13 in FIG. 2; S13' in FIG. 3).

That is, when the candidate amplification region $R_{min}$ is assigned a priority of 1 in the first priority setting step, the candidate amplification region $R_{max}$ is assigned a priority of 2. When the candidate amplification region $R_{max}$ is assigned a priority of 1 in the first priority setting step, the candidate amplification region $R_{min}$ is assigned a priority of 2.

<k-th Priority Setting Step>

In the k-th priority setting step, in a case where candidate amplification regions have already been assigned priorities from 1 through (k−1), with 1 being highest, a candidate amplification region having the coordinate value closest to coordinate $(r_i+r_j)/2$ of a midpoint of a candidate amplification region $R_i$ assigned a priority of i and a candidate amplification region $R_j$ assigned a priority of j is assigned a priority of k (S14 to S16 in FIG. 2 and FIG. 3). Here, $r_i$ and $r_j$ are coordinates of the candidate amplification region $R_i$ and the candidate amplification region respectively.

When two or more combinations of the candidate amplification region $R_i$ and the candidate amplification region $R_j$ are present, one combination may be randomly selected. Alternatively, a policy may be employed such that, for example, one of them having a smaller coordinate is given precedence or one of them having a larger coordinate is given precedence.

When two candidate amplification regions having the coordinate value closest to the coordinate $(r_i+r_j)/2$ are present, one region may be randomly selected. Alternatively, a policy may be employed such that, for example, one of them having a smaller coordinate is given precedence or one of them having a larger coordinate is given precedence.

Note that no candidate amplification region assigned a priority is present but at least one candidate amplification region yet to be assigned a priority is present between the candidate amplification region $R_i$ and the candidate amplification region $R_j$. Further, $R_1$ is $R_{min}$ or $R_{max}$ assigned a priority of 1 in the first priority setting step, and $R_2$ is $R_{min}$ or $R_{max}$ assigned a priority of 2 in the second priority setting step.

k is an integer satisfying 3≤k≤n.

i and j satisfy 1≤i≤k−1, 1≤j≤k−1, and i≠j.

$r_i$ and $r_j$ satisfy $r_{min} \le r_i \le r_{max}$, $r_{min} \le r_j \le r_{max}$, and $r_i \ne r_j$.

The k-th priority setting step is repeated sequentially for k=3 to k=n (S14 to S16 in FIG. 2 and FIG. 3).

When there is no candidate amplification region that can be assigned a priority, the setting of priorities is complete.

Further, the identification information and priority information of the candidate amplification regions are output (S17 in FIG. 2 and FIG. 3).

Note that priorities are set for the candidate amplification regions so that the priorities do not overlap.

Figure 7:
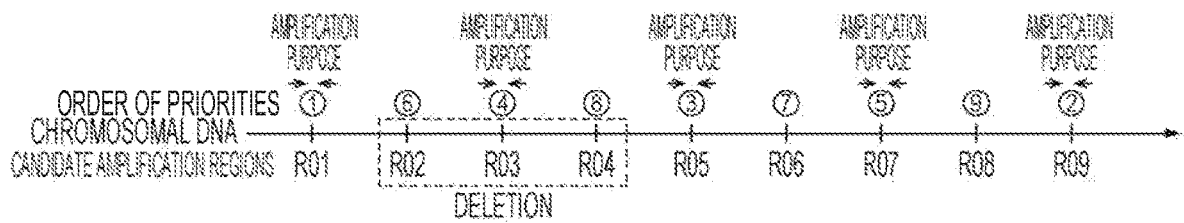
FIG. 7 is a conceptual diagram depicting the priority setting method according to the first aspect of the present invention, in which candidate amplification regions are assigned priorities dichotomically, and when primers are designed for R01, R03, R05, R07, and R09 to amplify five out of nine candidate amplification regions on the same chromosomal DNA and amplification is attempted, four sites, namely, R01, R05, R07, and R09, can be amplified due to the deletion of three sites corresponding to the candidate amplification regions R02, R03, and R04 on the chromosomal DNA.

<Description based on FIG. 7>

A specific description will be given with reference to FIG. 7.

In FIG. 7, for simplicity, nine candidate amplification regions, that is, candidate amplification regions R01 to R09, on the same chromosomal DNA are arranged with equal spacing in increasing order of coordinate from left to right.

(1) R01 having the smallest coordinate is assigned a priority of 1.

(2) R09 having the largest coordinate is assigned a priority of 2.

(3) R05 at the midpoint of R01 and R09 is assigned a priority of 3.

(4) R03 at the midpoint of R01 and R05 is assigned a priority of 4.

(5) R07 at the midpoint of R05 and R09 is assigned a priority of 5.

(6) R02 at the midpoint of R01 and R03 is assigned a priority of 6.

(7) R06 at the midpoint of R05 and R07 is assigned a priority of 7.

(8) R04 at the midpoint of R03 and R05 is assigned a priority of 8.

(9) R08 at the midpoint of R07 and R09 is assigned a priority of 9.

(10) Since there is no candidate amplification region yet to be assigned a priority, assignment of priority is complete.

<Advantageous Effects of First Aspect of Present Invention>

A description will be given, comparing FIG. 6 and FIG. 7.

Figure 6:
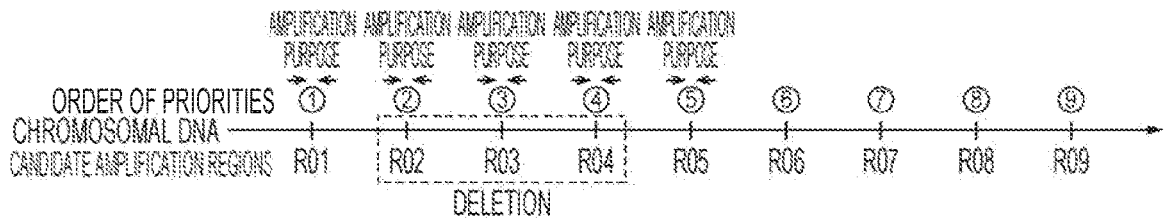
FIG. 6 is a conceptual diagram depicting a conventional priority setting method, in which candidate amplification regions are assigned priorities in order from smallest to largest in terms of coordinate, and when primers are designed for R01, R02, R03, R04, and R05 to amplify five out of nine candidate amplification regions on the same chromosomal DNA and amplification is attempted, only two sites, namely, R01 and R05, can be amplified due to the deletion of three sites corresponding to the candidate amplification regions R02, R03, and R04 on the chromosomal DNA.

In FIG. 6 and FIG. 7, the candidate amplification regions R01 to R09 are assigned priorities from 1 through 9, with 1 being highest.

Primers for amplifying, among the candidate amplification regions given priorities, five candidate amplification regions according to the priorities are produced.

In actual chromosomal DNA, R02, R03, and R04 are deleted.

Accordingly, in FIG. 6, primers are produced, and three (R02, R03, and R04) of the candidate amplification regions that are to be amplified are not successfully amplified. The number of candidate amplification regions that can be amplified is unlikely to meet the necessary number of regions.

In FIG. 7, however, primers are produced, and only one (R03) of the candidate amplification regions that are to be amplified is not successfully amplified. The number of candidate amplification regions that can be amplified is likely to meet the necessary number of regions.

[2. Second Aspect of Present Invention]

A second aspect of the present invention provides another solution to the first problem that amplification target regions for which amplification by multiplex PCR is not successful are generated and it is thus difficult to ensure a necessary number of regions for analysis such as genotyping. In the following, a description will be given with reference to FIG. 1, FIG. 4, and FIG. 5, as appropriate.

The second aspect of the present invention provides a method for designing primers for multiplex PCR, for assigning priorities to candidate amplification regions on same chromosomal DNA and designing primers for PCR amplifying the candidate amplification regions according to the priorities.

The priorities are assigned using a method for assigning priorities to candidate amplification regions on same chromosomal DNA, the method including the following steps.

Figure 4:
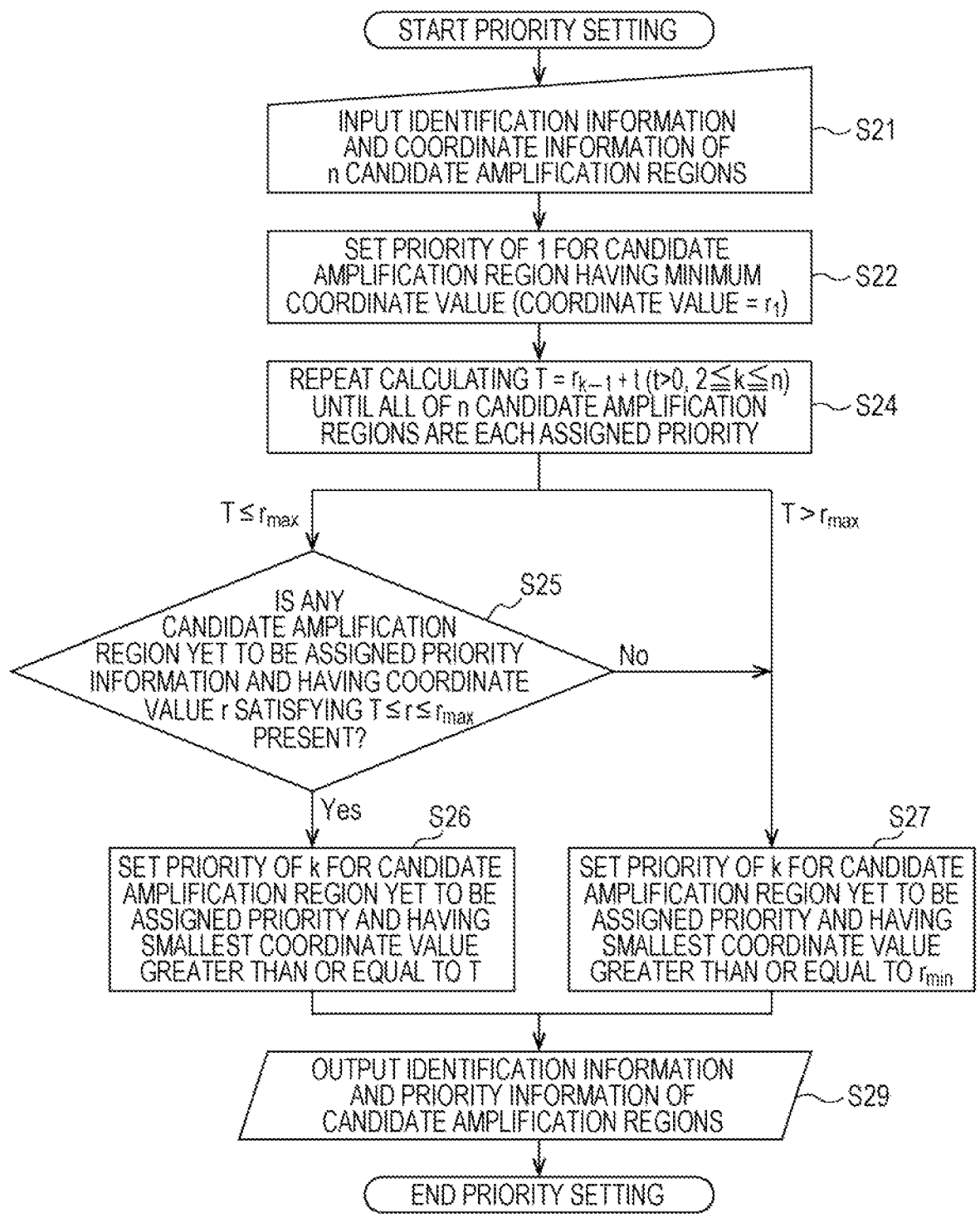
FIG. 4 is a flow diagram illustrating a priority setting method according to a second aspect of the present invention.

A step of inputting identification information and coordinate information of n candidate amplification regions on same chromosomal DNA via the input means 14 and storing the identification information and the coordinate information in the storage means 12 (S21 in FIG. 4).

A first priority setting step of, by the arithmetic means 11, searching for a candidate amplification region having a minimum coordinate value by using the identification information and coordinate information of the candidate amplification regions stored in the storage means 12, assigns priority information indicating a priority of 1, which corresponds to the highest priority, to the found candidate amplification region, and storing the priority information in the storage means 12 (S22 in FIG. 4).

A k-th priority setting step of, by the arithmetic means 11, searching for an identification name $R_{k-1}$ and a coordinate value $r_{k-1}$ of a candidate amplification region whose priority is k−1 by using the identification information, coordinate information, and priority information of the candidate amplification regions stored in the storage means 12, calculating $T=r_{k-1}+t$ (S24 in FIG. 4), when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if a candidate amplification region satisfying these conditions is present, assigning a priority of k to a candidate amplification region yet to be assigned priority information and having the smallest coordinate value greater than or equal to $r_{k-1}+t$ (S25 and S26 in FIG. 4), and storing the candidate amplification region assigned a priority of k in the storage means 12, when $T=r_{k-1}+t \leq r_{max}$ is satisfied, searching for a candidate amplification region yet to be assigned priority information and having a coordinate value greater than or equal to $r_{k-1}+t$ and less than or equal to $r_{max}$, if there is no candidate amplification region satisfying these conditions, assigning a priority of k to a candidate amplification region yet to be assigned priority information and having the smallest coordinate value greater than or equal to $r_{min}$ (S25 and S27 in FIG. 4), and storing the candidate amplification region assigned a priority of k in the storage means 12, and when $T=r_{k-1}+t > r_{max}$ is satisfied, assigning a priority of k to a candidate amplification region yet to be assigned a priority and having the smallest coordinate value greater than or equal to $r_{min}$ (S25 and S27 in FIG. 4), and storing the candidate amplification region assigned a priority of k in the storage means 12.

The k-th priority setting step is repeated for k=2 to n (S23 to S28 in FIG. 4).

Note that n is an integer satisfying 3≤n, k is an integer satisfying 2≤k≤n, t is a real number satisfying t>0, $r_{k-1} \neq r_k$ is satisfied, and $_{min}$ and $r_{max}$ are respectively a minimum coordinate value and a maximum coordinate value of the n candidate amplification regions.

Figure 5:
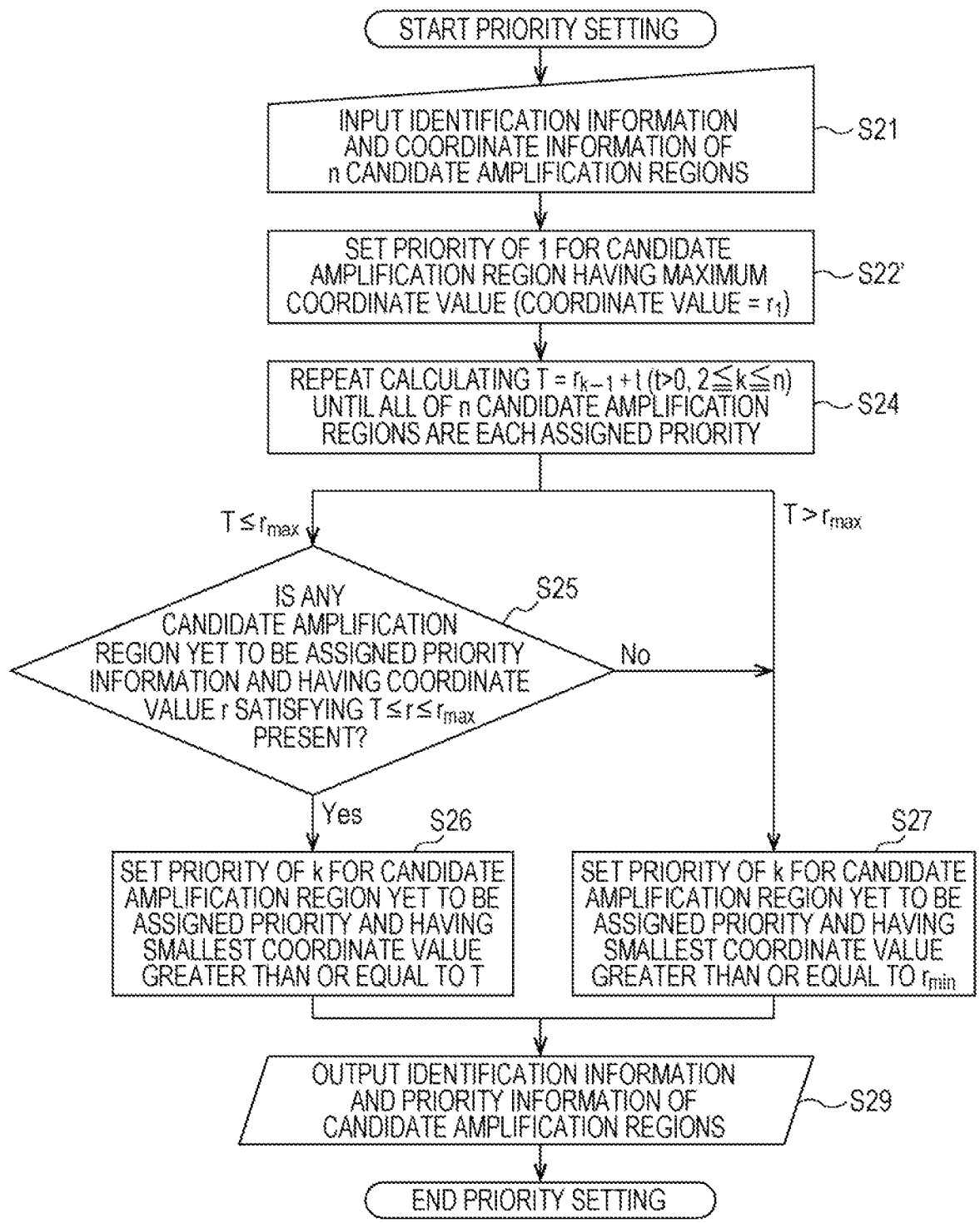
FIG. 5 is a flow diagram illustrating another embodiment of the priority setting method according to the second aspect of the present invention.

Alternatively, as illustrated in FIG. 5, a priority of 1 may be assigned in the following way.

A first priority setting step of, by the arithmetic means 11, searching for a candidate amplification region having a maximum coordinate value by using the identification information and coordinate information of the candidate amplification regions stored in the storage means 12, assigning priority information indicating a priority of 1, which corresponds to the highest priority, to the found candidate amplification region, and storing the priority information in the storage means 12 (S22' in FIG. 5).

The second aspect of the present invention provides a method for designing primers for multiplex PCR, for assigning priorities to candidate amplification regions on same chromosomal DNA and designing primers for PCR amplifying the candidate amplification regions according to the priorities, in which the priorities are assigned using a priority assignment method including a candidate amplification region selection step, a first priority setting step, and a k-th priority setting step, the k-th priority setting step being repeated sequentially for k=2 to k=n.

<Candidate Amplification Region Selection Step>

The candidate amplification region selection step is a step of selecting n candidate amplification regions on the same chromosomal DNA.

Here, n is an integer satisfying n≥3.

n is preferably 5 or more, more preferably 10 or more, even more preferably 50 or more, still more preferably 100 or more, and further more preferably 500 or more. Designing primers for multiplex PCR for more candidate amplification regions makes it easier to satisfy the necessary number of regions.

Note that even when all of the n candidate amplification regions are assigned priorities, it may not necessarily be possible to design primers for multiplex PCR for all the n candidate amplification regions, as described previously.

<First Priority Setting Step>

In the n candidate amplification regions, a candidate amplification region having a minimum coordinate $r_{min}$ is represented by $R_{min}$, and a candidate amplification region having a maximum coordinate $r_{max}$ is represented by $R_{max}$. Identification information and coordinate information of the n candidate amplification regions are input (S21 in FIG. 4 and FIG. 5).

The first priority setting step is a step of assigning a priority of 1, which corresponds to the highest priority, to a candidate amplification region $R_i$ located between the two candidate amplification regions described above, namely, the candidate amplification region $R_{min}$ and the candidate amplification region $R_{max}$, and having a coordinate $r_1$ satisfying $r_{min} \leq r_1 \leq r_{max}$ (S22 in FIG. 4; S22' in FIG. 5).

That is, the candidate amplification region $R_{min}$ may be assigned a priority of 1, the candidate amplification region $R_{max}$ may be assigned a priority of 1, or a candidate amplification region different front the candidate amplification region $R_{min}$ and the candidate amplification region may be assigned a priority of 1.

The coordinate $r_1$ of the candidate amplification region $R_1$ is not specifically limited so long as it satisfies $r_{min} \leq r_1 \leq r_{max}$, but preferably satisfies $r_1 = r_{min}$ or $r_1 = r_{max}$, and more preferably satisfies $r_1 = r_{min}$.

<k-th Priority Setting Step>

In the k-th priority setting step, in a case where candidate amplification regions have already been assigned priorities from 1 through (k−1), with 1 being highest, a candidate amplification region satisfying predetermined conditions is assigned a priority of k (S23 to S28 in FIG. 4 and FIG. 5).

A candidate amplification region satisfying the predetermined conditions is determined in the following way.

Consideration is given to the value "$T=r_{k-1}+t$", which is obtained by adding a threshold value t to the coordinate, $r_{k-1}$, of a candidate amplification region $R_{k-1}$ assigned a priority of (k−1). Here, t is a real number satisfying t>0, which is referred to sometimes as "threshold value" in the present invention.

Since the maximum coordinate value of the candidate amplification regions is presented by $r_{max}$, the following two cases (1) and (2) are obtained.

(1) A case where $T=r_{k-1}+t \leq r_{max}$ is satisfied.
(2) A case where $T=r_{k-1}+t > r_{max}$ is satisfied.

The case (1) is further divided into the following two cases (1)-1 and (1)-2 in accordance with whether a candidate amplification region yet to be assigned a priority is present between the coordinates $r_{k-1}+t$ and $r_{max}$.

(1)-1 A case where a candidate amplification region yet to be assigned a priority is present.
(1)-2 A case where a candidate amplification region yet to be assigned a priority is not present.

When (1)-1 is satisfied, a candidate amplification region yet to be assigned a priority and having the smallest coordinate value greater than or equal to $(r_{k-1}+t)$ is assigned a priority of k.

In this case, t denotes the distance between the candidate amplification region $R_{k-1}$ having a priority of (k−1) and a candidate amplification region $R_k$ having a priority of k. As t increases, the distance between $R_{k-1}$ and $R_k$ also increases, generally reducing the effect of $R_{k-1}$ and $R_k$ on each other.

When (1)-2 or (2) is satisfied, a candidate amplification region yet to be assigned a priority and having the smallest coordinate value greater than or equal to $r_{min}$ is assigned a priority of k.

k is an integer satisfying $2 \leq k \leq n$.

t is a real number satisfying t>0, which can be set as appropriate in accordance with the chromosomal DNA size, the coordinates of the candidate amplification regions, or the like, and is preferably 100,000 or more, more preferably 1,000,000 or more, and even more preferably 5,000,000 or more.

The k-th priority setting step is repeated sequentially for k=2 to k=n.

When there is no candidate amplification region that can be assigned a priority, the setting of priorities is complete.

Further, the identification information and priority information of the candidate amplification regions are output (S29 in FIG. 4 and FIG. 5).

Note that priorities are set for the candidate amplification regions so that the priorities do not overlap.

Figure 8:
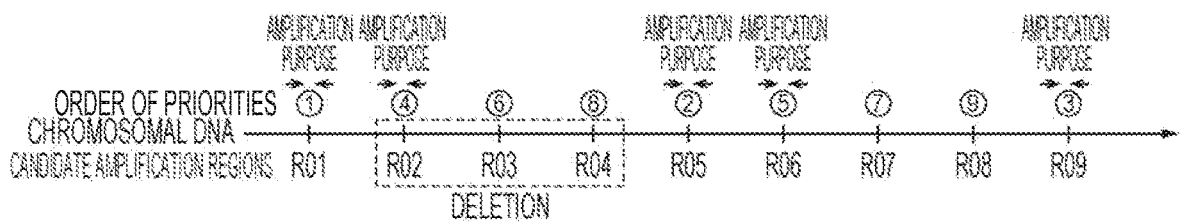
FIG. 8 is a conceptual diagram depicting the priority setting method according to the second aspect of the present invention, in which candidate amplification regions are assigned priorities based on a threshold distance value, and when primers are designed for R01, R02, R05, R06, and R09 to amplify five out of nine candidate amplification regions on the same chromosomal DNA and amplification is attempted, four sites, namely, R01, R05, R06, and R09, can be amplified due to the deletion of three sites corresponding to the candidate amplification regions R02, R03, and R04 on the chromosomal DNA.

<Description based on FIG. 8>

A specific description will be given with reference to FIG. 8.

In FIG. 8, for simplicity, nine candidate amplification regions, that is, candidate amplification regions R01 to R09, on the same chromosomal DNA are arranged with equal spacing in increasing order of coordinate from left to right. The spacing is assumed to be set to 1,000,000 (base pairs), and the threshold value t is assumed to be set to 4,000,000.

(1) R01 having the smallest coordinate is assigned a priority of 1.
(2) R05 having a coordinate equal to the coordinate of R01 plus 4,000,000 is assigned a priority of 2.
(3) R09 having a coordinate equal to the coordinate of R05 plus 4,000,000 is assigned a priority of 3.
(4) Since there is no candidate amplification region having a coordinate equal to the coordinate of R09 plus 4,000,000, a candidate amplification region yet to be assigned a priority and having the smallest coordinate greater than or equal to the coordinate of R01, that is, R02, is assigned a priority of 4.
(5) R06 having a coordinate equal to the coordinate of R02 plus 4,000,000 is assigned a priority of 5.
(6) Since there is no candidate amplification region having a coordinate equal to the coordinate of R06 plus 4,000,000, a candidate amplification region yet to be assigned a priority and having the smallest coordinate greater than or equal to the coordinate of R01, that is, R03, is assigned a priority of 6.
(7) R07 having a coordinate equal to the coordinate of R03 plus 4,000,000 is assigned a priority of 7.
(8) Since there is no candidate amplification region having a coordinate equal to the coordinate of R07 plus 4,000,000, a candidate amplification region yet to be assigned a priority and having the smallest coordinate greater than or equal to the coordinate of R01, that is, R04, is assigned a priority of 8.
(9) R08 having a coordinate equal to the coordinate of R04 plus 4,000,000 is assigned a priority of 9.
(10) Since there is no candidate amplification region yet to be assigned a priority, assignment of priority is complete.

<Advantageous Effects of Second Aspect of Present Invention>

A description will be given, comparing FIG. 6 and FIG. 8.

In FIG. 6 and FIG. 8, the candidate amplification regions R01 to R09 are assigned priorities from 1 through 9, with 1 being highest.

Primers for amplifying, among the candidate amplification regions given priorities, five candidate amplification regions according to the priorities are produced.

In actual chromosomal DNA, R02, R03, and R04 are deleted.

Accordingly, in FIG. 6, primers are produced, and three (R02, R03, and R04) of the candidate amplification regions that are to be amplified are not successfully amplified. The number of candidate amplification regions that can be amplified is unlikely to meet the necessary number of regions.

In FIG. 8, however, primers are produced, and only one (R02) of the candidate amplification regions that are to be amplified is not successfully amplified. The number of candidate amplification regions that can be amplified is likely to meet the necessary number of regions.

[3. Third Aspect of Present Invention]

A third aspect of the present invention provides still another solution to the first problem that amplification target regions for which amplification by multiplex PCR is not successful are generated and it is thus difficult to ensure a necessary number of regions for analysis such as genotyping. In the following, a description will be given with reference to FIG. 1, as appropriate.

The third aspect of the present invention provides a method for designing primers for multiplex PCR, for assigning priorities to candidate amplification regions on same chromosomal DNA and designing primers for PCR amplifying the candidate amplification regions according to the priorities.

The priorities are assigned using a method for assigning priorities to candidate amplification regions on same chromosomal DNA, the method including the following steps.

A step of inputting identification information and number-of-candidate-primer information of n candidate amplification regions on the same chromosomal DNA via the input means 14 and storing the identification information and the number-of-candidate-primer information in the storage means 12.

A k-th priority setting step of, by the arithmetic means 11, searching for a candidate amplification region including the k-th smallest number of candidate primers by using the identification information and number-of-candidate-primer information of the candidate amplification regions stored in the storage means 12, assigning priority information indicating a priority of k, which corresponds to the k-th highest priority, to the found candidate amplification region, and storing the priority information in the storage means 12.

The k-th priority setting step is repeated for k=1 to n, where n is an integer satisfying n≥2, and k is an integer satisfying 1≤k≤n.

Accordingly, the candidate amplification regions are assigned priorities such that a candidate amplification region having a smaller number of candidate primers that can be designed is assigned a higher priority.

The third aspect of the present invention provides a method for designing primers for multiplex PCR, for assigning priorities to candidate amplification regions on same chromosomal DNA and designing primers for PCR amplifying the candidate amplification regions according to the priorities, in which priorities are assigned to the candidate amplification regions such that a candidate amplification region having a smaller number of candidate primers that can be designed is assigned a higher priority.

A description will be given with reference to FIG. 9 and FIG. 10.

Figure 9:
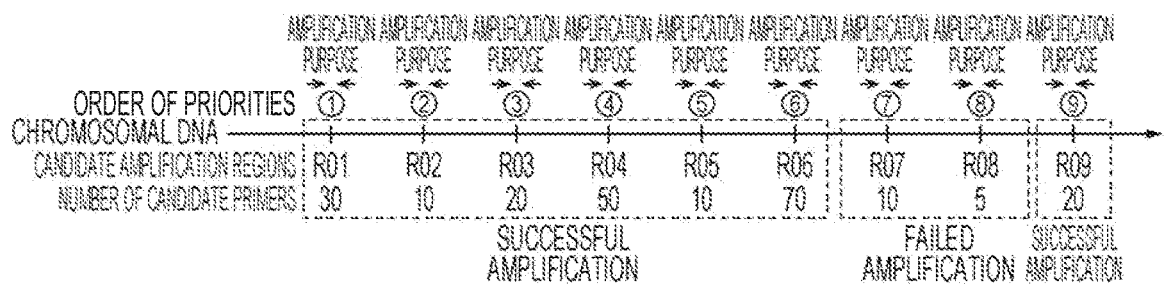
FIG. 9 is a conceptual diagram illustrating the conventional priority setting method, in which candidate amplification regions are assigned priorities in order from smallest to largest in terms of coordinate, and among nine candidate amplification regions R01 to R09 on the same chromosomal DNA, two sites, namely, R07 and R08, cannot be amplified.

The number of candidate primers for each of the candidate amplification regions R01 to R09 is as illustrated in FIG. 9 or FIG. 10. Note that the candidate primers are candidate primers having base sequences generated in "candidate primer base sequence generation" in a method for designing primers or the like, described below. In general, for each candidate amplification region, a plurality of primer pairs for amplifying the candidate amplification region are generated.

In FIG. 9, in accordance with a conventional method, candidate amplification regions are assigned priorities in order from smallest to largest in terms of coordinate. When priorities are assigned in coordinate order, the severity of complementarity conditions increases with an increase in the number of candidate amplification regions. Thus, in R07 and R08, which originally have a few candidates, the number of primer pairs employed as primers available for multiplex PCR is excessively small as a result of the examination of the probability of primer dimer formation with primers for amplifying the other candidate amplification regions. As a result, it is more likely that amplification will fail.

In FIG. 10, in accordance with the third aspect of the present invention, candidate amplification regions are assigned priorities in order of the number of candidate primers from lowest to highest. Assigning priorities in order of the number of candidate primers from lowest to highest causes an increase in the severity of complementarity conditions with an increase in the number of regions. However, since the number of candidates is originally large, the number of primer pairs employed as primers available for multiplex PCR is not excessively small as a result of the examination of the probability of primer dimer formation with primers for amplifying the other candidate amplification regions. As a result, it is more likely that amplification will be successful than in the conventional method.

[4. Fourth Aspect of Present Invention]

A fourth aspect of the present invention provides a solution to a problem that even if a necessary number of regions for analysis such as genotyping can be ensured, high accuracy is not achievable. In the following, a description will be given with reference to FIG. 1, as appropriate.

The fourth aspect of the present invention provides a method for designing primers for multiplex PCR, for assigning priorities to candidate amplification regions and designing primers for PCR amplifying the candidate amplification regions according to the priorities.

The priorities are assigned by using a method of assigning priorities to candidate amplification regions on chromosomal DNA, the method including the following steps.

A step of inputting identification information and variant frequency information of n candidate amplification regions on chromosomal DNA via the input means 14 and storing the identification information and the variant frequency information in the storage means 12.

A k-th priority setting step of, by the arithmetic means 11, calculating a variant frequency difference=$|0.5-VF_i|$ of a candidate amplification region having an identification name $R_i$ and a variant frequency $VF_i$ by using the identification information and variant frequency information of the candidate amplification regions stored in the storage means 12, searching for a candidate amplification region having the k-th smallest variant frequency difference, assigning priority information indicating a priority of k, which corresponds to the k-th highest priority, to the found candidate amplification region, and storing the priority information in the storage means 12.

The k-th priority setting step is repeated for k=1 to n, where n is an integer satisfying n≥2, and k is an integer satisfying 1≤k≤n.

Accordingly, the candidate amplification regions are assigned priorities such that a candidate amplification region in which a variant has a variant frequency closer to 0.5 is assigned a higher priority.

The fourth aspect of the present invention provides a method for designing primers for multiplex PCR, for assigning priorities to candidate amplification regions and designing primers for PCR amplifying the candidate amplification regions according to the priorities, in which the priorities are assigned to the candidate amplification regions such that a candidate amplification region in which a variant has a variant frequency closer to 0.5 is assigned a higher priority.

A description will be given with reference to FIG. 11 and FIG. 12.

For each of the candidate amplification regions R01 to R09, the V.F. (Variant Frequency) and ΔV.F, (the absolute value of the difference from a variant frequency of 0.5) of SNP (Single Nucleotide Polymorphism) are as illustrated in FIG. 11 and FIG. 12.

The candidate amplification regions R01 to R09 are assigned priorities from 1 through 9, with 1 being highest, primers are produced for the top five candidate amplification regions, amplification by multiplex PCR, SNP typing, and a maternity test are carried out to calculate the precision of the maternity test. The example illustrated in FIG. 11 provides higher precision and lower accuracy than the example illustrated in FIG. 12. In the example illustrated in FIG. 11, to reduce precision to increase accuracy, the number of SNP loci, or the number of candidate amplification regions, needs to be increased. In particular, for a minute amount of genomic DNA or the like with no redundancy, which is extracted from a single cell, it may be difficult to increase the number of regions to be simultaneously amplified by multiplex PCR or to increase the number of loci. Thus, it is desirable to achieve high accuracy with a smaller number of regions or loci.

[Method for Designing Primers for Multiplex PCR]

After the setting of priorities, which indicate the order in which primers are to be designed in candidate amplification regions, primers for PCR amplifying desired candidate amplification regions are designed by using a method for designing primers for multiplex PCR, described below.

<Method for Designing Primers for Multiplex PCR (1)>

In a method for designing primers for multiplex PCR (1) according to the present invention (hereinafter referred to sometimes simply as "design method (1)"), after priorities are set for candidate amplification regions, the following steps are performed.

(a) A target region selection step of selecting a target region from candidate amplification regions with set priorities in order of priority.

(b) A candidate primer base sequence generation step of generating at least one base sequence of a candidate primer for PCR amplifying the target region on the basis of each of base sequences of respective neighboring regions located at two ends of the target region on genomic DNA.

(c) A local alignment step of performing pairwise local alignment, for all combinations for selecting base sequences of two candidate primers from among base sequences of candidate primers generated in the candidate primer base sequence generation step, on two base sequences included in each of the combinations, under a condition in which partial sequences to be compared for the two base sequences include 3'-ends of the two base sequences, to determine local alignment scores.

(d) A first-stage selection step of performing first-stage selection of base sequences of candidate primers for PCR amplifying the target region on the basis of the local alignment scores.

(e) A global alignment step of performing pairwise global alignment, for all combinations for selecting base sequences of two candidate primers from among base sequences of candidate primers selected in the first-stage selection step, on base sequences having a preset sequence length and including 3'-ends of two base sequences included in each of the combinations, to determine global alignment scores.

(f) A second-stage selection step of performing second-stage selection of base sequences of candidate primers for PCR amplifying the target region on the basis of the global alignment scores.

(g) A primer employment step of employing, as base sequences of primers for PCR amplifying the target region, base sequences of candidate primers selected in both the first-stage selection step and the second-stage selection step.

Among the steps (a) to (g), both the steps (c) and (d) and both the steps (e) and (f) may be performed in any order or performed simultaneously. That is, the steps (e) and (f) may be performed after the steps (c) and (d) are performed, or the steps (c) and (d) may be performed after the steps (e) and (f) are performed. Alternatively, the steps (c) and (d) and the steps (e) and (f) may be performed in parallel.

If the steps (c) and (d) are performed after the steps (e) and (f) are performed, the steps (e) and (c) are preferably replaced with steps (e') and (c') below, respectively.

(e') A global alignment step of performing pairwise global alignment, for all combinations for selecting base sequences of two candidate primers from among base sequences of candidate primers generated in the candidate primer base sequence generation step, on base sequences having a preset sequence length and including 3'-ends of two base sequences included in each of the combinations, to determine global alignment scores.

(c') A local alignment step of performing pairwise local alignment, for all combinations for selecting base sequences of two candidate primers from among base sequences of candidate primers selected in the second-stage selection step, on two base sequences included in each of the combinations, under a condition in which partial sequences to be compared for the two base sequences include 3'-ends of the two base sequences, to determine local alignment scores.

Further, if the steps (c) and (d) and the steps (e) and (f) are performed in parallel, the step (e) is preferably replaced with step (e') below.

(e') A global alignment step of performing pairwise global alignment, for all combinations for selecting base sequences of two candidate primers from among base sequences of candidate primers generated in the candidate primer base sequence generation step, on base sequences having a preset sequence length and including 3'-ends of two base sequences included in each of the combinations, to determine global alignment scores.

<Method for Designing Primers for Multiplex PCR (2)>

In a method for designing primers for multiplex PCR (2) according to the present invention (hereinafter referred to sometimes simply as "design method (2)"), after priorities are set for candidate amplification regions, the following steps are performed.

($a_1$) A first step of target region selection for selecting the candidate amplification region having the highest priority as a first target region from among the candidate amplification regions with set priorities.

($b_1$) A first step of candidate primer base sequence generation for generating at least one base sequence of a candidate primer for PCR amplifying the first target region on the basis of each of base sequences of respective neighboring regions located at two ends of the first target region on genomic DNA.

($c_1$) A first step of local alignment for performing pairwise local alignment, for all combinations for selecting base sequences of two candidate primers from among base sequences of candidate primers generated in the first step of candidate primer base sequence generation, on two base sequences included in each of the combinations, under a condition in which partial sequences to be compared for the two base sequences include 3'-ends of the two base sequences, to determine local alignment scores.

($d_1$) A first step of first-stage selection for performing first-stage selection of base sequences of candidate primers for PCR amplifying the first target region on the basis of the local alignment scores.

($e_1$) A first step of global alignment for performing pairwise global alignment, for all combinations for selecting base sequences of two candidate primers from among base sequences of candidate primers selected in the first step of first-stage selection, on base sequences having a preset sequence length and including 3'-ends of two base sequences included in each of the combinations, to determine global alignment scores.

($f_1$) A first step of second-stage selection for performing second-stage selection of base sequences of candidate primers for PCR amplifying the first target region on the basis of the global alignment scores.

($g_1$) A first step of primer employment for employing, as base sequences of primers for PCR amplifying the first target region, base sequences of candidate primers selected in both the first step of first-stage selection and the first step of second-stage selection.

($a_2$) A second step of target region selection for selecting, as a second target region, a candidate amplification region having the highest priority from among candidate amplification regions that have not been selected among candidate amplification regions with set priorities.

($b_2$) A second step of candidate primer base sequence generation for generating at least one base sequence of a candidate primer for PCR amplifying the second target region on the basis of each of base sequences of respective neighboring regions located at two ends of the second target region on genomic DNA.

($c_2$) A second step of local alignment for performing pairwise local alignment, for all combinations for selecting base sequences of two candidate primers and all combinations for selecting a base sequence of one candidate primer and a base sequence of one primer that has already been employed from among base sequences of candidate primers generated in the second step of candidate primer base sequence generation and from among base sequences of primers that have already been employed, on two base sequences included in each of the combinations, under a condition in which partial sequences to be compared for the two base sequences include 3'-ends of the two base sequences, to determine local alignment scores.

($d_2$) A second step of first-stage selection for performing first-stage selection of base sequences of candidate primers for PCR amplifying the second target region on the basis of the local alignment scores.

($e_2$) A second step of global alignment for performing pairwise global alignment, for all combinations for selecting base sequences of two candidate primers and all combinations for selecting a base sequence of one candidate primer and a base sequence of one primer that has already been employed from among base sequences of candidate primers selected in the second step of first-stage selection and from among base sequences of primers that have already been employed, on base sequences having a preset sequence length and including 3'-ends of two base sequences included in each of the combinations, to determine global alignment scores.

($f_2$) A second step of second-stage selection for performing second-stage selection of base sequences of candidate primers for PCR amplifying the second target region on the basis of the global alignment scores.

($g_2$) A second step of primer employment for employing, as base sequences of primers for PCR amplifying the second target region, base sequences of candidate primers selected in both the second step of first-stage selection and the second step of second-stage selection.

Among the steps ($a_1$) to ($g_1$), both the steps ($c_1$) and ($d_1$) and both the steps ($e_1$) and ($f_1$) may be performed in any order or performed simultaneously. That is, the steps ($e_1$) and ($f_1$) may be performed after the steps ($c_1$) and ($d_1$) are performed, or the steps ($c_1$) and ($d_1$) may be performed after the steps ($e_1$) and ($f_1$) are performed. Alternatively, the steps ($c_1$) and ($d_1$) and the steps ($e_1$) and ($f_1$) may be performed in parallel.

If the steps ($c_1$) and ($d_1$) are performed after the steps ($e_1$) and ($f_1$) are performed, the steps ($c_1$) and ($c_1$) are preferably replaced with steps ($c_1'$) and ($c_1'$) below, respectively.

($e_1'$) A first step of global alignment for performing pairwise global alignment, for all combinations for selecting base sequences of two candidate primers from among base sequences of candidate primers generated in the first step of candidate primer base sequence generation, on base sequences having a preset sequence length and including 3'-ends of two base sequences included in each of the combinations, to determine global alignment scores.

($c_1'$) A first step of local alignment for performing pairwise local alignment, for all combinations for selecting base sequences of two candidate primers from among base sequences of candidate primers selected in the first step of second-stage selection, on two base sequences included in each of the combinations, under a condition in which partial sequences to be compared for the two base sequences include 3'-ends of the two base sequences, to determine local alignment scores.

Further, if the steps ($c_1$) and ($d_1$) and the steps ($e_1$) and ($f_1$) are performed in parallel, the step ($e_1$) is preferably replaced with step ($e_1'$) below.

($e_1'$) A first step of global alignment for performing pairwise global alignment, for all combinations for selecting base sequences of two candidate primers from among base sequences of candidate primers generated in the first step of candidate primer base sequence generation, on base sequences having a preset sequence length and including 3'-ends of two base sequences included in each of the combinations, to determine global alignment scores.

Among the steps ($a_2$) to ($g_2$), both the steps ($c_2$) and ($d_2$) and both the steps ($e_2$) and ($f_2$) may be performed in any order or performed simultaneously. That is, the steps ($e_2$) and ($f_2$) may be performed after the steps ($c_2$) and ($d_2$) are performed, or the steps ($c_2$) and ($d_2$) may be performed after the steps ($e_2$) and ($f_2$) are performed. Alternatively, the steps ($c_2$) and ($d_2$) and the steps ($e_2$) and ($f_2$) may be performed in parallel.

If the steps ($c_2$) and ($d_2$) are performed after the steps ($e_2$) and ($f_2$) are performed, the steps ($e_2$) and ($c_2$) are preferably replaced with steps ($e_2'$) and ($c_2'$) below, respectively.

($e_2'$) A second step of global alignment for performing pairwise global alignment, for all combinations for selecting base sequences of two candidate primers and all combinations for selecting a base sequence of one candidate primer and a base sequence of one primer that has already been employed from among base sequences of candidate primers generated in the second step of candidate primer base sequence generation and from among base sequences of primers that have already been employed, on base sequences having a preset sequence length and including 3'-ends of two base sequences included in each of the combinations, to determine global alignment scores.

($c_2'$) A second step of local alignment for performing pairwise local alignment, for all combinations for selecting base sequences of two candidate primers and all combinations for selecting a base sequence of one candidate primer and a base sequence of one primer that has already been employed from among base sequences of candidate primers selected in the second step of second-stage selection and from among base sequences of primers that have already been employed, on two base sequences included in each of the combinations, under a condition in which partial sequences to be compared for the two base sequences include 3'-ends of the two base sequences, to determine local alignment scores.

Further, if the steps ($c_2$) and ($d_2$) and the steps ($e_2$) and ($f_2$) are performed in parallel, the step ($e_2$) is preferably replaced with step ($e_2$') below.

($e_2$') A second step of global alignment for performing pairwise global alignment, for all combinations for selecting base sequences of two candidate primers and all combinations for selecting a base sequence of one candidate primer and a base sequence of one primer that has already been employed from among base sequences of candidate primers generated in the second step of candidate primer base sequence generation and from among base sequences of primers that have already been employed, on base sequences having a preset sequence length and including 3'-ends of two base sequences included in each of the combinations, to determine global alignment scores.

Further, when the candidate amplification region includes three or more candidate amplification regions and when base sequences of primers for PCR amplifying third and subsequent target regions that have not yet been selected from the three or more regions of interest are employed, the steps ($a_2$) to ($g_2$) are repeated for each of the third and subsequent target regions.

<Method for Designing Primers for Multiplex PCR (3)>

In a method for designing primers for multiplex PCR (3) according to the present invention (hereinafter referred to sometimes simply as "design method (3)"), after priorities are set for candidate amplification regions, the following steps are performed. In its modification, priorities are set for candidate amplification regions after a plurality-of-candidate-primer-base-sequence generation step (b-0) is performed and before a first local alignment step (c-1) is performed, and then a first local alignment step (c-1) and subsequent steps are performed.

(a-0) A plurality-of-target-region selection step of selecting a plurality of target regions from candidate amplification regions with set priorities in order from highest to lowest in terms of priority.

(b-0) A plurality-of-candidate-primer-base-sequence generation step of generating at least one base sequence of a candidate primer for PCR amplifying each of the plurality of target regions on the basis of each of base sequences of respective neighboring regions located at two ends of each of the plurality of target regions on genomic DNA.

After the plurality-of-candidate-primer-base-sequence generation step (b-0) is performed, priorities, which indicate the order in which primers are to be designed in candidate amplification regions, are set. After setting of priorities, the first local alignment step (c-1) and subsequent steps are performed.

Note that priorities may be set before the plurality-of-target-region selection step (a-0) is performed instead of after the plurality-of-candidate-primer-base-sequence generation step (b-0) is performed.

(c-1) A first local alignment step of performing pairwise local alignment, for all combinations for selecting base sequences of two candidate primers from among base sequences of candidate primers for PCR amplifying a first target region having the highest priority among base sequences of candidate primers generated in the plurality-of-candidate-primer-base-sequence generation step, on two base sequences included in each of the combinations, under a condition in which partial sequences to be compared for the two base sequences include 3'-ends of the two base sequences, to determine local alignment scores.

(d-1) A first first-stage selection step of performing first-stage selection of base sequences of candidate primers for PCR amplifying the first target region on the basis of the local alignment scores.

(e-1) A first global alignment step of performing pairwise global alignment, for all combinations for selecting base sequences of two candidate primers from among base sequences of candidate primers selected in the first first-stage selection step, on base sequences having a preset sequence length and including 3'-ends of two base sequences included in each of the combinations, to determine global alignment scores.

(f-1) A first second-stage selection step of performing second-stage selection of base sequences of candidate primers for PCR amplifying the first target region on the basis of the global alignment scores.

(g-1) A first primer employment step of employing, as base sequences of primers for PCR amplifying the first target region, base sequences of candidate primers selected in both the first first-stage selection step and the first second-stage selection step.

(c-2) A second local alignment step of performing pairwise local alignment, for all combinations for selecting base sequences of two candidate primers and all combinations for selecting a base sequence of one candidate primer and a base sequence of one primer that has already been employed from among base sequences of candidate primers for PCR amplifying a second target region having a priority of 2 among base sequences of candidate primers generated in the plurality-of-candidate-primer-base-sequence generation step and from among base sequences of primers that have already been employed, on two base sequences included in each of the combinations, under a condition in which partial sequences to be compared for the two base sequences include 3'-ends of the two base sequences, to determine local alignment scores.

(d-2) A second first-stage selection step of performing first-stage selection of base sequences of candidate primers for PCR amplifying the second target region on the basis of the local alignment scores.

(e-2) A second global alignment step of performing pairwise global alignment, for all combinations for selecting base sequences of two candidate primers and all combinations for selecting a base sequence of one candidate primer and a base sequence of one primer that has already been employed from among base sequences of candidate primers selected in the second first-stage selection step and from among base sequences of primers that have already been employed, on base sequences having a preset sequence length and including 3'-ends of two base sequences included in each of the combinations, to determine global alignment scores.

(f-2) A second second-stage selection step of performing second-stage selection of base sequences of candidate primers for PCR amplifying the second target region on the basis of the global alignment scores.

(g-2) A second primer employment step of employing, as base sequences of primers for PCR amplifying the second target region, base sequences of candidate primers selected in both the second first-stage selection step and the second second-stage selection step.

Among the steps (c-1) to (g-1), both the steps (c-1) and (d-1) and both the steps (e-1) and (f-1) may be performed in any order or performed simultaneously. That is, the steps (e-1) and (f-1) may be performed after the steps (c-1) and (d-1) are performed, or the steps (c-1) and (d-1) may be performed after the steps (e-1) and (f-1) are performed. Alternatively, the steps (c-1) and (d-1) and the steps (e-1) and (f-1) may be performed in parallel.

If the steps (c-1) and (d-1) are performed after the steps (e-1) and (f-1) are performed, the steps (e-1) and (c-1) are preferably replaced with steps (e'-1) and (c'-1), respectively.

(e'-1) A first global alignment step of performing pairwise global alignment, for all combinations for selecting base sequences of two candidate primers from among base sequences of candidate primers for PCR amplifying a first target region having the highest priority among base sequences of candidate primers generated in the plurality-of-candidate-primer-base-sequence generation step, on base sequences having a preset sequence length and including 3'-ends of two base sequences included in each of the combinations, to determine global alignment scores.

(e'-1) A first local alignment step of performing pairwise local alignment, for all combinations for selecting base sequences of two candidate primer's from among base sequences of candidate primers selected in the first second-stage selection step, on two base sequences included in each of the combinations, under a condition in which partial sequences to be compared for the two base sequences include 3'-ends of the two base sequences, to determine local alignment scores.

Further, if the steps (c-1) and (d-1) and the steps (e-1) and (f-1) are performed in parallel, the step (e-1) is preferably replaced with step (e'-1) below.

(e'-1) A first global alignment step of performing pairwise global alignment, for all combinations for selecting base sequences of two candidate primers from among base sequences of candidate primers for PCR amplifying a first target region having the highest priority among base sequences of candidate primers generated in the plurality-of-candidate-primer-base-sequence generation step, on base sequences having a preset sequence length and including 3'-ends of two base sequences included in each of the combinations, to determine global alignment scores.

Among the steps (c-2) to (g-2), both the steps (c-2) and (d-2) and both the steps (e-2) and (f-2) may be performed in any order or performed simultaneously. That is, the steps (e-2) and (f-2) may be performed after the steps (c-2) and (d-2) are performed, or the steps (c-2) and (d-2) may be performed after the steps (c-2) and (f-2) are performed. Alternatively, the steps (c-1) and (d-1) and the steps (e-1) and (f-1) may be performed in parallel.

If the steps (c-2) and (d-2) are performed after the steps (e-2) and (f-2) are performed, the steps (e-2) and (c-2) are preferably replaced with steps (e'-2) and (c'-2) below, respectively.

(e'-2) A second global alignment step of performing pairwise global alignment, for all combinations for selecting base sequences of two candidate primers and all combinations for selecting a base sequence of one candidate primer and a base sequence of one primer that has already been employed from among base sequences of candidate primers for PCR amplifying a second target region having a priority of 2 among base sequences of candidate primers generated in the plurality-of-candidate-primer-base-sequence generation step and from among base sequences of primers that have already been employed, on base sequences having a preset sequence length and including 3'-ends of two base sequences included in each of the combinations, to determine global alignment scores.

(c'-2) A second local alignment step of performing pairwise local alignment, for all combinations for selecting base sequences of two candidate primers and all combinations for selecting a base sequence of one candidate primer and a base sequence of one primer that has already been employed from among base sequences of candidate primers selected in the second second-stage selection step and from among base sequences of primers that have already been employed, on two base sequences included in each of the combinations, under a condition in which partial sequences to be compared for the two base sequences include 3'-ends of the two base sequences, to determine local alignment scores.

Further, if the steps (c-2) and (d-2) and the steps (e-2) and (f-2) performed in parallel, the step (e-2) is preferably replaced with step (e'-2) below.

(e'-2) A second global alignment step of performing pairwise global alignment, for all combinations for selecting base sequences of two candidate primers and all combinations for selecting a base sequence of one candidate primer and a base sequence of one primer that has already been employed from among base sequences of candidate primers for PCR amplifying a second target region having a priority of 2 among base sequences of candidate primers generated in the plurality-of-candidate-primer-base-sequence generation step and from among base sequences of primers that have already been employed, on base sequences having a preset sequence length and including 3'-ends of two base sequences included in each of the combinations, to determine global alignment scores.

Further, when the candidate amplification regions include three or more candidate amplification regions, when three or more target regions are selected in the plurality-of-target-region selection step, when base sequences of candidate primers for PCR amplifying each of the three or more target regions are generated in the plurality-of-candidate-primer-base-sequence generation step, and when base sequences of primers for PCR amplifying third and subsequent target regions having the third and subsequent highest priorities are employed, the steps from the second local alignment step to the second primer employment step are repeated for the third and subsequent target regions.

<Description of Steps>

The steps of the methods for designing primers for multiplex PCR (1) to (3) according to the present invention will be described.

<<Priority Setting Step>>

(Design Method (1): Priority Setting Step S100)

Figure 13:
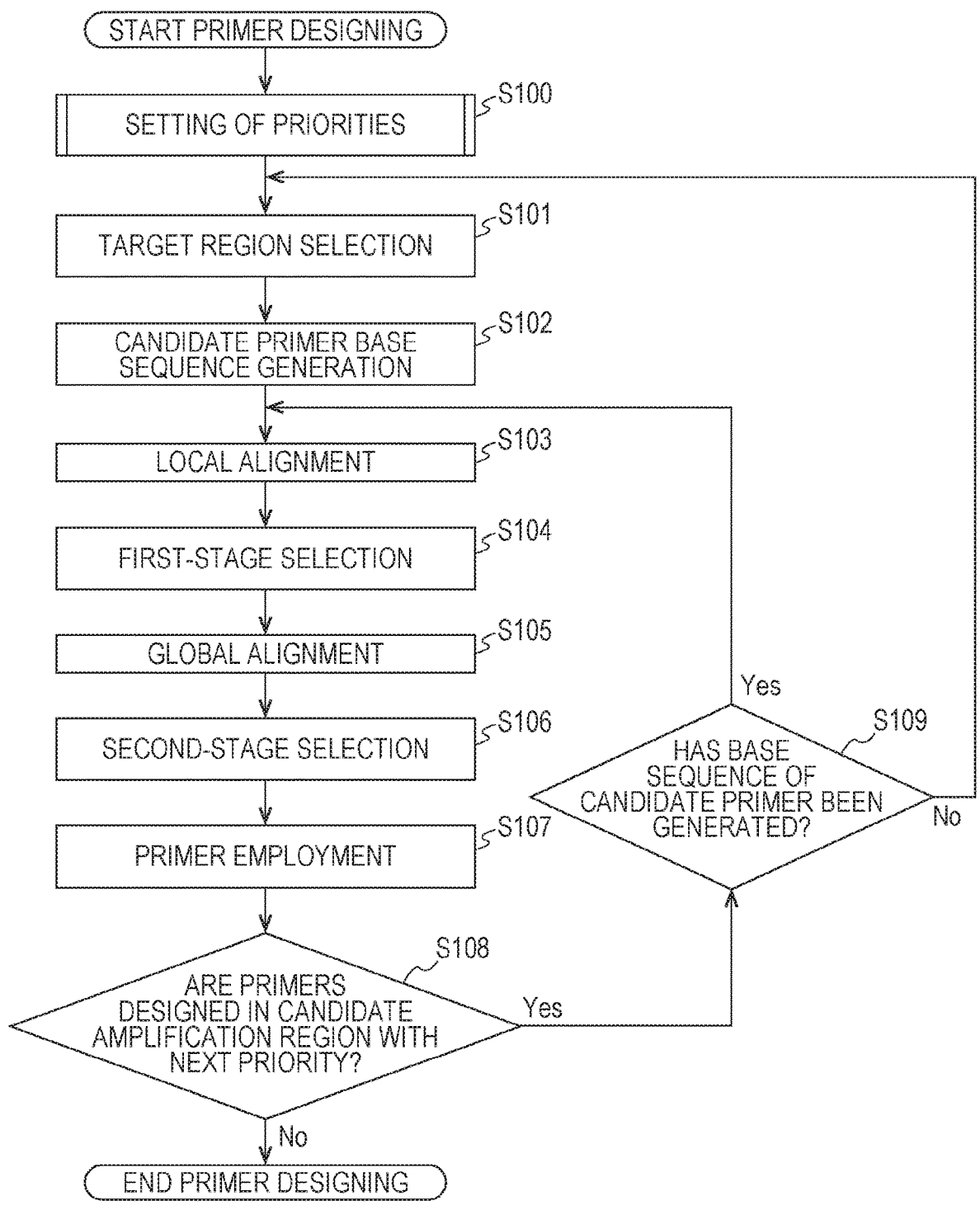
FIG. 13 is a flow diagram describing a method for designing primers for multiplex PCR (1), in which after priorities of candidate amplification regions are set, target regions are selected in order of priority to design primers.

In FIG. 13, this step is represented as "setting of priorities".

Priorities of candidate amplification regions are set in accordance with the priority setting method according to the present invention.

Figure 14:
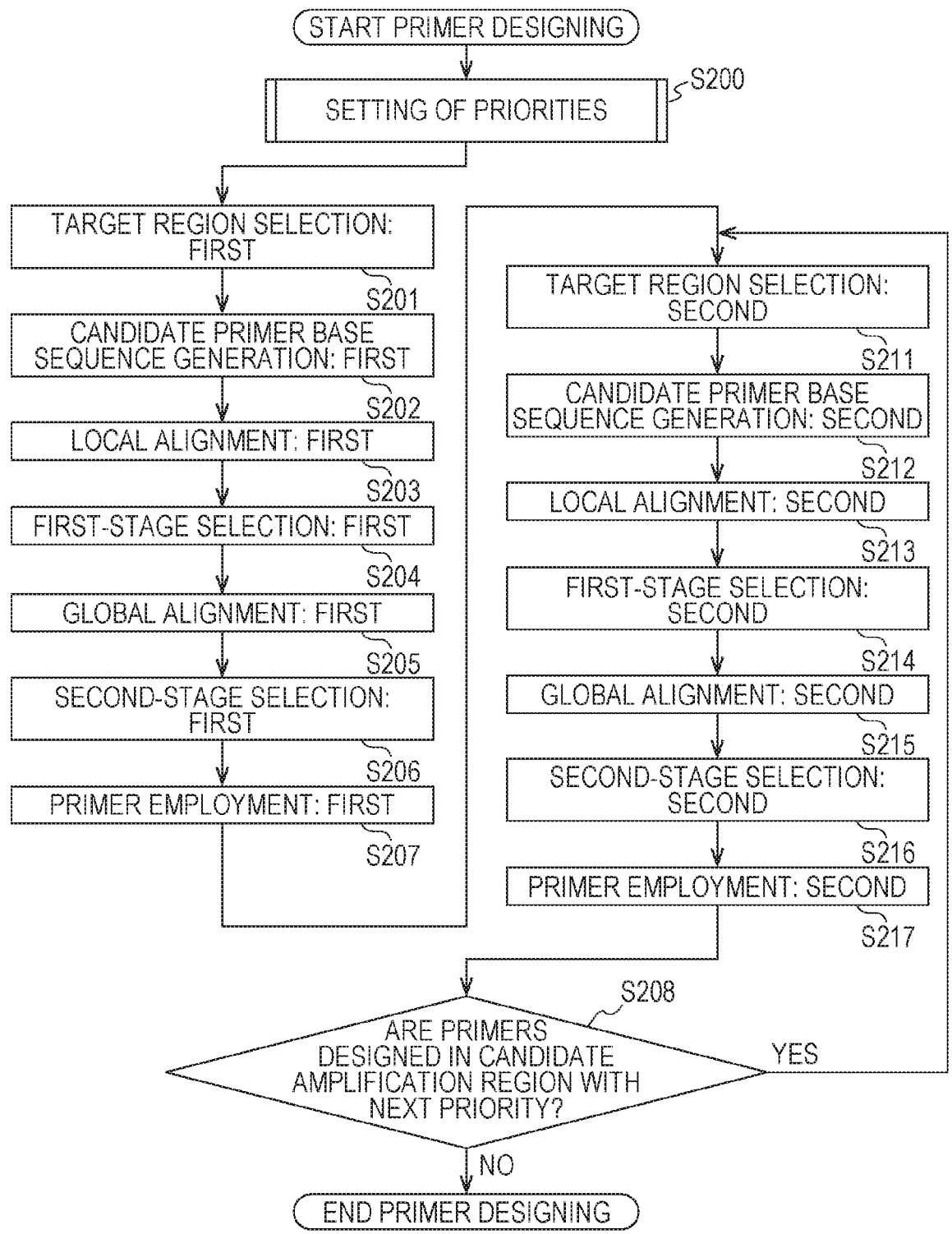
FIG. 14 is a flow diagram describing a method for designing primers for multiplex PCR (2), in which after priorities of candidate amplification regions are set, target regions are selected in order of priority to design primers.

(Design Method (2): Priority Setting Step S200)

in FIG. 14, this step is represented as "setting of priorities".

Priorities of candidate amplification regions are set in accordance with the priority setting method according to the present invention.

(Design Method (3): Priority Setting Step S300)

Figure 15:
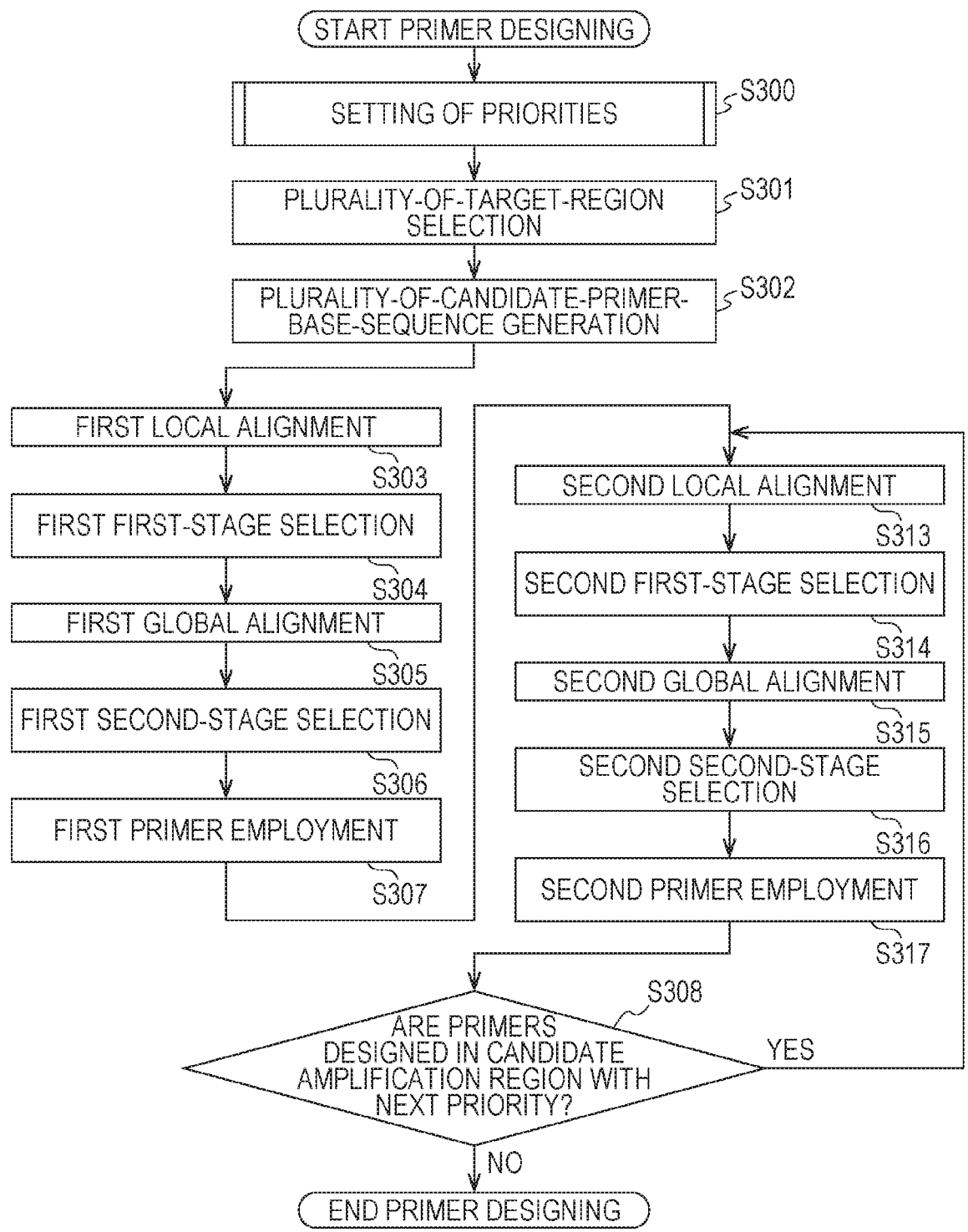
FIG. 15 is a flow diagram describing a method for designing primers for multiplex PCR (3) according to the present invention, in which a target region is selected after priorities of candidate amplification regions are set, base sequences of candidate primers are designed, and then steps are performed in order of priority to design primers.
Figure 16:
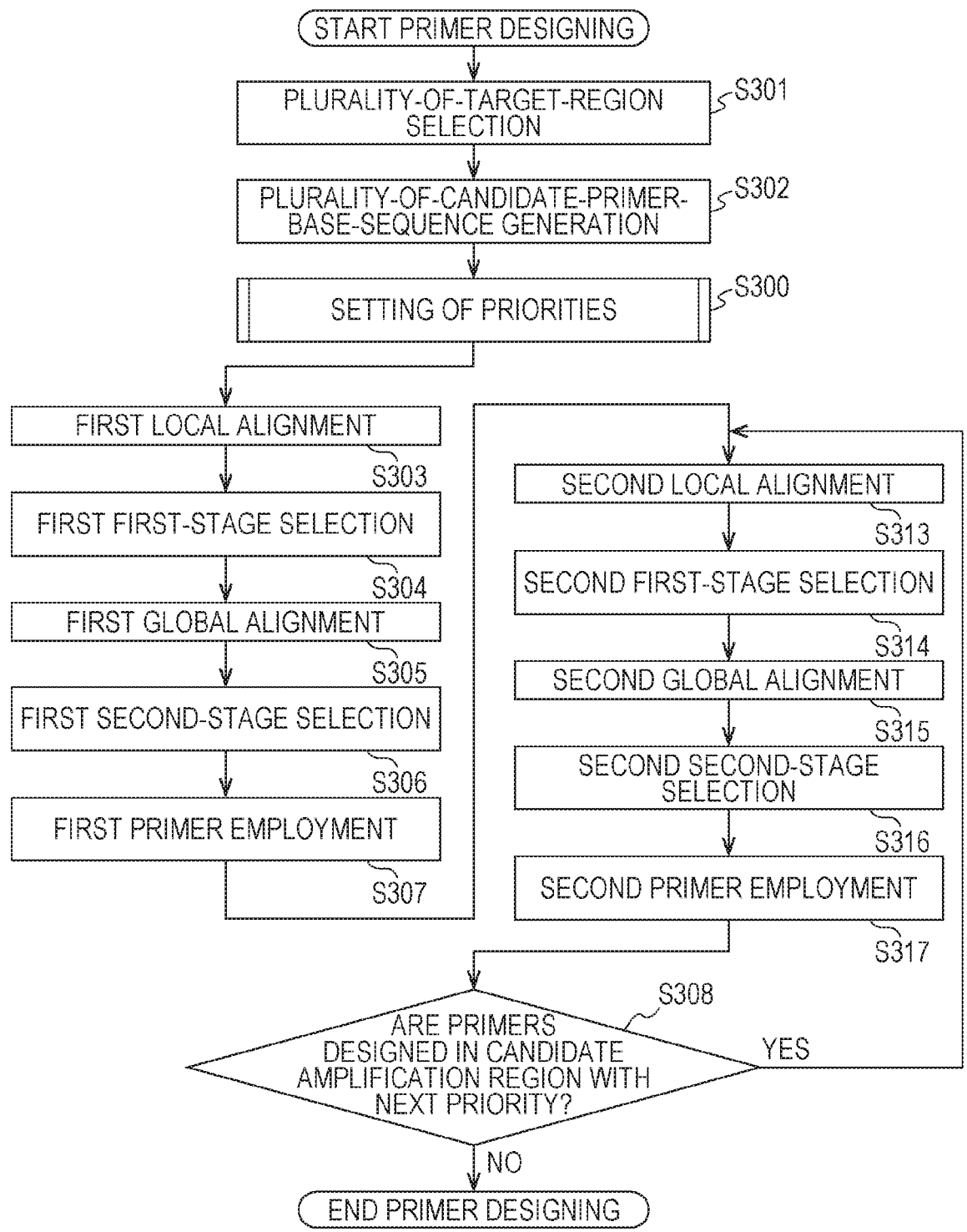
FIG. 16 is a flow diagram describing a modification of the method for designing primers for multiplex PCR (3) according to the present invention, in which priorities are set for candidate amplification regions after a target region is selected and base sequences of candidate primers are designed, and then the subsequent steps are performed in order of priority to design primers.

In FIG. 15 and FIG. 16, this step is represented as "setting of priorities".

Priorities of candidate amplification regions are set in accordance with the priority setting method according to the present invention.

<<Target Region Selection Step>>

As used herein, target region selection step S101 (FIG. 13), first step of target region selection S201 and second step of target region selection S211 (FIG. 14), and plurality-of-target-region selection step S301 (FIG. 15 and FIG. 16) are collectively referred to sometimes simply as "target region selection step".

(Design Method (1): Target Region Selection Step S101)

In FIG. 13, this step is represented as "target region selection".

In the design method (1), the target region selection step (a) is a step of selecting a target region from candidate amplification regions with set priorities in order of priority.

(Design Method (2): First Step of Target Region Selection S201 and Second Step of Target Region Selection S211)

In FIG. 14, these steps are represented as "target region selection: first" and "target region selection: second".

In the design method (2), the first step of target region selection ($a_1$) is a step of selecting a candidate amplification region having the highest priority as a first target region from among the candidate amplification regions with set priorities, and the second step of target region selection ($a_2$) is a step of selecting, as a second target region, a candidate amplification region having the highest priority from among candidate amplification regions that have not been selected among candidate amplification regions with set priorities.

In the design method (2), candidate amplification regions are selected one by one in order of priority.

(Design Method (3): Plurality-of-Target-Region Selection Step S301)

In FIG. 15 and FIG. 16, this step is represented as "plurality-of-target-region selection".

In the design method (3) and its modification, the plurality-of-target-region selection step (a-0) is a step of selecting a plurality of target regions from candidate amplification regions with set priorities in order from highest to lowest in terms of priority.

In the design method (3) and its modification, a plurality of candidate amplification regions are selected in order of priority. Preferably, all the candidate amplification regions with set priorities are selected.

<<Candidate Primer Base Sequence Generation Step>>

As used herein, candidate primer base sequence generation step S102 (FIG. 13), first step of candidate primer base sequence generation S202 and second step of candidate primer base sequence generation S212 (FIG. 14), and plurality-of-candidate-primer-base-sequence generation step S302 (FIG. 15 and FIG. 16) are collectively referred to sometimes simply as "candidate primer base sequence generation".

(Design Method (1): Candidate Primer Base Sequence Generation Step S102)

In FIG. 13, this step is represented as "candidate primer base sequence generation".

In the design method (1), the candidate primer base sequence generation step (b) is a step of generating at least one base sequence of a candidate primer for PCR amplifying a target region on the basis of each of base sequences of respective neighboring regions located at two ends of the target region on genomic DNA.

(Design Method (2): First Step of Candidate Primer Base Sequence Generation S202 and Second Step of Candidate Primer Base Sequence Generation S212)

In FIG. 14, these steps are represented as "candidate primer base sequence generation: first" and "candidate primer base sequence generation: second".

In the design method (2), the first step of candidate primer base sequence generation ($b_1$) is a step of generating at least one base sequence of a candidate primer for PCR amplifying a first target region on the basis of each of base sequences of respective neighboring regions located at two ends of the first target region on genomic DNA, and the second step of candidate primer base sequence generation ($b_2$) is a step of generating at least one base sequence of a candidate primer for PCR amplifying a second target region on the basis of each of base sequences of respective neighboring regions located at two ends of the second target region on genomic DNA.

In the design method (2), the generation of a base sequence of a candidate primer, the selection of a candidate primer, and the employment of a primer are performed for one target region, and similar steps are repeated for the next target region.

(Design Method (3): Plurality-of-Candidate-Primer-Base-Sequence Generation Step S302)

In FIG. 15 and FIG. 16, this step is represented as "plurality-of-candidate-primer-base-sequence generation".

In the design method (3) and its modification, the plurality-of-candidate-primer-base-sequence generation step (b-0) is a step of generating at least one base sequence of a candidate primer for PCR amplifying each of a plurality of target regions on the basis of each of base sequences of respective neighboring regions located at two ends of each of the plurality of target regions on genomic DNA.

In the design method (3) and its modification, base sequences of candidate primers are generated for all the plurality of target regions, and selection and employment are repeated in the subsequent steps.

(Neighboring Region)

Respective neighboring regions located at two ends of a target region are collectively referred to as regions outside the 5'-end of the target region and regions outside the 3'-end of the target region. The area inside the target region is not included in the neighboring regions.

The length of a neighboring region is not specifically limited, and is preferably less than or equal to a length that allows extension of a neighboring region by PCR, and more preferably less than or equal to the upper limit of the length of the DNA fragment to be amplified. In particular, the length of a neighboring region is preferably a length that facilitates application of concentration selection and/or sequence reading. The length of a neighboring region may be changed as appropriate in accordance with the type or the like of enzyme (DNA polymerase) to be used in PCR. The specific length of a neighboring region is preferably about 20 to 500 bases, more preferably about 20 to 300 bases, even more preferably about 20 to 200 bases, and still more preferably about 50 to 200 bases.

(Primer Design Parameter)

In addition, to generate a base sequence of a candidate primer, careful attention is required to the same points as those in a common method for designing primers, such as primer length, GC content (corresponding to the total mole percentage of guanine (G) and cytosine (C) in all nucleic acid bases), melting temperature (temperature at which 50% of double-stranded DNA is dissociated into single-stranded DNA, referred to sometimes as "Tm value", from Melting Temperature, in "° C."), and sequence deviation.

Primer Length

The primer length (number of nucleotides) is not specifically limited, and is preferably 15-mer to 45-mer, more preferably 20-mer to 45-mer, and even more preferably 20-mer to 30-mer. A primer length in this range facilitates the designing of a primer excellent in specificity and amplification efficiency.

Primer GC Content

The primer GC content is not specifically limited, and is preferably 40 mol % to 60 mol %, and more preferably 45 mol % to 55 mol %. A GC content in this range is less likely to cause a problem of a reduction in specificity and amplification efficiency due to a high-order structure.

Primer Tm Value

The primer Tm value is not specifically limited, and is preferably in a range of 50° C. to 65° C., and more preferably in a range of 55° C. to 65° C.

In a primer pair and a primer set, the difference between the Tm values of primers is set to preferably 5° C. or less, and more preferably 3° C. or less.

The Tm value can be calculated using software such as OLIGO Primer Analysis Software (manufactured by Molecular Biology Insights Inc.) or Primer3 (http://www-genome.wi.mit.edu/ftp/distribution/software/).

Alternatively, the Tm value can be calculated in accordance with the formula below based on the numbers of A's, T's, G's, and C's (represented as nA, nT, nG, and nC, respectively) in a base sequence of a primer.

$$\text{Tm value}(°\text{ C.})=2(nA+nT)+4(nC+nG)$$

The method for calculating the Tm value is not limited to those described above, and the Tm value can be calculated using any of various well-known methods.

Base Deviation of Primer

A base sequence of a candidate primer is preferably a sequence having entirely no deviation of bases. For example, it is desirable to avoid a partially GC-rich sequence and a partially AT-rich sequence.

It is also desirable to avoid consecutive T's and/or C's (polypyrimidine) and consecutive A's and/or G's (polypurine).

3'-End of Primer

For the 3'-end base sequence, furthermore, it is preferable to avoid a GC-rich sequence or an AT-rich sequence. The base at the 3'-end is preferably, but is not limited to, G or C.

<<Specificity Check Step>>

A specificity check step may be performed (not illustrated) to evaluate the specificity of a base sequence of a candidate primer on the basis of the sequence complementarity of a base sequence of each candidate primer, which is generated in "candidate primer base sequence generation", to chromosomal DNA.

A specificity check may be performed in the following manner. Local alignment is performed between a base sequence of chromosomal DNA and a base sequence of a candidate primer, and it can be evaluated that the base sequence of the candidate primer has low complementarity to the genomic DNA and has high specificity when the local alignment score is less than a preset value. It is desirable to perform local alignment also on complementary strands of the chromosomal DNA. This is because whereas a primer is single-stranded DNA, chromosomal DNA is double-stranded. Alternatively, instead of a base sequence of a candidate primer, a base sequence complementary thereto may be used.

In addition, homology search may be performed against a genomic DNA base sequence database by using a base sequence of a candidate primer as a query sequence. Examples of a homology search tool include BLAST (Basic Local Alignment Search Tool) (Altschul, S. A., four others, "Basic Local Alignment Search Tool", Journal of Molecular Biology, October 1990, Vol. 215, pp. 403-410) and FASTA (Pearson, W. R., one other, "Improved tools for biological sequence comparison", Proceedings of the National Academy of Sciences of the United States of America, the National Academy of Sciences of the United States of America, April 1988, Vol. 85, pp. 2444-2448). As a result of homology search, local alignment can be obtained.

Threshold values for scores and local alignment scores are not specifically limited and may be set as appropriate in accordance with the length of a base sequence of a candidate primer and/or PCR conditions or the like. When a homology search tool is used, specified values for the homology search tool may be used.

For example, as the score, match (complementary base)=+1, mismatch (non-complementary base)=−1, and indel (insertion and/or deletion)=−3 may be employed, and the threshold value may be set to +15.

If a base sequence of a candidate primer has complementarity to a base sequence at an unexpected position on chromosomal DNA and has low specificity, an artifact, rather than a target region, may be amplified in PCR performed using a primer of the base sequence, and the artifact is thus removed.

<<Local Alignment Step>>

As used herein, local alignment step S103 (FIG. 1), first step of local alignment S203 and second step of local alignment S213 (FIG. 14), and first local alignment step S303 and second local alignment step S313 (FIG. 15 and FIG. 16) are collectively referred to sometimes simply as "local alignment step".

(Design Method (1): Local Alignment Step S103)

In FIG. 13, this step is represented as "local alignment".

In the design method (1), the local alignment step (c) is a step of performing pairwise local alignment, for all combinations for selecting base sequences of two candidate primers from among base sequences of candidate primers generated in the candidate primer base sequence generation step, on two base sequences included in each of the combinations, under a condition in which partial sequences to be compared for the two base sequences include 3'-ends of the two base sequences, to determine local alignment scores.

(Design Method (2): First Step of Local Alignment S203 and Second Step of Local Alignment S213)

In FIG. 14, these steps are represented as "local alignment: first" and "local alignment: second".

In the design method (2), the first step of local alignment ($c_1$) is a step of performing pairwise local alignment, for all combinations for selecting base sequences of two candidate primers from among base sequences of candidate primers generated in the first step of candidate primer base sequence generation, on two base sequences included in each of the combinations, under a condition in which partial sequences to be compared for the two base sequences include 3'-ends of the two base sequences, to determine local alignment scores, and the second step of local alignment ($c_2$) is a step of performing pairwise local alignment, for all combinations for selecting base sequences of two candidate primers and all combinations for selecting a base sequence of one candidate primer and a base sequence of one primer that has already been employed from among base sequences of candidate primers generated in the second step of candidate primer base sequence generation and from among base sequences of primers that have already been employed, on two base sequences included in each of the combinations, under a condition in which partial sequences to be compared for the two base sequences include 3'-ends of the two base sequences, to determine local alignment scores.

(Design Method (3): First Local Alignment Step S303 and Second Local Alignment Step S313)

In FIG. 15 and FIG. 16, these steps are represented as "first local alignment" and "second local alignment".

In the design method (3) and its modification, the first local alignment step (c-1) is a step of performing pairwise local alignment, for all combinations for selecting base sequences of two candidate primers from among base sequences of candidate primers for PCR amplifying a first target region having the highest priority among base sequences of candidate primers generated in the plurality-of-candidate-primer-base-sequence generation step, on two base sequences included in each of the combinations, under a condition in which partial sequences to be compared for the two base sequences include 3'-ends of the two base sequences, to determine local alignment scores, and the second local alignment step (c-2) is a step of performing pairwise local alignment, for all combinations for selecting base sequences of two candidate primers and all combinations for selecting a base sequence of one candidate primer and a base sequence of one primer that has already been employed from among base sequences of candidate primers for PCR amplifying a second target region having a priority of 2 among base sequences of candidate primers generated in the plurality-of-candidate-primer-base-sequence generation step and from among base sequences of primers that have already been employed, on two base sequences included in each of the combinations, under a condition in which partial sequences to be compared for the two base sequences include 3'-ends of the two base sequences, to determine local alignment scores.

(Method for Local Alignment)

A combination of base sequences to be subjected to local alignment may be a combination selected with allowed overlap or a combination selected without allowed overlap. However, if the probability of primer dimer formation between primers having the same base sequence has not yet been evaluated, it is preferable to use a combination selected with allowed overlap.

The total number of combinations is given by "$_xH_2 =\,_{x+1}C_2=(x+1)!/2(x-1)!$" when combinations are selected with allowed overlap, and is given by "$_xC_2=x(x-1)/2$" when combinations are selected without allowed overlap, where x denotes the total number of base sequences to be subjected to local alignment.

Local alignment is alignment to be performed on partial sequences and allows local examination of high complementarity fragments.

In the present invention, however, unlike typical local alignment performed on base sequences, local alignment is performed under the condition that "partial sequences to be compared include the 3'-ends of the base sequences", so that partial sequences to be compared include the 3'-ends of both the base sequences.

In the present invention, furthermore, in a preferred aspect, local alignment is performed under the condition that "partial sequences to be compared include the 3'-ends of the base sequences", that is, the condition that "partial sequences to be compared take into account only alignment that starts at the 3'-end of one of the sequences and ends at the 3'-end of the other sequence", so that partial sequences to be compared include the 3'-ends of both the base sequences.

Note that in local alignment, a gap may be inserted. The gap refers to an insertion and/or deletion (indel) of a base.

In local alignment, furthermore, a match is determined when bases in a base sequence pair are complementary to each other, and a mismatch is determined when bases in a base sequence pair are not complementary to each other.

Alignment is performed such that a score is set for each of a match, a mismatch, and an indel and the total score is maximum. The scores may be set as appropriate. For example, scores may be set as in Table 1 below. In Table 1, "−" indicates a gap (insertion and/or deletion (indel)).

TABLE 1

|   | A  | T  | G  | C  | —  |
|---|----|----|----|----|----|
| A | −1 | +1 | −1 | −1 | −1 |
| T | +1 | −1 | −1 | −1 | −1 |
| G | −1 | −1 | −1 | +1 | −1 |
| C | −1 | −1 | +1 | −1 | −1 |
| — | −1 | −1 | −1 | −1 |    |

"—": gap(indel)

For example, consideration is given to local alignment of base sequences with SEQ ID NOs: 1 and 2 given in Table 2 below. Here, scores are assumed to be given in Table 1.

TABLE 2

|             | Base sequence (5'→3')  |
|-------------|------------------------|
| SEQ ID NO: 1 | TAGCCGGATGTGGGAGATGG  |
| SEQ ID NO: 2 | CCAGCATTGGAAAGATCTGG  |

Figure 20:
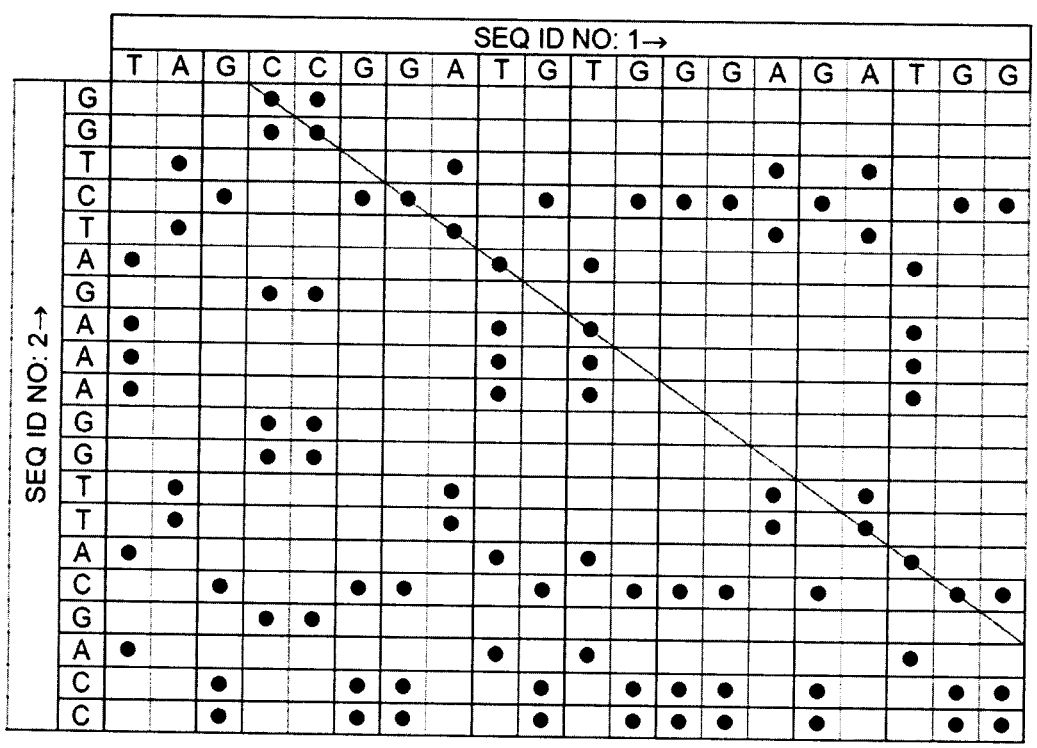
FIG. 20 is a dot matrix generated from the base sequences with SEQ ID NOs: 1 and 2. Specifically, the base sequence with SEQ ID NO: 1 is arranged from left to right in a 5' to 3' direction, and the base sequence with SEQ ID NO: 2 is arranged from bottom to top in a 5' to 3' direction, with grids of complementary bases filled with "•" to obtain a dot matrix.

A dot matrix given in FIG. 20 is generated from the base sequences with SEQ ID NOs: 1 and 2. Specifically, the base sequence with SEQ ID NO: 1 is arranged from left to right in a 5' to 3' direction, and the base sequence with SEQ ID NO: 2 is arranged from bottom to top in a 5' to 3' direction, with grids of complementary bases filled with "•" to obtain a dot matrix given in FIG. 20.

The dot matrix given in FIG. 20 yields alignment of partial sequences (pairwise alignment) as given in Table 4 below (see a portion indicated by the diagonal line in FIG. 20). In Table 4, a match is denoted by "|" and a mismatch is denoted by ":".

TABLE 4

| Partial sequence from SEQ ID NO: 1 | 5'-CCGGATGTGGGAGATGG-3' |
|---|---|
|   | ||:|||:|::::|||: |
| Partial sequence from SEQ ID NO: 2 | 3'-GGTCTAGAAAGGTTACG-5' |

This (pairwise) alignment includes nine matches, eight mismatches, and no indel (gap).

Thus, the local alignment score based on this (pairwise) alignment is given by $(+1)\times9+(-1)\times8+(-1)\times0=+1$.

Note that the alignment (pairwise alignment) may be obtained using, instead of the dot matrix method exemplified herein, the dynamic programming method, the word method, or any of various other methods.

<<First-Stage Selection Step>>

As used herein, first-stage selection step S104 (FIG. 13), first step of first-stage selection S204 and second step of first-stage selection S214 (FIG. 14), and first first-stage selection step S304 and second first-stage selection step S314 (FIG. 15 and FIG. 16) are collectively referred to sometimes simply as "first-stage selection step".

(Design Method (1): First-Stage Selection Step S104)

In FIG. 13, this step is represented as "first-stage selection".

In the design method (1), the first-stage selection step (d) is a step of performing first-stage selection of base sequences of candidate primers for PCR amplifying the target region on the basis of the local alignment scores.

(Design Method (2): First Step of First-Stage Selection S204 and Second Step of First-Stage Selection S214)

In FIG. 14, these steps are represented as "first-stage selection: first" and "first-stage selection: second".

In the design method (2), the first step of first-stage selection ($d_1$) is a step of performing first-stage selection of base sequences of candidate primers for PCR amplifying the first target region on the basis of the local alignment scores, and the second step of first-stage selection ($d_2$) is a step of performing first-stage selection of base sequences of candidate primers for PCR amplifying the second target region on the basis of the local alignment scores.

(Design Method (3): First First-Stage Selection Step S304 and Second First-Stage Selection Step S314)

In FIG. 15 and FIG. 16, these steps are represented as "first first-stage selection" and "second first-stage selection".

In the design method (3) and its modification, the first first-stage selection step (d-1) is a step of performing first-stage selection of base sequences of candidate primers for PCR amplifying the first target region on the basis of the local alignment scores, and the second first-stage selection step (d-2) is a step of performing first-stage selection of base sequences of candidate primers for PCR amplifying the second target region on the basis of the local alignment scores.

(Method for First-Stage Selection)

A threshold value for local alignment scores (referred to also as "first threshold value") is set in advance.

If a local alignment score is less than the first threshold value, the combination of two base sequences is determined to have low probability of dimer formation, and then the subsequent step is performed.

On the other hand, if a local alignment score is not less than the first threshold value, the combination of two base sequences is determined to have high probability of primer dimer formation, and no farther steps are performed for the combination.

The first threshold value is not specifically limited and can be set as appropriate. For example, the first threshold value may be set in accordance with PCR conditions such as the amount of genomic DNA that is a template for polymerase chain reaction.

Here, consideration is given to a case where the first threshold value is set to "+3" in the example provided in the "local alignment step" described above.

In the above example, the local alignment score is "+1" and is less than the first threshold value, that is, "+3". Thus, the combination of the base sequences with SEQ ID NOs: 1 and 2 can be determined to have low probability of primer dimer formation.

Note that this step is performed on all the combinations for which local alignment scores are calculated in the local alignment step S103, the first step of local alignment S203, the second step of local alignment S213, the first local alignment step S303, or the second local alignment step S313.

<<Global Alignment Step>>

As used herein, global alignment step S105 (FIG. 13), first step of global alignment S205 and second step of global alignment S215 (FIG. 14), and first global alignment step S305 and second global alignment step S315 (FIG. 15 and FIG. 16) are collectively referred to sometimes simply as "global alignment step".

(Design Method (1): Global Alignment Step S105)

In FIG. 13, this step is represented as "global alignment".

In the design method (1), the global alignment step (e) is a step of performing pairwise global alignment, for all combinations for selecting base sequences of two candidate primers from among base sequences of candidate primers selected in the first-stage selection step, on base sequences having a preset sequence length and including 3'-ends of two base sequences included in each of the combinations, to determine global alignment scores.

(Design Method (2): First Step of Global Alignment S205 and Second Step of Global Alignment S215)

In FIG. 14, these steps are represented as "global alignment: first" and "global alignment: second".

In the design method (2), the first step of global alignment ($e_1$) is a step of performing pairwise global alignment, for all combinations for selecting base sequences of two candidate primers from among base sequences of candidate primers selected in the first step of first-stage selection, on base sequences having a preset sequence length and including 3'-ends of two base sequences included in each of the combinations, to determine global alignment scores, and the second step of global alignment ($e_2$) is a step of performing pairwise global alignment, for all combinations for selecting base sequences of two candidate primers and all combinations for selecting a base sequence of one candidate primer and a base sequence of one primer that has already been employed from among base sequences of candidate primers selected in the second step of first-stage selection and from among base sequences of primers that have already been employed, on base sequences having a preset sequence length and including 3'-ends of two base sequences included in each of the combinations, to determine global alignment scores.

(Design Method (3): First Global Alignment Step S305 and Second Global Alignment Step S315)

In FIG. 15 and FIG. 16, these steps are represented as "first global alignment" and "second global alignment".

In the design method (3) and its modification, the first global alignment step (e-1) is a step of performing pairwise global alignment, for all combinations for selecting base sequences of two candidate primers from among base sequences of candidate primers selected in the first first-stage selection step, on base sequences having a preset sequence length and including 3'-ends of two base sequences included in each of the combinations, to determine global alignment scores, and the second global alignment step (e-2) is a step of performing pairwise global alignment, for all combinations for selecting base sequences of two candidate primers and all combinations for selecting a base sequence of one candidate primer and a base sequence of one primer that has already been employed from among base sequences of candidate primers selected in the second first-stage selection step and from among base sequences of primers that have already been employed, on base sequences having a preset sequence length and including 3'-ends of two base sequences included in each of the combinations, to determine global alignment scores.

(Method for Global Alignment)

A global alignment score is determined by extracting two primers from the group consisting of all the candidate primers generated in "candidate primer base sequence generation" (when the "local alignment step" and the "first-stage selection step" are performed previously, if there is a combination of candidate primers having local alignment scores less than the first threshold value, all the candidate primers included in the combination) and all the primers that have already been employed (only when there is present a primer that has already been employed) and by performing pairwise global alignment on base sequences having a preset sequence length and including the 3'-ends of the extracted primers.

A combination of base sequences to be subjected to global alignment may be a combination selected with allowed overlap or a combination selected without allowed overlap. However, if the probability of primer dimer formation between primers having the same base sequence has not yet been evaluated, it is preferable to use a combination selected with allowed overlap.

The total number of combinations is given by "$_xH_2=_{x+1}C_2=(x+1)!/2(x-1)!$" when combinations are selected with allowed overlap, and is given by "$_xC_2=x(x-1)/2$" when combinations are selected without allowed overlap, where x denotes the total number of base sequences to be subjected to global alignment.

Global alignment is alignment to be performed on "entire sequences" and allows examination of the complementarity of the entire sequences.

As used here, the "entire sequence" refers to the entire base sequence having a preset sequence length and including the 3'-end of a base sequence of a candidate primer.

Note that in global alignment, a gap may be inserted. The gap refers to an insertion and/or deletion (indel) of a base.

In global alignment, furthermore, a match is determined when bases in a base sequence pair are complementary to each other, and a mismatch is determined when bases in a base sequence pair are not complementary to each other.

Alignment is performed such that a score is set for each of a match, a mismatch, and an indel and the total score is maximum. The scores may be set as appropriate. For example, scores may be set as in Table 1 above. In Table 1, "–" indicates a gap (insertion and/or deletion (indel)).

For example, consideration is given to global alignment of, for base sequences with SEQ ID NOs: 1 and 2 given in Table 5 below, three bases (indicated by capital letters) at the 3'-end of each base sequence. Here, scores are assumed to be given in Table 1.

TABLE 5

| | Base sequence (5'→3') |
|---|---|
| SEQ ID NO: 1 | tagccggatgtgggagaTGG |
| SEQ ID NO: 2 | ccagcattggaaagatcTGG |

Global alignment is performed on three bases (indicated by capital letters) at the 3'-end of the base sequence with SEQ ID NO: 1 and three bases (indicated by capital letters) at the 3'-end of the base sequence with SEQ ID NO: 2 so as to obtain a maximum score, yielding alignment (pairwise alignment) given in Table 6 below. In Table 6, a mismatch is denoted by ":".

TABLE 6

| | |
|---|---|
| Three bases at 3'-end of SEQ ID NO: 1 | 5'-TGG-3' |
| | ::: |
| Three bases at 3'-end of SEQ ID NO: 2 | 3'-GGT-5' |

This (pairwise) alignment includes 3 mismatches and no match and indel (gap).

Thus, the global alignment score based on this (pairwise) alignment is given by $(+1)\times 0+(-1)\times 3+(-1)\times 0=-3$.

Note that alignment (pairwise alignment) may be obtained using the dot matrix method, the dynamic programming method, the word method, or any of various other methods.

<<Second-Stage Selection Step>>

As used herein, second-stage selection step S106 (FIG. 13), first step of second-stage selection S206 and second step of second-stage selection S216 (FIG. 14), and first second-stage selection step S306 and second second-stage selection step S316 (FIG. 15 and FIG. 16) are collectively referred to sometimes simply as "second-stage selection step".

(Design Method (1): Second-Stage Selection Step S106)

In FIG. 13, this step is represented as "second-stage selection".

In the design method (1), the second-stage selection step (f) is a step of performing second-stage selection of base sequences of candidate primers for PCR amplifying the target region on the basis of the global alignment scores.

(Design Method (2): First Step of Second-Stage Selection S206 and Second Step of Second-Stage Selection S216)

In FIG. 14, these steps are represented as "second-stage selection: first" and "second-stage selection: second".

In the design method (2), the first step of second-stage selection ($f_1$) is a step of performing second-stage selection of base sequences of candidate primers for PCR amplifying the first target region on the basis of the global alignment scores, and the second step of second-stage selection ($f_2$) is a step of performing second-stage selection of base sequences of candidate primers for PCR amplifying the second target region on the basis of the global alignment scores.

(Design Method (3): First Second-Stage Selection Step S306 and Second Second-stage Selection Step S316)

In FIG. 15 and FIG. 16, these steps are represented as "first second-stage selection" and "second second-stage selection".

In the design method (3) and its modification, the first second-stage selection step (f-1) is a step of performing second-stage selection of base sequences of candidate primers for PCR amplifying the first target region on the basis of the global alignment scores, and the second second-stage selection step (f-2) is a step of performing second-stage selection of base sequences of candidate primers for PCR amplifying the second target region on the basis of the global alignment scores.

(Method for Second-Stage Selection)

A threshold value for global alignment scores (referred to also as "second threshold value") is set in advance.

If a global alignment score is less than the second threshold value, the combination of two base sequences is determined to have low probability of dirtier formation, and then the subsequent step is performed.

On the other hand, if a global alignment score is not less than the second threshold value, the combination of two base sequences is determined to have high probability of dimer formation, and no further steps are performed for the combination.

The second threshold value is not specifically limited and can be set as appropriate. For example, the second threshold value may be set in accordance with PCR conditions such as the amount of genomic DNA that is a template for polymerase chain reaction.

Note that base sequences including several bases from the 3'-ends of primers are set to be the same, whereby a global alignment score determined by performing pairwise global alignment on base sequences having a preset number of bases including the 3'-ends of the base sequences of the respective primers can be made less than the second threshold value.

Here, consideration is given to a case where the second threshold value is set to "+3" in the example provided in the "global alignment step" described above.

In the above example, the global alignment score is "−3" and is less than the second threshold value, that is, "+3". Thus, the combination of the base sequences with SEQ ID NOs: 1 and 2 can be determined to have low probability of primer dimer formation.

Note that this step is performed on all the combinations for which global alignment scores are calculated in the global alignment step S105, the first step of global alignment S205, the second step of global alignment S215, the first global alignment step S305, or the second global alignment step S315.

In addition, to reduce the amount of computation, preferably, both the "global alignment step" and the "second-stage selection step" are performed previously, and both the "local alignment step" and the "first-stage selection step" are performed on a combination of base sequences of primers that have been subjected to the "second-stage selection step". In particular, as the number of target regions and the number of base sequences of candidate primers increase, the effect of reducing the amount of computation increases, leading to an increase in the speed of the overall processing.

This is because in the "global alignment step", global alignment is performed on base sequences having a short length, that is, the "preset sequence length", which requires less computation than the calculation of a local alignment score to find partial sequences having high complementarity from the entire base sequences under the condition that the 3'-ends are included, resulting in higher-speed processing. Note that it is known that a commonly known algorithm allows global alignment to be performed at a higher speed than local alignment when the alignments are performed on sequences having the same length.

<<Amplification Sequence Length Check Step>>

A combination of base sequences of candidate primers determined to have low probability of primer dimer formation in the "first-stage selection step" and the "second-stage selection step" may be subjected to an amplification sequence length check step (not illustrated) to compute the distance between the ends of the base sequences of the candidate primers on the chromosomal DNA to determine whether the distance falls within a preset range.

If the distance between the ends of the base sequences falls within the preset range, the combination of the base sequences of the candidate primers can be determined to be likely to amplify the target region in a suitable manner. The distance between the ends of the base sequences of the candidate primers is not specifically limited and may be set as appropriate in accordance with PCR conditions such as the type of enzyme (DNA polymerase). For example, the range may be set to any of various ranges such as a range of 100 to 200 bases (pairs), a range of 120 to 180 bases (pairs), a range of 140 to 180 bases (pairs), a range of 140 to 160 bases (pairs), and a range of 160 to 180 bases (pairs).

<<Primer Employment Step>>

As used herein, primer employment step S107 (FIG. 13), first step of primer employment S207 and second step of primer employment S217 (FIG. 14), and first primer employment step S307 and second primer employment step S317 (FIG. 15 and FIG. 16) are collectively referred to sometimes simply as "primer employment step".

(Design Method (1): Primer Employment Step S107)

In FIG. 13, this step is represented as "primer employment".

In the design method (1), the primer employment step (g) is a step of employing, as base sequences of primers for PCR amplifying the target region, base sequences of candidate primers selected in both the first-stage selection step and the second-stage selection step.

(Design Method (2): First Step of Primer Employment S207 and Second Step of Primer Employment S217)

In FIG. 14, these steps are represented as "primer employment: first" and "primer employment: second".

In the design method (2), the first step of primer employment ($g_1$) is a step of employing, as base sequences of primers for PCR amplifying the first target region, base sequences of candidate primers selected in both the first step of first-stage selection and the first step of second-stage selection, and the second step of primer employment ($g_2$) is a step of employing, as base sequences of primers for PCR amplifying the second target region, base sequences of candidate primers selected in both the second step of first-stage selection and the second step of second-stage selection.

(Design Method (3): First Primer Employment Step S307 and Second Primer Employment Step S317)

In FIG. 15 and FIG. 16, these steps are represented as "first primer employment" and "second primer employment".

In the design method (3) and its modification, the first primer employment step (g-1) is a step of employing base sequences of candidate primers selected in both the first first-stage selection step and the first second-stage selection step as base sequences of primers for PCR amplifying the first target region, and the second primer employment step (g-2) is a step of employing base sequences of candidate primers selected in both the second first-stage selection step and the second second-stage selection step as base sequences of primers for PCR amplifying the second target region.

(Method for Primer Employment)

In the primer employment step, base sequences of candidate primers having a local alignment score less than the first threshold value, where the local alignment score is determined by performing pairwise local alignment on base sequences of candidate primers under the condition that the partial sequences to be compared include the 3'-ends of the base sequences, and having a global alignment score less than the second threshold value, where the global alignment score is determined by performing pairwise global alignment on base sequences having a preset number of bases including the 3'-ends of the base sequences of the candidate primers, are employed, as base sequences of primers for amplifying a target region.

For example, consideration is given to the employment of base sequences with SEQ ID NOs: 1 and 2 given in Table 7 as base sequences of primers for amplifying a target region.

TABLE 7

| | Base sequence (5'→3') |
|---|---|
| SEQ ID NO: 1 | TAGCCGGATGTGGGAGATGG |
| SEQ ID NO: 2 | CCAGCATTGGAAAGATCTGG |

As described previously, the local alignment score is "+1" and is thus less than the first threshold value, that is, "+3". Further, the global alignment score is "−3" and is thus less than the second threshold value, that is, "+3".

Accordingly, the base sequence of the candidate primer indicated by SEQ ID NO: 1 and the base sequence of the candidate primer indicated by SEQ ID NO: 2 can be employed as base sequences of primers for amplifying a target region.

<<Primer Design for Other Candidate Amplification Regions>>

After the employment of primers for one candidate amplification region, primers may further be designed in the candidate amplification region having the next priority (step S108).

In the design method (1), if base sequences of candidate primers for a candidate amplification region having the next priority have been generated in the candidate primer base sequence generation step S102, the local alignment step S103 and the following steps are performed (step S109). If base sequences of candidate primers for a candidate amplification region having the next priority have not been generated, a candidate amplification region having the next priority is not selected in the target region selection step S101. Thus, in the target region selection step S101, a candidate amplification region having the next priority is selected. Then, in the candidate primer base sequence generation step S102, base sequences of candidate primers for the candidate amplification region are generated. After that, the local alignment step S103 and the subsequent steps are performed (step S109).

In the design method (2), the process repeats from the second step of target region selection S211 (step S208).

In the design method (3) and its modification, base sequences of candidate primers for the candidate amplification regions selected in the plurality-of-target-region selection step S301 have been generated in the plurality-of-candidate-primer-base-sequence generation step S302. Thus, the process repeats from the second local alignment step S313 (step S308).

<<Feature Point in Designing of Primers, etc.>>

In brief, a feature point in the designing of primers, etc. after candidate amplification regions are assigned priorities is that a plurality of specific target regions are selected, nearby base sequences are searched for, the complementarity of the found nearby base sequences to each of extracted primer sets is examined, and base sequences with low complementarity are selected to obtain a primer group in which primers are not complementary to each other and for which a target region is included in an object to be amplified.

A feature point in the examination of the complementarity of base sequences of primers is to generate a primer group so as to reduce the complementarity of the entire sequences by using local alignment and reduce the complementarity of ends of the base sequences of the primers by using global alignment.

The present invention will be described more specifically hereinafter with reference to Examples. However, the present invention is not limited to these Examples.

EXAMPLES

Comparative Example 1/Example 1/Example 2

<Selection of Candidate Amplification Region>

As candidate amplification regions, 17 regions X01 to X17 including SNV (Single Nucleotide Variant) were selected from among regions on human chromosome 13.

Table 8 below shows chromosomes including candidate amplification regions, the SNV coordinates of the candidate amplification regions, and priorities of the candidate amplification regions assigned in Comparative Example 1, Example 1, and Example 2. Here, the SNV coordinates are coordinates based on GRCh37.p13 (Genome Resource Consortium, human genome assembly data, Release 37, Patch 13; GenBank Accession no. CM000675.1). The way of assigning priorities to candidate amplification regions will be described below.

TABLE 8

| Candidate amplification region | | | Priority | | |
|---|---|---|---|---|---|
| ID | Chromosome | SNV coordinate | Comparative Example 1 | Example 1 | Example 2 |
| X01 | 13 | 20763642 | 1 | 1 | 1 |
| X02 | 13 | 24798120 | 2 | 14 | 10 |
| X03 | 13 | 25265103 | 3 | 16 | 14 |
| X04 | 13 | 27845654 | 4 | 12 | 2 |
| X05 | 13 | 36385031 | 5 | 11 | 3 |
| X06 | 13 | 36743177 | 6 | 15 | 11 |
| X07 | 13 | 36801415 | 7 | 17 | 15 |
| X08 | 13 | 36886469 | 8 | 13 | 17 |
| X09 | 13 | 46946157 | 9 | 4 | 4 |
| X10 | 13 | 52544805 | 10 | 8 | 5 |
| X11 | 13 | 53608479 | 11 | 6 | 12 |
| X12 | 13 | 67800935 | 12 | 3 | 6 |
| X13 | 13 | 95858978 | 13 | 5 | 7 |
| X14 | 13 | 102366825 | 14 | 9 | 8 |
| X15 | 13 | 103396716 | 15 | 10 | 13 |
| X16 | 13 | 103397937 | 16 | 7 | 16 |
| X17 | 13 | 111098226 | 17 | 2 | 9 |

Comparative Example 1

<<Setting of Priorities>>

The candidate amplification regions X01 to X17 were assigned priorities from 1 through 17, with 1 being highest, in order from lowest to highest in terms of SNV coordinate.

In Table 8, the "priority" column indicates the priorities of the candidate amplification regions.

<<Designing of Primers and Primer Pairs>>

Primers and primer pairs for amplifying candidate amplification regions by multiplex PCR were designed in order from highest to lowest in terms of priority of the candidate amplification regions.

As a result, primers for multiplex PCR were successfully designed in the candidate amplification regions having priorities from 1 through 10.

In Table 9, the "primer" column indicates the names, base sequences, and SEQ ID NOs: of primers constituting each primer pair.

Figure 17:
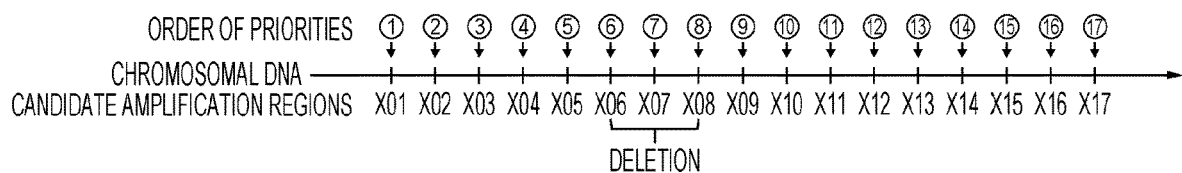
FIG. 17 is a diagram illustrating how priorities are assigned to candidate amplification regions in Comparative Example 1, in which candidate amplification regions are assigned priorities in order from smallest to largest in terms of coordinate, and X06, X07, and X08 out of ten candidate amplification regions in which primers are designed are not amplified due to the deletion of chromosomal DNA, resulting in it being likely that the number of regions necessary for analysis will not be reached.

Further, FIG. 17 illustrates the physical arrangement of candidate amplification regions on chromosomal DNA and the order of priorities of the candidate amplification regions. Note that the distances between the regions in the figure do not reflect the actual distances on chromosomal DNA.

TABLE 9

| Priority | ID | Candidate amplification region<br>Upper: Start point coordinate<br>Lower: End point coordinate | Primer Name | Primer Base sequence (5'→3')<br>Upper: Forward<br>Lower: Reverse | SEQ ID NO: |
|---|---|---|---|---|---|
| 1 | X01 | 20763493<br>20763668 | 20763642-F<br>20763642-R | TAGCCGGATGTGGGAGATGG<br>CCAGCATTGGAAAGATCTGG | 1<br>2 |
| 2 | X02 | 24797765<br>24797943 | 24798120-F<br>24798120-R | CCGTGTGTGAGATTCTCGTG<br>ACTGCTCAGGGTCCTCTGTG | 3<br>4 |
| 3 | X03 | 25264984<br>25265146 | 25265103-F<br>25265103-R | GGCCTAGAGGACGATGCTTG<br>TGTTGATAACCATGCCGGTG | 5<br>6 |
| 4 | X04 | 27845535<br>27845710 | 27845654-F<br>27845654-R | CCTTCACTCCCCCCAGTTTG<br>GCATAAAAGCAGGGAGCGTG | 7<br>8 |
| 5 | X05 | 36384994<br>36385161 | 36385031-F<br>36385031-R | GAGCCACGTATGTTGGGGTG<br>AAAGGGCTTTTGAGCTCTTG | 9<br>10 |
| 6 | X06 | 38743041<br>36743200 | 36743177-F<br>36743177-R | AAACCATGCCAACTCTTTTG<br>TCTTTGCAGCAACAGTTTTG | 11<br>12 |
| 7 | X07 | 36801293<br>36801464 | 36801415-F<br>36801415-R | AGATCACAATCCTGGGGGTG<br>GGGTTTCAGTGCTGCAGGTG | 13<br>14 |
| 8 | X08 | 36886336<br>36886511 | 36886469-F<br>36886469-R | GCTGCACATTCCAATCCTTG<br>AGATGGGAAATCTCCTCTGG | 15<br>16 |
| 9 | X09 | 46946127<br>46946293 | 46946157-F<br>46946157-R | TCTCAGGATATGGGGAGGTG<br>GGATACCACAGACTCCGTTG | 17<br>18 |
| 10 | X10 | 52544670<br>52544838 | 52544805-F<br>52544805-R | ATGCACAGGTCATGCCTTTG<br>ATGGTGCAAACTACAGATGG | 19<br>20 |

Example 1

<<Setting of Priorities>>

The candidate amplification regions X01 to X17 were assigned priorities in the following way.

In Table 8, the "priority" column indicates the priorities of the candidate amplification regions.

X01 (SNV coordinate: 20,763,642) having the minimum SNV coordinate was assigned a priority of 1.

X17 (SNV coordinate: 111,098,226) having the maximum SNV coordinate was assigned a priority of 2.

X12 (SNV coordinate: 67,800,935) closest to the midpoint of X01 and X17 (coordinate: 65,930,934) was assigned a priority of 3.

X09 (SNV coordinate: 46,946,157) closest to the midpoint of X01 and X12 (coordinate: 44,282,288.5) was assigned a priority of 4.

X13 (SNV coordinate: 95,858,978) closest to the midpoint of X12 and X17 (coordinate: 89,449,580.5) was assigned a priority of 5.

X11 (SNV coordinate: 53,608,479) closest to the midpoint of X09 and X12 (coordinate: 57,373,546) was assigned a priority of 6.

X16 (SNV coordinate: 103,397,937) closest to the midpoint of X13 and X17 (coordinate: 103,478,602) was assigned a priority of 7.

X10 (SNV coordinate: 52,544,805) closest to the midpoint of X09 and X11 (coordinate: 50,277,318) was assigned a priority of 8.

X14 (SNV coordinate: 102,366,825) closest to the midpoint of X13 and X16 (coordinate: 99,628,457.5) was assigned a priority of 9.

X15 (SNV coordinate: 103,396,716) closest to the midpoint of X14 and X16 (coordinate: 102,882,381) was assigned a priority of 10.

X05 (SNV coordinate: 36,385,031) closest to the midpoint of X01 and X09 (coordinate: 33,854,899.5) was assigned a priority of 11.

X04 (SNV coordinate: 27,845,654) closest to the midpoint of X01 and X05 (coordinate: 28,574,336.5) was assigned a priority of 12.

X08 (SNV coordinate: 36,886,469) closest to the midpoint of X05 and X09 (coordinate: 41,665,594) was assigned a priority of 13.

X02 (SNV coordinate: 24,798,120) closest to the midpoint of X01 and X04 (coordinate: 44,282,288.5) was assigned a priority of 14.

X06 (SNV coordinate: 36,743,177) closest to the midpoint of X05 and X08 (coordinate: 36,635,750) was assigned a priority of 15.

X03 (SNV coordinate: 25,265,103) closest to the midpoint of X02 and X04 (coordinate: 26,321,887) was assigned a priority of 16.

X07 (SNV coordinate: 36,801,415) closest to the midpoint of X06 and X08 (coordinate: 36,814,823) was assigned a priority of 17.

<<Designing of Primers and Primer Sets>>

Primers and primer pairs for amplifying candidate amplification regions by multiplex PCR were designed in order from highest to lowest in terms of priority of the candidate amplification regions.

As a result, primers for multiplex PCR were successfully designed in the candidate amplification regions having priorities from 1 through 10.

In Table 10, the "primer" column indicates the names, base sequences, and SEQ ID NOs: of primers constituting each primer pair.

Figure 18:
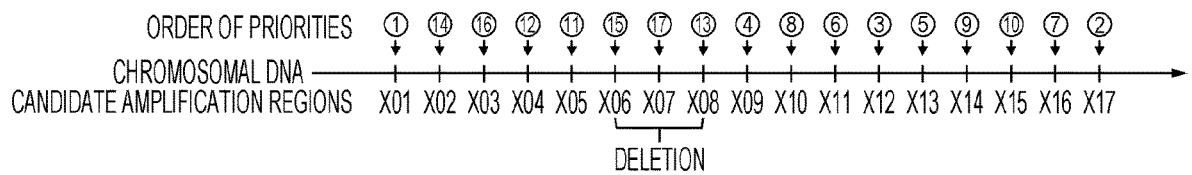
FIG. 18 is a diagram illustrating how priorities are assigned to candidate amplification regions in Example 1, in which candidate amplification regions are assigned priorities dichotomically, and X06, X07, and X08 on chromosomal DNA, which are deleted, are not included in ten candidate amplification regions in which primers are designed, and thus have no effect on the number of regions necessary for analysis.

Further, FIG. 18 illustrates the physical arrangement of candidate amplification regions on chromosomal DNA and the order of priorities of the candidate amplification regions. Note that the distances between the regions in the figure do not reflect the actual distances on chromosomal DNA.

TABLE 10

| | | Candidate amplification region | | Primer | | |
|---|---|---|---|---|---|---|
| Priority | ID | Upper: Start point coordinate Lower: End point coordinate | Name | Base sequence (5'→3') Upper: Forward Lower: Reverse | | SEQ ID NO: |
| 1 | X01 | 20763493<br>20763668 | 20763642-F<br>20763642-R | TAGCCGGATGTGGGAGATGG<br>CCAGCATTGGAAAGATCTGG | | 1<br>2 |
| 2 | X17 | 111098108<br>111098274 | 111098226-F<br>111098226-R | GCCATTGCAGTCCCTTTTTG<br>TGGGCGAGACACCATAAGTG | | 33<br>34 |
| 3 | X12 | 67800891<br>67801046 | 67800935-F<br>67800935-R | GTAACAATCACAGCCGCTTG<br>ACCGAATGCCTCCTTCTTTG | | 23<br>24 |
| 4 | X09 | 46946127<br>46946293 | 46946157-F<br>46946157-R | TCTCAGGATATGGGGAGGTG<br>GGATACCACAGACTCCGTTG | | 17<br>18 |
| 5 | X13 | 95858920<br>95859093 | 95858978-F<br>95858978-R | CGAGGAGCACGTAGGTGGTG<br>TGAGCCACTTTATCTGGTTG | | 25<br>26 |
| 6 | X11 | 53608432<br>53608573 | 53608479-F<br>53608479-R | AAAGCTCAGATTCCAGCTTG<br>CTCTGTCCACGGGAAAGGTG | | 21<br>22 |
| 7 | X16 | 103397865<br>103398033 | 103397937-F<br>103397937-R | CAGCACCAGCCCTGATATTG<br>AAAGAGACAGCGATTTTTGG | | 31<br>32 |
| 8 | X10 | 52544670<br>52544838 | 52544805-F<br>52544805-R | ATGCACAGGTCATGCCTTTG<br>ATGGTGCAAACTACAGATGG | | 19<br>20 |
| 9 | X14 | 102366796<br>102366972 | 102366825-F<br>102366825-R | CATTGTGGGAAGTGCATTTG<br>TGCATGACGAGTGTCTCTTG | | 27<br>28 |
| 10 | X15 | 103396639<br>103396800 | 103396716-F<br>103396716-R | TTCAGATGACATGAGGCTGG<br>ACAGGGAAATCAAAGATTGG | | 29<br>30 |

Example 2

<<Setting of Priorities>>

The candidate amplification regions X01 to X17 were assigned priorities in the following way.

In Table 8, the "priority" column indicates the priorities of the candidate amplification regions.

- X01 (SNV coordinate: 20,763,642) was assigned a priority of 1.
- X04 (SNV coordinate: 27,845,654) having a coordinate greater than or equal to 25,763,642, which was equal to the SNV coordinate of X01 plus 5,000,000, and having the smallest coordinate value among candidate amplification regions yet to be assigned priorities was assigned a priority of 2.
- X05 (SNV coordinate: 36,385,031) having a coordinate greater than or equal to 32,845,654, which was equal to the SNV coordinate of X04 plus 5,000,000, and having the smallest coordinate value among candidate amplification regions yet to be assigned priorities was assigned a priority of 3.
- X09 (SNV coordinate: 46,946,157) having a coordinate greater than or equal to 41,385,031, which was equal to the SNV coordinate of X05 plus 5,000,000, and having the smallest coordinate value among candidate amplification regions yet to be assigned priorities was assigned a priority of 4.
- X10 (SNV coordinate: 52,544,805) having a coordinate greater than or equal to 51,946,157, which was equal to the SNV coordinate of X09 plus 5,000,000, and having the smallest coordinate value among candidate amplification regions yet to be assigned priorities was assigned a priority of 5.
- X12 (SNV coordinate: 67,800,935) having a coordinate greater than or equal to 57,544,805, which was equal to the SNV coordinate of X10 plus 5,000,000, and having the smallest coordinate value among candidate amplification regions yet to be assigned priorities was assigned a priority of 6.
- X13 (SNV coordinate: 95,858,978) having a coordinate greater than or equal to 72,800,935, which was equal to the SNV coordinate of X12 plus 5,000,000, and having the smallest coordinate value among candidate amplification regions yet to be assigned priorities was assigned a priority of 7.
- X14 (SNV coordinate: 102,366,825) having a coordinate greater than or equal to 100,858,978, which was equal to the SNV coordinate of X13 plus 5,000,000, and having the smallest coordinate value among candidate amplification regions yet to be assigned priorities was assigned a priority of 8.
- X17 (SNV coordinate: 111,098,226) having a coordinate greater than or equal to 107,366,825, which was equal to the SNV coordinate of X14 plus 5,000,000, and having the smallest coordinate value among candidate amplification regions yet to be assigned priorities was assigned a priority of 9.

X02 (SNV coordinate: 24,798,120) having a coordinate greater than or equal to 116,098,226, which was equal to the SNV coordinate of X17 plus 5,000,000, and having the smallest coordinate value among candidate amplification regions yet to be assigned priorities was assigned a priority of 10.

X06 (SNV coordinate: 36,743,177) having a coordinate greater than or equal to 29,798,120, which was equal to the SNV coordinate of X02 plus 5,000,000, and having the smallest coordinate value among candidate amplification regions yet to be assigned priorities was assigned a priority of 11.

X11 (SNV coordinate: 53,608,479) having a coordinate greater than or equal to 41,743,177, which was equal to the SNV coordinate of X06 plus 5,000,000, and having the smallest coordinate value among candidate amplification regions yet to be assigned priorities was assigned a priority of 12.

X15 (SNV coordinate: 103,396,716) having a coordinate greater than or equal to 58,608,479, which was equal to the SNV coordinate of X11 plus 5,000,000, and having the smallest coordinate value among candidate amplification regions yet to be assigned priorities was assigned a priority of 13.

X03 (SNV coordinate: 25,265,103) having a coordinate greater than or equal to 108,396,716, which was equal to the SNV coordinate of X15 plus 5,000,000, and having the smallest coordinate value among candidate amplification regions yet to be assigned priorities was assigned a priority of 14.

X07 (SNV coordinate: 36,801,415) having a coordinate greater than or equal to 30,265,103, which was equal to the SNV coordinate of X03 plus 5,000,000, and having the smallest coordinate value among candidate amplification regions yet to be assigned priorities was assigned a priority of 15.

X16 (SNV coordinate: 103,397,937) having a coordinate greater than or equal to 41,801,415, which was equal to the SNV coordinate of X07 plus 5,000,000, and having the smallest coordinate value among candidate amplification regions yet to be assigned priorities was assigned a priority of 16.

X08 (SNV coordinate: 36,886,469) having a coordinate greater than or equal to 108,397,937, which was equal to the SNV coordinate of X16 plus 5,000,000, and having the smallest coordinate value among candidate amplification regions yet to be assigned priorities was assigned a priority of 17.

<<Designing of Primers and Primer Sets>>

Primers and primer pairs for amplifying candidate amplification regions by multiplex PCR were designed in order from highest to lowest in terms of priority of the candidate amplification regions.

As a result, primers for multiplex PCR were successfully designed in the candidate amplification regions having priorities from 1 through 10.

In Table 11, the "primer" column indicates the names, base sequences, and SEQ ID NOs: of primers constituting each primer pair.

Figure 19:
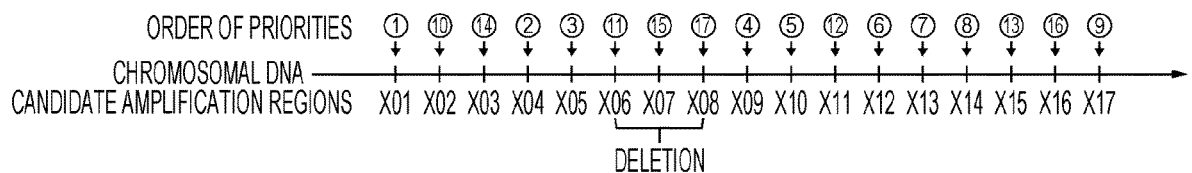
FIG. 19 is a diagram illustrating how priorities are assigned to candidate amplification regions in Example 2, in which candidate amplification regions are assigned priorities based on a threshold distance value, and X06, X07, and X08 on chromosomal DNA, which are deleted, are not included in ten candidate amplification regions in which primers are designed, and thus have no effect on the number of regions necessary for analysis.

Further, FIG. 19 illustrates the physical arrangement of candidate amplification regions on chromosomal DNA and the order of priorities of the candidate amplification regions. Note that the distances between the regions in the figure do not reflect the actual distances on chromosomal DNA.

TABLE 11

| | | Candidate amplification region | Primer | | |
|---|---|---|---|---|---|
| Priority | ID | Upper: Start point coordinate Lower: End point coordinate | Name | Base sequence (5'→3') Upper: Forward Lower: Reverse | SEQ ID NO: |
| 1 | X01 | 20763493 | 20763642-F | TAGCCGGATGTGGGAGATGG | 1 |
| | | 20763668 | 20763642-R | CCAGCATTGGAAAGATCTGG | 2 |
| 2 | X04 | 27845535 | 27845654-F | CCTTCACTCCCCCCAGTTTG | 7 |
| | | 27845710 | 27845654-R | GCATAAAAGCAGGGAGCGTG | 8 |
| 3 | X05 | 36384994 | 36385031-F | GAGCCACGTATGTTGGGGTG | 9 |
| | | 36385161 | 36385031-R | AAAGGGCTTTTGAGCTCTTG | 10 |
| 4 | X09 | 46946127 | 46946157-F | TCTCAGGATATGGGGAGGTG | 17 |
| | | 46946293 | 46946157-R | GGATACCACAGACTCCGTTG | 18 |
| 5 | X10 | 52544670 | 52544805-F | ATGCACAGGTCATGCCTTTG | 19 |
| | | 52544838 | 52544805-R | ATGGTGCAAACTACAGATGG | 2 |
| 6 | X12 | 67800891 | 67800935-F | GTAACAATCACAGCCGCTTG | 23 |
| | | 67801046 | 67800935-R | ACCGAATGCCTCCTTCTTTG | 24 |
| 7 | X13 | 95858920 | 95858978-F | CGAGGAGCACGTAGGTGGTG | 25 |
| | | 95859093 | 95858978-R | TGAGCCACTTTATCTGGTTG | 26 |
| 8 | X14 | 102366796 | 102366825-F | CATTGTGGGAAGTGCATTTG | 27 |
| | | 102366972 | 102366825-R | TGCATGACGAGTGTCTCTTG | 28 |

TABLE 11-continued

| | | Candidate amplification region | | Primer | | |
|---|---|---|---|---|---|---|
| Priority | ID | Upper: Start point coordinate Lower: End point coordinate | Name | Upper: Forward Lower: Reverse | Base sequence (5'→3') | SEQ ID NO: |
| 9 | X17 | 111098108 111098274 | 111098226-F 111098226-R | GCCATTGCAGTCCCTTTTG TGGGCGAGACACCATAAGTG | | 33 34 |
| 10 | X02 | 24797765 24797943 | 24798120-F 24798120-R | CCGTGTGTGAGATTCTCGTG ACTGCTCAGGGTCCTCTGTG | | 3 4 |

Effects of Examples 1 and 2

Comparative Example 1 aims to design primers and primer pairs for multiplex PCR for all of the 17 candidate amplification regions. However, as a result of the examination of the specificity, the probability of primer dimer formation, and the like of a primer, primers and primer pairs can be designed only for ten of the candidate amplification regions.

Example 1 and Example 2 also aim to design primers and primer pairs for multiplex PCR for all of the 17 candidate amplification regions. However, as a result of the examination of the specificity, the probability of primer dimer formation, and the like of a primer, primers and primer pairs can be designed only for ten of the candidate amplification regions.

When the candidate amplification regions X06 to X08 are deleted in template DNA, it is not possible to amplify these regions. Thus, in Comparative Example 1, the number of regions for which base sequence information of SNV can be obtained is further reduced to seven from ten although primers and primer sets could be designed in ten regions, whereas in Example 1 and Example 2, there is no influence of the deletion of X06 to X08.

Consequently, Comparative Example 1 is likely to fail to ensure the number of regions necessary for analysis due to the deletion of X06 to X08, whereas Example 1 and Example 2 are unlikely to fail to ensure the number of regions necessary for analysis due to the deletion of X06 to X08.

Comparative Example 2/Example 3

As candidate amplification regions, 99 regions Y01 to Y99 including SNP (Single Nucleotide Polymorphism) were selected from among regions on human chromosome 13.

Table 12, Table 13, and Table 14 below show chromosomes including candidate amplification regions, SNP coordinates, variant frequency (V.F.; Variant Frequency), variant frequency difference (ΔV.F: the absolute value of the difference from a variant frequency of 0.5), and priorities of the candidate amplification regions assigned in Comparative Example 2 and Example 3. Here, the SNP coordinates are coordinates based on GRCh37.p13 (Genome Resource Consortium, human genome assembly data, Release 37, Patch 13; GenBank Accession no. CM000675.1). The way of assigning priorities to candidate amplification regions will be described below.

TABLE 12

| Candidate amplification region | | | | | Priority | |
|---|---|---|---|---|---|---|
| ID | Chromosome | SNV coordinate | V.F. | ΔV.F. | Comparative Example 2 | Example 3 |
| Y01 | 13 | 20224387 | 0.035 | 0.465 | 1 | 86 |
| Y02 | 13 | 20398669 | 0.983 | 0.483 | 2 | 93 |
| Y03 | 13 | 20398742 | 0.983 | 0.483 | 3 | 94 |
| Y04 | 13 | 20411701 | 0.045 | 0.455 | 4 | 81 |
| Y05 | 13 | 20425911 | 0.056 | 0.444 | 5 | 75 |
| Y06 | 13 | 20425948 | 0.040 | 0.460 | 6 | 84 |
| Y07 | 13 | 20763380 | 0.146 | 0.354 | 7 | 55 |
| Y08 | 13 | 20763642 | 0.410 | 0.090 | 8 | 14 |
| Y09 | 13 | 21063524 | 0.067 | 0.433 | 9 | 71 |
| Y10 | 13 | 21086599 | 0.051 | 0.449 | 10 | 78 |
| Y11 | 13 | 21205192 | 0.994 | 0.494 | 11 | 95 |
| Y12 | 13 | 21358061 | 0.186 | 0.314 | 12 | 45 |
| Y13 | 13 | 21383364 | 0.047 | 0.453 | 13 | 79 |
| Y14 | 13 | 21620085 | 0.933 | 0.433 | 14 | 72 |
| Y15 | 13 | 21720956 | 0.709 | 0.209 | 15 | 34 |
| Y16 | 13 | 21729252 | 0.159 | 0.341 | 16 | 52 |
| Y17 | 13 | 21729267 | 0.167 | 0.333 | 17 | 51 |
| Y18 | 13 | 21735998 | 0.076 | 0.424 | 18 | 70 |
| Y19 | 13 | 23824783 | 0.669 | 0.169 | 19 | 25 |
| Y20 | 13 | 23898509 | 0.824 | 0.324 | 20 | 47 |
| Y21 | 13 | 23898664 | 0.994 | 0.494 | 21 | 96 |
| Y22 | 13 | 23905711 | 0.355 | 0.145 | 22 | 20 |
| Y23 | 13 | 23906983 | 0.144 | 0.356 | 23 | 56 |
| Y24 | 13 | 23907909 | 0.365 | 0.135 | 24 | 19 |
| Y25 | 13 | 23908034 | 0.459 | 0.041 | 25 | 5 |
| Y26 | 13 | 23909162 | 0.355 | 0.145 | 26 | 21 |
| Y27 | 13 | 23911748 | 0.241 | 0.259 | 27 | 37 |
| Y28 | 13 | 23911820 | 0.421 | 0.079 | 28 | 10 |
| Y29 | 13 | 23929095 | 0.128 | 0.372 | 29 | 58 |
| Y30 | 13 | 23930055 | 0.122 | 0.378 | 30 | 60 |
| Y31 | 13 | 24167505 | 0.378 | 0.122 | 31 | 16 |
| Y32 | 13 | 24234517 | 0.500 | 0.000 | 32 | 1 |
| Y33 | 13 | 24243204 | 0.179 | 0.321 | 33 | 46 |

TABLE 13

| Candidate amplification region | | | | | Priority | |
|---|---|---|---|---|---|---|
| ID | Chromosome | SNV coordinate | V.F. | ΔV.F. | Comparative Example 2 | Example 3 |
| Y34 | 13 | 24797913 | 0.340 | 0.160 | 34 | 23 |
| Y35 | 13 | 25000617 | 0.326 | 0.174 | 35 | 27 |
| Y36 | 13 | 25008588 | 0.977 | 0.477 | 36 | 90 |
| Y37 | 13 | 25008630 | 0.978 | 0.478 | 37 | 91 |
| Y38 | 13 | 25009099 | 0.978 | 0.478 | 38 | 92 |
| Y39 | 13 | 25009297 | 0.309 | 0.191 | 39 | 33 |
| Y40 | 13 | 25009441 | 0.330 | 0.170 | 40 | 26 |
| Y41 | 13 | 25009485 | 0.314 | 0.186 | 41 | 30 |
| Y42 | 13 | 25020863 | 0.972 | 0.472 | 42 | 87 |
| Y43 | 13 | 25023936 | 0.006 | 0.494 | 43 | 97 |
| Y44 | 13 | 25027744 | 0.972 | 0.472 | 44 | 88 |
| Y45 | 13 | 25029218 | 0.622 | 0.122 | 45 | 17 |
| Y46 | 13 | 25029295 | 0.315 | 0.185 | 46 | 28 |

TABLE 13-continued

| ID | Candidate amplification region | | | | Priority | |
|---|---|---|---|---|---|---|
| | Chromosome | SNV coordinate | V.F. | ΔV.F. | Comparative Example 2 | Example 3 |
| Y47 | 13 | 25033227 | 0.006 | 0.494 | 47 | 98 |
| Y48 | 13 | 25052420 | 0.250 | 0.250 | 48 | 36 |
| Y49 | 13 | 25075859 | 0.605 | 0.105 | 49 | 15 |
| Y50 | 13 | 25265103 | 0.553 | 0.053 | 50 | 8 |
| Y51 | 13 | 25265139 | 0.551 | 0.051 | 51 | 7 |
| Y52 | 13 | 25266932 | 0.581 | 0.081 | 52 | 13 |
| Y53 | 13 | 25272870 | 0.094 | 0.406 | 53 | 65 |
| Y54 | 13 | 25356053 | 0.580 | 0.080 | 54 | 12 |
| Y55 | 13 | 25367301 | 0.455 | 0.045 | 55 | 6 |
| Y56 | 13 | 25378476 | 0.197 | 0.303 | 56 | 44 |
| Y57 | 13 | 25399752 | 0.860 | 0.360 | 57 | 57 |
| Y58 | 13 | 25419176 | 0.901 | 0.401 | 58 | 64 |
| Y59 | 13 | 25428002 | 0.218 | 0.282 | 59 | 40 |
| Y60 | 13 | 25440318 | 0.230 | 0.270 | 60 | 38 |
| Y61 | 13 | 25453420 | 0.128 | 0.372 | 61 | 59 |
| Y62 | 13 | 25466955 | 0.665 | 0.165 | 62 | 24 |
| Y63 | 13 | 25487103 | 0.278 | 0.222 | 63 | 35 |
| Y64 | 13 | 25823451 | 0.052 | 0.448 | 64 | 77 |
| Y65 | 13 | 25825889 | 0.622 | 0.122 | 65 | 18 |
| Y66 | 13 | 25831888 | 0.478 | 0.022 | 66 | 3 |

TABLE 14

| ID | Candidate amplification region | | | | Priority | |
|---|---|---|---|---|---|---|
| | Chromosome | SNV coordinate | V.F. | ΔV.F. | Comparative Example 2 | Example 3 |
| Y67 | 13 | 25876011 | 0.494 | 0.006 | 67 | 2 |
| Y68 | 13 | 26043182 | 0.174 | 0.326 | 68 | 48 |
| Y69 | 13 | 26148966 | 0.202 | 0.298 | 69 | 42 |
| Y70 | 13 | 26535734 | 0.006 | 0.494 | 70 | 99 |
| Y71 | 13 | 26788114 | 0.110 | 0.390 | 71 | 62 |
| Y72 | 13 | 26789638 | 0.041 | 0.459 | 72 | 83 |
| Y73 | 13 | 26793644 | 0.040 | 0.460 | 73 | 85 |
| Y74 | 13 | 27239161 | 0.056 | 0.444 | 74 | 76 |
| Y75 | 13 | 27250823 | 0.078 | 0.422 | 75 | 69 |
| Y76 | 13 | 27257004 | 0.042 | 0.458 | 76 | 82 |
| Y77 | 13 | 28009031 | 0.028 | 0.472 | 77 | 89 |
| Y78 | 13 | 28009851 | 0.110 | 0.390 | 78 | 63 |
| Y79 | 13 | 28009920 | 0.562 | 0.062 | 79 | 9 |
| Y80 | 13 | 28143229 | 0.348 | 0.152 | 80 | 22 |
| Y81 | 13 | 28239940 | 0.311 | 0.189 | 81 | 32 |

TABLE 14-continued

| ID | Candidate amplification region | | | | Priority | |
|---|---|---|---|---|---|---|
| | Chromosome | SNV coordinate | V.F. | ΔV.F. | Comparative Example 2 | Example 3 |
| Y82 | 13 | 28239970 | 0.421 | 0.079 | 82 | 11 |
| Y83 | 13 | 28367956 | 0.157 | 0.343 | 83 | 53 |
| Y84 | 13 | 28537317 | 0.849 | 0.349 | 84 | 54 |
| Y85 | 13 | 28562605 | 0.213 | 0.287 | 85 | 41 |
| Y86 | 13 | 28610183 | 0.686 | 0.186 | 86 | 31 |
| Y87 | 13 | 28624294 | 0.798 | 0.298 | 87 | 43 |
| Y88 | 13 | 28893642 | 0.112 | 0.388 | 88 | 61 |
| Y89 | 13 | 29600415 | 0.062 | 0.438 | 89 | 73 |
| Y90 | 13 | 29855847 | 0.080 | 0.420 | 90 | 68 |
| Y91 | 13 | 29898768 | 0.910 | 0.410 | 91 | 66 |
| Y92 | 13 | 30091714 | 0.955 | 0.455 | 92 | 80 |
| Y93 | 13 | 30091819 | 0.944 | 0.444 | 93 | 74 |
| Y94 | 13 | 30107067 | 0.522 | 0.022 | 94 | 4 |
| Y95 | 13 | 31221106 | 0.084 | 0.416 | 95 | 67 |
| Y96 | 13 | 31231806 | 0.169 | 0.331 | 96 | 49 |
| Y97 | 13 | 31233063 | 0.169 | 0.331 | 97 | 50 |
| Y98 | 13 | 31531009 | 0.221 | 0.279 | 98 | 39 |
| Y99 | 13 | 31891746 | 0.685 | 0.185 | 99 | 29 |

Comparative Example 2

<<Setting of Priorities>>

The candidate amplification regions Y01 to Y99 were assigned priorities from 1 through 99 in order from lowest to highest in terms of SNP coordinate.

In Table 12, Table 13, and Table 14, the "priority" column indicates the priorities of the candidate amplification regions.

<<Designing of Primers and Primer Pairs>>

Primers and primer pairs for amplifying candidate amplification regions by multiplex PCR were designed in order from highest to lowest in terms of priority of the candidate amplification regions.

As a result, primers for multiplex PCR were successfully designed in the candidate amplification regions having priorities from 1 through 60.

For ten primer pairs out of the designed primers and primer pairs, in Table 15, the "primer" column indicates the names, base sequences, and SEQ ID NOs: of primers constituting each primer pair.

TABLE 15

| | Candidate amplification region | | Primer | | |
|---|---|---|---|---|---|
| Priority | ID | Upper: Start point coordinate Lower: End point coordinate | Name | Base sequence (5'→3') Upper: Forward Lower: Reverse | SEQ ID NO: |
| 1 | Y07 | 20763333<br>20763509 | 20763380-F<br>20763380-R | CTTCGATGCGGACCTTCTGG<br>TCTCCCACATCCGGCTATGG | 35<br>36 |
| 2 | Y10 | 21086543<br>21086697 | 21086599-F<br>21086599-R | CCCACTTCCATTCCTTCTGG<br>CCCTTCAGTGGAGTCATTGG | 37<br>38 |
| 3 | Y11 | 21205086<br>21205235 | 21205192-F<br>21205192-R | TTTCCCCGACCATAAGCTTG<br>ATACAGGGCTGAGAGATTGG | 39<br>40 |
| 4 | Y13 | 21383267<br>21383431 | 21383364-F<br>21383364-R | ATTCCTACACTGGCCAGTTG<br>AGCCACAGAAGTGCACGTTG | 41<br>42 |
| 5 | Y14 | 21619945<br>21620115 | 21620085-F<br>21620085-R | TGATAAGGTCCGAACTTTGG<br>GCGACTGCAAGAGATTCGTG | 43<br>44 |
| 6 | Y21 | 23898620<br>23898767 | 23898664-F<br>23898664-R | GTACCTGTCTGTGGCCGGTG<br>CCTCAGTCTTTCACGATGTG | 45<br>46 |

TABLE 15-continued

| | | Candidate amplification region | | | | |
|---|---|---|---|---|---|---|
| | | Upper: Start point | | Primer | | |
| Priority | ID | coordinate Lower: End point coordinate | Name | Base sequence (5'→3') Upper: Forward Lower: Reverse | | SEQ ID NO: |
| 7 | Y25 | 23907922<br>23908082 | 23908034-F<br>23908034-R | GAGCCTTCAAGATGCTTGTG<br>TTTTCCAAATGCCCAGAGTG | | 47<br>48 |
| 8 | Y34 | 24797765<br>24797943 | 24797913-F<br>24797913-R | CCGTGTGTGAGATTCTCGTG<br>ACTGCTCAGGGTCCTCTGTG | | 3<br>4 |
| 9 | Y38 | 25008979<br>25009150 | 25009099-F<br>25009099-R | AATCCAGCTCAGGGAAGGTG<br>ATCCCACAGTCGGCGTCTTG | | 49<br>50 |
| 10 | Y46 | 25029140<br>25029301 | 25029218-F<br>25029218-R | CCAAAGCGCACTCACCTGTG<br>TAGCCAGTGAGAGCGAAGTG | | 51<br>52 |

Example 3

<<Setting of Priorities>>

The candidate amplification regions Y01 to Y99 were assigned priorities from 1 through 99 in order from lowest to highest in terms of ΔV.F. of the SNPs, that is, in order of the variant frequency V.F. from closest to farthest from 0.5.

In Table 12, Table 13, and Table 14, the "priority" column indicates the priorities of the candidate amplification regions.

<<Designing of Primers and Primer Pairs>>

Primers and primer pairs for amplifying candidate amplification regions by multiplex PCR were designed in order from highest to lowest in terms of priority of the candidate amplification regions.

As a result, primers for multiplex PCR were successfully designed in the candidate amplification regions having priorities from 1 through 60.

For ten primer pairs out of the designed primers and primer pairs, in Table 16, the "primer" column indicates the names, base sequences, and SEQ ID NOs: of primers constituting each primer pair.

TABLE 16

| | | Candidate amplification region | | | | |
|---|---|---|---|---|---|---|
| | | Upper: Start point | | Primer | | |
| Priority | ID | coordinate Lower: End point coordinate | Name | Base sequence (5'→3') Upper: Forward Lower: Reverse | | SEQ ID NO: |
| 1 | Y25 | 23907922<br>23908082 | 23908034-F<br>23908034-R | GAGCCTTCAAGATGCTTGTG<br>TTTTCCAAATGCCCAGAGTG | | 47<br>48 |
| 2 | Y50 | 25265003<br>25265178 | 25265103-F<br>25265103-R | GGCCTTGGGAATGTGGTGTG<br>GGCAATATGGCCAATGATGG | | 53<br>54 |
| 3 | Y52 | 25266857<br>25267020 | 25266932-F<br>25266932-R | TGCTGGACAGTGACTCATGG<br>CATTTTCCTGTCCTGGCTTG | | 55<br>56 |
| 4 | Y08 | 20763493<br>20763668 | 20763642-F<br>20763642-R | TAGCCGGATGTGGGAGATGG<br>CCAGCATTGGAAAGATCTGG | | 1<br>2 |
| 5 | Y45 | 25029140<br>25029301 | 25029218-F<br>25029218-R | CCAAAGCGCACTCACCTGTG<br>TAGCCAGTGAGAGCGAAGTG | | 51<br>52 |
| 6 | Y34 | 24797765<br>24797943 | 24797913-F<br>24797913-R | CCGTGTGTGAGATTCTCGTG<br>ACTGCTCAGGGTCCTCTGTG | | 3<br>4 |
| 7 | Y86 | 28610093<br>28610262 | 28610183-F<br>28610183-R | TTCTTCCAGGTCCAAGATGG<br>TTGGCTTCACAAAGTATTGG | | 57<br>58 |
| 8 | Y87 | 28624257<br>28624427 | 28624294-F<br>28624294-R | CCTGCCCAGTTCATTTCTGG<br>TCCTCTTGAGCATTCATTTG | | 59<br>60 |
| 9 | Y68 | 26043061<br>26043241 | 26043182-F<br>26043182-R | CCTGGCGGTTGACTTCTTTG<br>AATTTGTTGAGATGCGGTTG | | 61<br>62 |
| 10 | Y83 | 28367853<br>28368020 | 28367956-F<br>28367956-R | AGAAGCAGGTGAAGATCTGG<br>CGTCATCCTCGGAGCACTTG | | 63<br>64 |

Effect of Example 3

With the use of cells derived from a pregnant woman (mother), which were obtained from the oral cavity of the pregnant woman (mother), and nucleated red blood cells derived from a fetus (child), which were obtained from the blood of the pregnant woman (mother), 60 SNP loci for which primers for multiplex PCR were successfully designed among the 99 SNP loci on chromosome 13 given in Tables 12 to 14 were subjected to genotyping to carry out a maternity test, and the precision was determined.

The mother-child relation was established both for the primers and primer sets designed in accordance with the method according to Comparative Example 2 and for the primers and primer sets designed in accordance with the method according to Example 3. The precision of the maternity test in Comparative Example 2 was about 13.2% with a large error and low accuracy, whereas the precision of the maternity test in Example 3 was about 4.5% with a small error and high accuracy.

Note that a maternity test is based on the use of reliably mother-derived cells and allegedly child-derived, isolated cells. In SNP analysis using n SNP loci having variant frequencies $p_1, p_2, p_3, \ldots,$ and $p_n$, given the number of SNP loci in which genotypes are different is denoted by M, the average number of SNP loci in which the genotypes of unrelated individuals are different is denoted by F, and the average number of SNP loci in which the genotypes of mother and child are different is denoted by G, if $|M-F|>|M-G|$ is satisfied, the allegedly child-derived, isolated cells are determined to be derived from the child, and if $|M-F|<|M-G|$ is satisfied, the allegedly child-derived, isolated cells are determined to be contaminated cells derived from unrelated individuals.

Here, F and G are given by the following formulas. Note that the effects of allele dropout and allele dropin are ignored.

$$F = \sum_{i=1}^{n} f(p_i)$$

$$G = \sum_{i=1}^{n} g(p_i)$$

Here, for SNP loci with variant frequencies p ($0 \leq p \leq 1$), the probability f(p) that unrelated individuals have different genotypes and the probability g(p) that mother and child have different genotypes are assumed to be represented by the following formulas, where $q=1-p$.

$f(p)=1-(p^4+4p^2q^2+q^4)$ $g(p)=1-(p^2+q^2)$

REFERENCE SIGNS LIST 11 arithmetic means (CPU)
12 storage means (memory)
13 auxiliary storage means (storage)
14 input means (keyboard)
15 auxiliary input means (mouse)
16 display means (monitor)
17 output means (printer)

---

What is claimed is:

1. A method for designing primer pairs for multiplex PCR performed by CPU and an operation program operating the CPU, according to a priority k, the primer pairs PCR amplifying n candidate amplification regions on same chromosomal DNA, and the priority k being assigned to each of the n candidate amplification regions, where k is an integer satisfying 1≤k≤n, and n is an integer satisfying n>3, the method including: a step of selecting the n candidate amplification regions on same chromosomal DNA;

a step of obtaining coordinate information and identification information, the coordinate information being a coordinate value r of each of the selected n candidate amplification regions, and the identification information being an identification name R of each of the selected n candidate amplification regions that are assigned identification numbers in an increasing order of the coordinate value r of the n candidate amplification regions;

a first priority setting step of, using the coordinate information and the identification information of the n candidate amplification regions, searching for a minimum coordinate value $r_{min}$ and a maximum coordinate value $r_{max}$ and setting a candidate amplification region $R_{min}$ having the minimum coordinate value Imin as a candidate amplification region $R_{min}(k=1)$ having a first priority (k=1) or a candidate amplification region $R_{max}$ having the maximum coordinate value $r_{max}$ as a candidate amplification region $R_{max}(k=1)$ having a first priority (k=1);

a second priority setting step of setting the candidate amplification region $R_{min}$ having the minimum coordinate value $r_{min}$ that was not set as having the first priority in the first priority setting step as a candidate amplification region $R_{min}(k=2)$ having a second priority (k=2) or the candidate amplification region $R_{max}$ having the maximum coordinate value Imax that was not set as having the first priority in the first priority setting step as a candidate amplification region $R_{max}(k=2)$ having a second priority (k=2); and a k-th priority setting step of using the identification information, coordinate information, and priority information of the n candidate amplification regions, searching for a candidate amplification region $R_i$ and a candidate amplification region $R_j$ satisfying a condition that a candidate amplification region R(k=i) has i-th priority (k=i) and a coordinate value $r_i$ while a candidate amplification region R(k=j) has j-th priority (k j) and a coordinate value $r_j$, and that no candidate amplification region assigned a priority is present but at least one candidate amplification region yet to be assigned a priority is present between the candidate amplification region $R_i$ and the candidate amplification region $R_j$, then calculating a coordinate value $r_{i-j}$ of a midpoint between the candidate amplification region $R_i$ and the candidate amplification region $R_j$ in accordance with $r_{i-j}=(r_i+r_j)/2$, and further searching for and setting a candidate amplification region having a coordinate value closest to the coordinate value $r_{i-j}$ of the midpoint or closest to the midpoint as a candidate amplification region R(k) assigned k-th priority, the k-th priority setting step being repeated until all of the n candidate amplification regions are each assigned a priority;

a step of selecting a predetermined number of candidate amplification regions from the n candidate amplification regions in order from the highest priority as amplification purpose regions and designing at least one primer pair for each of the selected amplification purpose regions;

where i and j satisfy 1≤i≤k−1, 1≤j≤k−1, and i≠j, $r_i$ and $r_j$ satisfy $r_{min} \le r_i \le r_{max}$, $r_{min} \le r_j \le r_{max}$, and $r_i \ne r_j$; and using the at least one primer pair in multiplex PCR analysis.

2. The method for designing primer pairs according to claim 1, wherein the primer pairs are used in genotyping analysis.

3. A method for designing primer pairs for multiplex PCR performed by CPU and an operation program operating the CPU, according to a priority k, the primer pairs PCR amplifying n candidate amplification regions on same chromosomal DNA, and the priority k being assigned to each of the n candidate amplification regions, where k is an integer satisfying 1<k≤n, and n is an integer satisfying n≥3, the method including the following steps:

a step of selecting the n candidate amplification regions on same chromosomal DNA;

a step of obtaining coordinate information and identification information, the coordinate information being a coordinate value r of each of the selected n candidate amplification regions, and the identification information being an identification name R of each of the selected n candidate amplification regions that are assigned identification numbers in an increasing order of the coordinate value r of the n candidate amplification regions;

a first priority setting step of, using the coordinate information and the identification information of the n candidate amplification regions, searching for a minimum coordinate value $r_{min}$ and a maximum coordinate value $r_{max}$ and setting a candidate amplification region $R_{min}$ having the minimum coordinate value Imin as a candidate amplification region $R_{min}(k=1)$ having a first priority (k=1) or a candidate amplification region $R_{max}$ having the maximum coordinate value $r_{max}$ as a candidate amplification region $R_{max}(k=1)$ having a first priority (k=1);

a k-th priority setting step of, using the identification information, coordinate information, and priority information of the candidate amplification regions, searching for an identification name $R_{k-1}$ and a coordinate value $r_{k-1}$ of the candidate amplification region $R_{min}(k-1)$ or the candidate amplification region $R_{max}(k-1)$ having the first priority calculating $T=r_{k-1}+t$, where t is a threshold value and a real number satisfying t>0;

when satisfying $T=r_{k-1}+t \le r_{max}$ searching for candidate amplification regions each having a coordinate value not less than fr−1+t and not larger than $r_{max}$, and assigning k-th priority to a candidate amplification region not yet assigned a priority and having a minimum coordinate value not less than rk−1, or when no such candidate amplification region not yet assigned a priority and having a minimum coordinate value not lower than $r_{min}$; or when satisfying $T=r_{k-1}+t>r_{max}$ assigning k-th priority to a candidate amplification region not yet assigned a priority and having a minimum coordinate value not lower than lmin; and a step of selecting a predetermined number of candidate amplification regions from the n candidate amplification regions in order from the highest priority as amplification purpose regions and designing at least one primer pair for each of the selected amplification purpose regions; and using the at least one primer pair in multiplex PCR analysis.

4. The method for designing primer pairs according to claim 3, wherein t is 100,000 or more.

5. The method for designing primer pairs according to claim 4, wherein the primer pairs are used in genotyping analysis.

6. The method for designing primer pairs according to claim 3, wherein the primer pairs are used in genotyping analysis.

7. A method for designing primer pairs for multiplex PCR performed by CPU and an operation program operating the CPU, according to a priority k, the primer pairs PCR amplifying n candidate amplification regions on same chromosomal DNA, and the priority k being assigned to each of the n candidate amplification regions, where k is an integer satisfying 1≤k≤n, and n is an integer satisfying n≥2, the method including a step of selecting the n candidate amplification regions on same chromosomal DNA;

a step of obtaining identification information, the identification information being an identification name R of each of the selected n candidate amplification regions that are assigned identification numbers in an increasing order of coordinate values r of the n candidate amplification regions;

a step of obtaining number of candidate primer pairs information, the number of candidate primer pairs corresponding to the n candidate amplification regions;

a k-th priority setting step of, using the identification information of the n candidate amplification regions and number-of-candidate-primer pairs information, assigning k-th priority to each of the n candidate amplification regions in order from the smallest of the number of candidate primer pairs;

a step of selecting a predetermined number of candidate amplification regions from the n candidate amplification regions in order from the highest priority as amplification purpose regions and designing at least one primer pair for each of the selected amplification purpose regions; and using the at least one primer pair in multiplex PCR analysis.

8. The method for designing primer pairs according to claim 7, wherein the primer pairs are used in genotyping analysis.

9. A method for designing primer pair for multiplex PCR performed by CPU and an operation program operating the CPU, according to a priority k, the primer pairs PCR amplifying n candidate amplification regions on same chromosomal DNA, and the priority k being assigned to each of the n candidate amplification regions, where k is an integer satisfying 1≤k≤n, and n is an integer satisfying n≥2, the method including a step of selecting the n candidate amplification regions on same chromosomal DNA;

a step of obtaining identification information, the identification information being an identification name R of each of the selected n candidate amplification regions that are assigned identification numbers in an increasing order of coordinate values r of the n candidate amplification regions;

a step of obtaining variant frequency information according to variant frequency VFi of single nucleotide polymorphisms (SNPs) or single nucleotide variant (SNV) of each of the n candidate amplification regions;

a k-th priority setting step of, using the identification information of the n candidate amplification regions and the variant frequency information, calculating a variant frequency difference, $=|0.5-VF_i|$ of each of the n candidate amplification regions and assigning k-th priority to each of the n candidate amplification regions in order from the lowest of the variant frequency difference, the k-th priority setting step being repeated until all of the n candidate amplification regions are each assigned a priority;

a step of selecting a predetermined number of candidate amplification regions from the n candidate amplification regions in order from the highest priority as amplification purpose regions and designing at least one primer pair for each of the selected amplification purpose regions; and using the at least one primer pair in multiplex PCR analysis.

10. The method for designing primer pairs according to claim 9, wherein the primer pairs are used in genotyping analysis.

\* \* \* \* \*

SEQUENCE LISTING

```
<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer,
      chr13.20763642-F

<400> SEQUENCE: 1
tagccggatg tgggagatgg                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer,
      chr13.20763642-R

<400> SEQUENCE: 2
ccagcattgg aaagatctgg                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer,
      chr13.24798120-F
```

```
<400> SEQUENCE: 3
ccgtgtgtga gattctcgtg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer,
      chr13.24798120-R

<400> SEQUENCE: 4
actgctcagg gtcctctgtg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25265103-F

<400> SEQUENCE: 5
ggcctagagg acgatgcttg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25265103-R

<400> SEQUENCE: 6
tgttgataac catgccggtg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer,
      chr13.27845654-F

<400> SEQUENCE: 7
ccttcactcc ccccagtttg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer,
      chr13.27845654-R

<400> SEQUENCE: 8
gcataaaagc agggagcgtg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36385031-F

<400> SEQUENCE: 9
```
gagccacgta tgttggggtg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36385031-R

<400> SEQUENCE: 10
aaagggcttt tgagctcttg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36743177-F

<400> SEQUENCE: 11
aaaccatgcc aactcttttg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36743177-R

<400> SEQUENCE: 12
tctttgcagc aacagttttg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36801415-F

<400> SEQUENCE: 13
agatcacaat cctgggggtg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36801415-R

<400> SEQUENCE: 14
gggtttcagt gctgcaggtg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36886469-F

<400> SEQUENCE: 15

```
gctgcacatt ccaatccttg                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer,
      chr13.36886469-R

<400> SEQUENCE: 16
agatgggaaa tctcctctgg                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer,
      chr13.46946157-F

<400> SEQUENCE: 17
tctcaggata tggggaggtg                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer,
      chr13.46946157-R

<400> SEQUENCE: 18
ggataccaca gactccgttg                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer,
      chr13.52544805-F

<400> SEQUENCE: 19
atgcacaggt catgcctttg                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer,
      chr13.52544805-R

<400> SEQUENCE: 20
atggtgcaaa ctacagatgg                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer,
      chr13.53608479-F

<400> SEQUENCE: 21
aaagctcaga ttccagcttg                                                   20
```

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide primer,
      chr13.53608479-R

<400> SEQUENCE: 22
ctctgtccac gggaaaggtg                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide primer,
      chr13.67800935-F

<400> SEQUENCE: 23
gtaacaatca cagccgcttg                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer,
      chr13.67800935-R

<400> SEQUENCE: 24
accgaatgcc tccttctttg                                                 20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide primer,
      chr13.95858978-F

<400> SEQUENCE: 25
cgaggagcac gtaggtggtg                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer,
      chr13.95858978-R

<400> SEQUENCE: 26
tgagccactt tatctggttg                                                 20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer,
      chr13.102366825-F

<400> SEQUENCE: 27
cattgtggga agtgcatttg                                                 20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer,
      chr13.102366825-R

<400> SEQUENCE: 28
tgcatgacga gtgtctcttg                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide primer,
      chr13.103396716-F

<400> SEQUENCE: 29
ttcagatgac atgaggctgg                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer,
      chr13.103396716-R

<400> SEQUENCE: 30
acagggaaat caaagattgg                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide primer,
      chr13.103397937-F

<400> SEQUENCE: 31
cagcaccagc cctgatattg                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer,
      chr13.103397937-R

<400> SEQUENCE: 32
aaagagacag cgatttttgg                                                20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer,
      chr13.111098226-F

<400> SEQUENCE: 33
gccattgcag tcccttttg                                                 20

```
<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer,
      chr13.111098226-R

<400> SEQUENCE: 34
tgggcgagac accataagtg                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide primer,
      chr13.20763380-F

<400> SEQUENCE: 35
cttcgatgcg gaccttctgg                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer,
      chr13.20763380-R

<400> SEQUENCE: 36
tctcccacat ccggctatgg                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21086599-F

<400> SEQUENCE: 37
cccacttcca ttccttctgg                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21086599-R

<400> SEQUENCE: 38
cccttcagtg gagtcattgg                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21205192-F

<400> SEQUENCE: 39
tttccccgac cataagcttg                                                    20

<210> SEQ ID NO 40
```

```
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21205192-R

<400> SEQUENCE: 40
atacagggct gagagattgg                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21383364-F

<400> SEQUENCE: 41
attcctacac tggccagttg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21383364-R

<400> SEQUENCE: 42
agccacagaa gtgcacgttg                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21620085-F

<400> SEQUENCE: 43
tgataaggtc cgaactttgg                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide primer,
      chr13.21620085-R

<400> SEQUENCE: 44
gcgactgcaa gagattcgtg                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide primer,
      chr13.23898664-F

<400> SEQUENCE: 45
gtacctgtct gtggccggtg                                              20

<210> SEQ ID NO 46
<211> LENGTH: 20
```

```
<212> TYPE: DNA
<213> ORGANISM: Artificial Sequence
<220> FEATURE:
<223> OTHER INFORMATION: Synthetic oligonucleotide primer,
      chr13.23898664-R

<400> SEQUENCE: 46
cctcagtctt tcacgatgtg                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide primer,
      chr13.23908034-F

<400> SEQUENCE: 47
gagccttcaa gatgcttgtg                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide primer,
      chr13.23908034-R

<400> SEQUENCE: 48
ttttccaaat gcccagagtg                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25009099-F

<400> SEQUENCE: 49
aatccagctc agggaaggtg                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25009099-R

<400> SEQUENCE: 50
atcccacagt cggcgtcttg                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25029218-F

<400> SEQUENCE: 51
ccaaagcgca ctcacctgtg                                              20

<210> SEQ ID NO 52
<211> LENGTH: 20
<212> TYPE: DNA
```

```
<213> ORGANISM: Artificial Sequence
<220> FEATURE:
<223> OTHER INFORMATION: Synthetic oligonucleotide primer,
      chr13.25029218-R

<400> SEQUENCE: 52
tagccagtga gagcgaagtg                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25265103-F

<400> SEQUENCE: 53
ggccttggga atgtggtgtg                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25265103-R

<400> SEQUENCE: 54
ggcaatatgg ccaatgatgg                                                   20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25266932-F

<400> SEQUENCE: 55
tgctggacag tgactcatgg                                                   20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide primer,
      chr13.25266932-R

<400> SEQUENCE: 56
cattttcctg tcctggcttg                                                   20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide primer,
      chr13.28610183-F

<400> SEQUENCE: 57
ttcttccagg tccaagatgg                                                   20

<210> SEQ ID NO 58
<211> LENGTH: 20
<212> TYPE: DNA
<213> ORGANISM: Artificial Sequence
```

```
<220> FEATURE:
<223> OTHER INFORMATION: Synthetic oligonucleotide primer,
      chr13.28610183-R

<400> SEQUENCE: 58
ttggcttcac aaagtattgg                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide primer,
      chr13.28624294-F

<400> SEQUENCE: 59
cctgcccagt tcatttctgg                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide primer,
      chr13.28624294-R

<400> SEQUENCE: 60
tcctcttgag cattcatttg                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide primer,
      chr13.26043182-F

<400> SEQUENCE: 61
cctggcggtt gacttctttg                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide primer,
      chr13.26043182-R

<400> SEQUENCE: 62
aatttgttga gatgcggttg                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide primer,
      chr13.28367956-F

<400> SEQUENCE: 63
agaagcaggt gaagatctgg                                              20

<210> SEQ ID NO 64
<211> LENGTH: 20
<212> TYPE: DNA
<213> ORGANISM: Artificial Sequence
<220> FEATURE:
```

<223> OTHER INFORMATION: Synthetic oligonucleotide primer, chr13.28367956-R

<400> SEQUENCE: 64
cgtcatcctc ggagcacttg                                                              20